(12) United States Patent
Banning et al.

(10) Patent No.: US 7,732,625 B2
(45) Date of Patent: *Jun. 8, 2010

(54) COLORANT COMPOUNDS

(75) Inventors: Jeffrey H. Banning, Hillsboro, OR (US); Bo Wu, Wilsonville, OR (US); Randall R. Bridgeman, Hubbard, OR (US); Donald R. Titterington, Newberg, OR (US)

(73) Assignee: Xerox Corporation, Norwalk, CT (US)

( * ) Notice: Subject to any disclaimer, the term of this patent is extended or adjusted under 35 U.S.C. 154(b) by 1287 days.

This patent is subject to a terminal disclaimer.

(21) Appl. No.: 10/898,028

(22) Filed: Jul. 23, 2004

(65) Prior Publication Data
US 2006/0020141 A1    Jan. 26, 2006

(51) Int. Cl.
*C07D 311/00* (2006.01)
(52) U.S. Cl. .................................................. 549/212
(58) Field of Classification Search ................... 549/212
See application file for complete search history.

(56) References Cited

U.S. PATENT DOCUMENTS

| | | | |
|---|---|---|---|
| 1,981,515 A | 11/1934 | Kyrides | 260/128 |
| 1,981,516 A | 11/1934 | Kyrides | 260/128 |
| 1,991,482 A | 2/1935 | Allemann | 260/63 |
| 3,653,932 A | 4/1972 | Berry et al. | 106/22 |
| 4,390,369 A | 6/1983 | Merritt et al. | 106/31 |
| 4,484,948 A | 11/1984 | Merritt et al. | 106/31 |
| 4,647,675 A | 3/1987 | Mayer et al. | 549/394 |
| 4,684,956 A | 8/1987 | Ball | 346/1.1 |
| 4,851,045 A | 7/1989 | Taniguchi | 106/31 |
| 4,889,560 A | 12/1989 | Jaeger et al. | 106/27 |
| 4,889,761 A | 12/1989 | Titterington et al. | 428/195 |
| 4,935,059 A | 6/1990 | Mayer et al. | 106/22 |
| 5,006,170 A | 4/1991 | Schwarz et al. | 106/20 |
| 5,084,099 A | 1/1992 | Jaeger et al. | 106/22 |
| 5,151,120 A | 9/1992 | You et al. | 106/27 |
| 5,221,335 A | 6/1993 | Williams et al. | 106/23 A |
| 5,372,852 A | 12/1994 | Titterington et al. | 427/288 |
| 5,496,879 A | 3/1996 | Griebel et al. | 524/320 |
| 5,507,864 A | 4/1996 | Jaeger et al. | 106/22 A |
| 5,621,022 A | 4/1997 | Jaeger et al. | 523/161 |
| 5,747,554 A | 5/1998 | Sacripante et al. | 523/161 |
| 5,847,162 A | 12/1998 | Lee et al. | 549/227 |
| 5,902,841 A | 5/1999 | Jaeger et al. | 523/161 |
| 6,998,493 B2 * | 2/2006 | Banning et al. | 549/212 |
| 2004/0077887 A1 | 4/2004 | Banning et al. | 552/237 |
| 2004/0082801 A1 | 4/2004 | Jaeger et al. | 552/225 |
| 2004/0102540 A1 | 5/2004 | Jaeger et al. | 523/160 |

FOREIGN PATENT DOCUMENTS

| | | |
|---|---|---|
| EP | 0 206 286 B1 | 5/1990 |
| EP | 0 187 352 B1 | 6/1991 |
| EP | 0 565 798 B2 | 3/2001 |
| GB | 2 311 075 | 9/1997 |
| WO | WO 94/04619 | 3/1994 |

OTHER PUBLICATIONS

Copending U.S. Appl. No. 10/606,705, filed Jun. 26, 2003, entitled "Phase Change Inks Containing Colorant Compounds," by Wu et al.
Copending U.S. Appl. No. 10/898,724, by Wu et al., filed Jul. 23, 2004.
Copending U.S. Appl. No. 10/898,432, by Wu et al., Jul. 23, 2004.
English abstract for German Patent Publication DE 4205636AL, 1993.
English abstract for German Patent Publication DE 4205713AL, 1996.
"Rhodamine Dyestuffs and Related Compounds. XV. Rhodamine Dyestuffs with Hydroaromatic and Polymethylene Radicals," I. S. Ioffe et al., *Zh. Organ. Khim.* (1965), 1(3), 584-6.

(Continued)

*Primary Examiner*—Barbara P Badio
(74) *Attorney, Agent, or Firm*—Oliff & Berridge, PLC

(57) ABSTRACT

Rhodamine, thio-rhodamine, acridine, and carbopyronin compounds of the formula

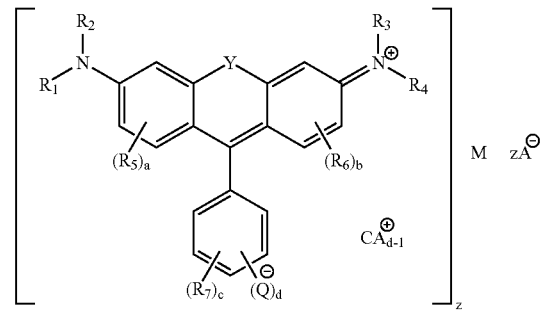

wherein M is either (1) a metal ion having a positive charge of +y wherein y is an integer which is at least 2, said metal ion being capable of forming a compound with at least two

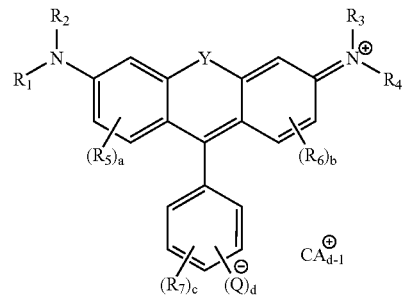

chromogen moieties, or (2) a metal-containing moiety capable of forming a compound with at least two chromogen moieties, z is an integer representing the number of chromogen moieties associated with the metal and is at least 2, $R_1$, $R_2$, $R_3$, $R_4$, $R_5$, $R_6$, $R_7$, a, b, c, d, Y, and z are as defined herein, $Q^-$ is a $COO^-$ group or a $SO_3^-$ group, A is an organic anion, and CA is either a hydrogen atom or a cation associated with all but one of the $Q^-$ groups.

39 Claims, No Drawings

OTHER PUBLICATIONS

Copending U.S. Appl. No. 10/607,373, filed Jun. 26, 2003, entitled "Colorant Compounds," by Banning et al.
Copending U.S. Appl. No. 10/606,631, filed Jun. 26, 2003, entitled "Phase Change Inks Containing Colorant Compounds," by Wu et al.
Copending U.S. Appl. No. 10/607,382, filed Jun. 26, 2003, entitled "Colorant Compounds," by Banning et al.
"Rhodamine Dyes and Related Compounds. XI. Biscarboxyaryl- and Biscarboxyalkyl-Rhodamines," I. S. Ioffe et al., *Zh. Obsch. Khim.* (1964), 34(6), 2041-4.
"Rhodamine Dyes and Related Compounds. X. Fluorescence of Solutions of Alkyl- and Arylalkylrhodamines," I. S. Ioffe et al., *Zh. Obsch. Khim.* (1964), 34(6), 2039-41 Abstract only.
"Rhodamine Dyes and Related Compounds. IX. Sulfonic Acids of Rhodamine B and their Derivatives," I. S. Ioffe et al., *Zh. Obsch. Khim.* (1964), 34(2), 640-44.
"Rhodamine Dyes and Related Compounds. VIII. Amides of Sulforhodamine B Containing β-Hydroxyethyl and β-Chloroethyl Groups," I. S. Ioffe et al., *Zh. Obsch. Khim.* (1963), 33(12), 3943-6.
"Rhodamine Dyes and Related Compounds. VII. (β-Phenylethyl)rhodamines," I. S. Ioffe et al., *Zh. Obsch. Khim.* (1963), 33(4), 1089-92.
"Rhodamine Dyes and Related Compounds. VI. Chloride and Amides of Sulforhodamine B," I. S. Ioffe et al., *Zh. Obsch. Khim.* (1962), 32, 1489-92 Abstract only.
"Rhodamine Dyes and Related Compounds. V. α-Pyridylrhodamine," I. S. Ioffe et al., *Zh. Obsch. Khim.* (1962), 32, 1485-9.
"Rhodamine Dyes and Related Compounds. IV. Aryl- and Benzylrhodamines," I. S. Ioffe et al., *Zh. Obsch. Khim.* (1962), 32, 1480-5.
"Rhodamine Dyes and Related Compounds. III. Reaction of m-aminophenol With Phthalic Anhydride in Hot Sulfuric Acid," I. S. Ioffe et al., *Zh. Obsch. Khim.* (1962), 32, 1477-80. Abstract only.
"Rhodamine Dyes and Related Compounds. XVIII. N,N'-Dialkylrhodamines with Heavy Hydrocarbon Radicals," I. S. Ioffe et al., *Zh. Organ. Khim.* (1970), 6(2), 369-71.
"Rhodamine Dyes and Related Compounds. XIX. Mutual Conversions of the Colorless and Colored Forms of N,N'-Substituted Rhodamines," I. S. Ioffe et al., *Zh. Organ. Khim.* (1972), 8(8), 1726-9.
"Synthesis of N-Substituted Flaveosines, Acridine Analogs of Rhodamine Dyes," I. S. Ioffe et al., *Zh. Org. Khim.* (1966), 2(9), 1721.
"Rhodamine Dyes and Related Compounds. XVII. Acridine Analogs of Rhodamine and Fluorescein," I. S. Ioffe et al., *Zh. Organ. Khim.* (1966), 2(5), 927-31.
"New Lipophilic Rhodamines and Their Application to Optical Potassium Sensing," T. Werner et al., *Journal of Fluorescence*, vol. 2, No. 3, pp. 93-98 (1992).
English abstract British Patent Publication GB 421 737, 1934.
English abstract for Japanese Patent Publication JP 61221265, 1986.

* cited by examiner

COLORANT COMPOUNDS

CROSS-REFERENCE TO RELATED APPLICATIONS

Copending Application U.S. Ser. No. 10/260,146, filed Sep. 27, 2002, U.S. Publication 20040077887, entitled "Colorant Compounds," with the named inventors Jeffery H. Banning and C. Wayne Jaeger, the disclosure of which is totally incorporated herein by reference, discloses compounds of the formula

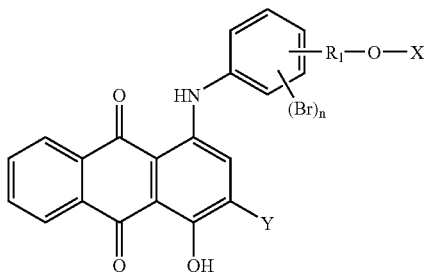

wherein Y is a hydrogen atom or a bromine atom, n is an integer of 0, 1, 2, 3, or 4, $R_1$ is an alkylene group or an arylalkylene group, and X is (a) a hydrogen atom, (b) a group of the formula

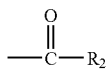

wherein $R_2$ is an alkyl group, an aryl group, an arylalkyl group, or an alkylaryl group, (c) an alkyleneoxy, aryleneoxy, arylalkyleneoxy, or alkylaryleneoxy group, or (d) a group of the formula

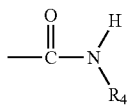

wherein $R_4$ is an alkyl group, an aryl group, an arylalkyl group, or an alkylaryl group.

Copending Application U.S. Ser. No. 10/260,376, filed Sep. 27, 2002, U.S. Publication 20040102540 A1, entitled "Phase Change Inks," with the named inventors C. Wayne Jaeger and Jeffery H. Banning, the disclosure of which is totally incorporated herein by reference, discloses a phase change ink composition comprising a phase change ink carrier and a colorant compound of the formula

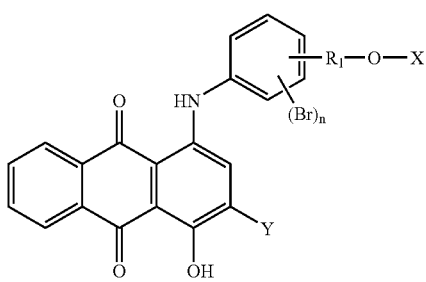

wherein Y is a hydrogen atom or a bromine atom, n is an integer of 0, 1, 2, 3, or 4, $R_1$ is an alkylene group or an arylalkylene group, and X is (a) a hydrogen atom, (b) a group of the formula

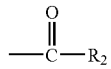

wherein $R_2$ is an alkyl group, an aryl group, an arylalkyl group, or an alkylaryl group, (c) an alkyleneoxy, aryleneoxy, arylalkyleneoxy, or alkylaryleneoxy group, or (d) a group of the formula

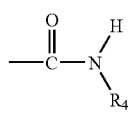

wherein $R_4$ is an alkyl group, an aryl group, an arylalkyl group, or an alkylaryl group.

Copending Application U.S. Ser. No. 10/260,379, filed Sep. 27, 2002, U.S. Publication 20040082801, entitled "Methods for Making Colorant Compounds," with the named inventors C. Wayne Jaeger and Jeffery H. Banning, the disclosure of which is totally incorporated herein by reference, discloses a process for preparing a colorant of the formula

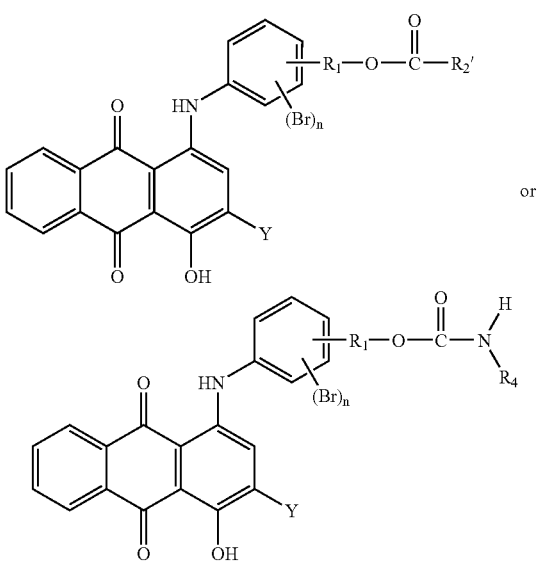

wherein Y is a hydrogen atom or a bromine atom, n is an integer of 0, 1, 2, 3, or 4, $R_1$ is an alkylene group or an arylalkylene group, $R_2$ is an alkyl group, an aryl group, an arylalkyl group, or an alkylaryl group, and $R_4$ is an alkyl group, an aryl group, an arylalkyl group, or an alkylaryl group, can be prepared by a process which comprises (a) preparing a first reaction mixture by admixing (1) leucoquinizarin and, optionally, quinizarin, (2) an aminobenzene substituted with an alcohol group of the formula —$R_1$—OH, (3) boric acid, and (4) an optional solvent, and heating the first reaction mixture to prepare an alcohol-substituted colorant of the formula

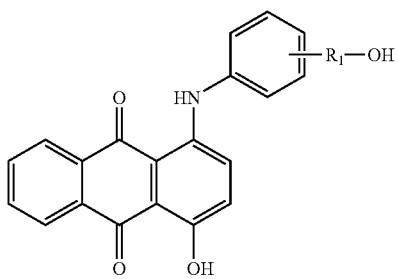

followed by (b) converting the colorant thus prepared to either (i) an ester-substituted colorant by reaction with an esterification compound which is either (A) an anhydride of the formula

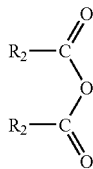

or (B) an acid of the formula $R_2COOH$ in the presence of an optional esterification catalyst, or (ii) a urethane-substituted colorant by reaction with an isocyanate compound of the formula

and (c) brominating the colorant thus prepared, wherein either conversion to ester or urethane can be performed before bromination or bromination can be performed before conversion to ester or urethane.

Copending Application U.S. Ser. No. 10/607,373, filed Jun. 26, 2003, entitled "Colorant Compounds," with the named inventors Jeffery H. Banning, Bo Wu, James M. Duff, Wolfgang G. Wedler, Jule W. Thomas, and Randall R. Bridgeman, the disclosure of which is totally incorporated herein by reference, discloses compounds of the formula

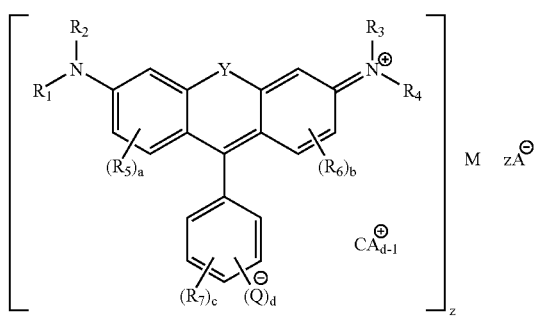

wherein M is either (1) a metal ion having a positive charge of +y wherein y is an integer which is at least 2, said metal ion being capable of forming a compound with at least two

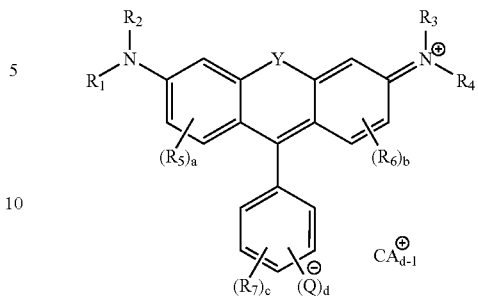

chromogen moieties, or (2) a metal-containing moiety capable of forming a compound with at least two

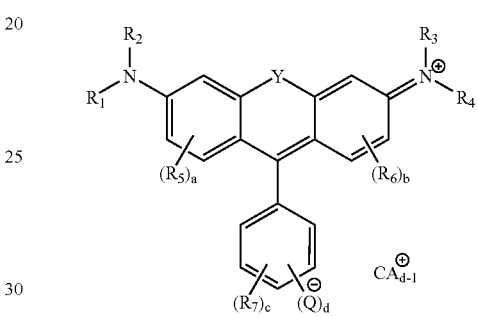

chromogen moieties, z is an integer representing the number of

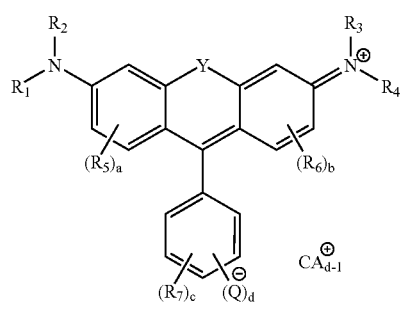

chromogen moieties associated with the metal and is at least 2, and $R_1$, $R_2$, $R_3$, $R_4$, $R_5$, $R_6$, $R_7$, a, b, c, d, Y, $Q^-$, A, and CA are as defined therein.

Copending Application U.S. Ser. No. 10/606,631, filed Jun. 26, 2003, entitled "Phase Change Inks Containing Colorant Compounds," with the named inventors Bo Wu, Jeffery H. Banning, James M. Duff, Wolfgang G. Wedler, Jule W. Thomas, and Randall R. Bridgeman, the disclosure of which is totally incorporated herein by reference, discloses a phase change ink composition comprising a phase change ink carrier and a colorant compound of the formula

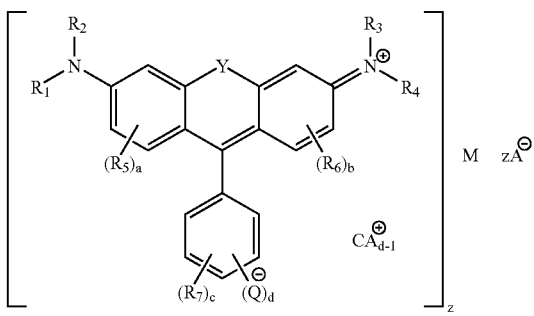

wherein M is either (1) a metal ion having a positive charge of +y wherein y is an integer which is at least 2, said metal ion being capable of forming a compound with at least two

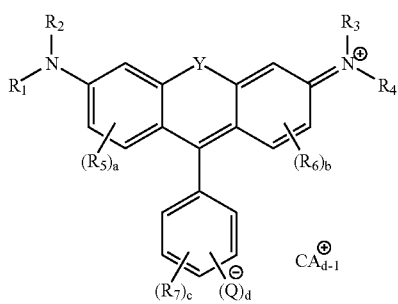

chromogen moieties, or (2) a metal-containing moiety capable of forming a compound with at least two

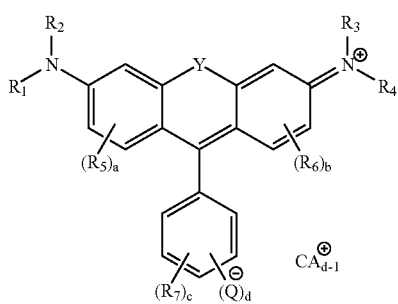

chromogen moieties, z is an integer representing the number of

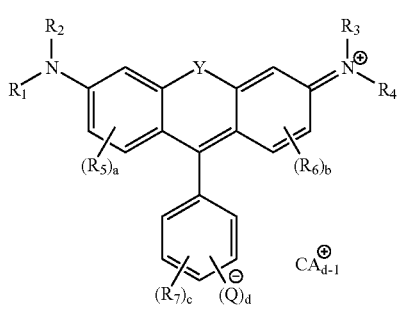

chromogen moieties associated with the metal and is at least 2, and $R_1$, $R_2$, $R_3$, $R_4$, $R_5$, $R_6$, $R_7$, a, b, c, d, Y, $Q^-$, A, and CA are as defined therein.

Copending Application U.S. Ser. No. 10/607,382, filed Jun. 26, 2003, entitled "Colorant Compounds," with the named inventors Jeffery H. Banning, Bo Wu, James M. Duff, Wolfgang G. Wedler, and Donald R. Titterington, the disclosure of which is totally incorporated herein by reference, discloses compounds of the formulae

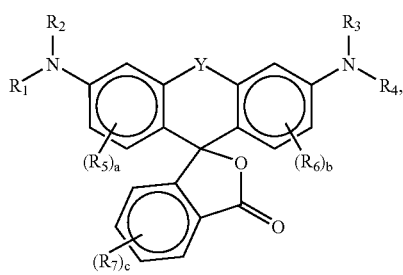

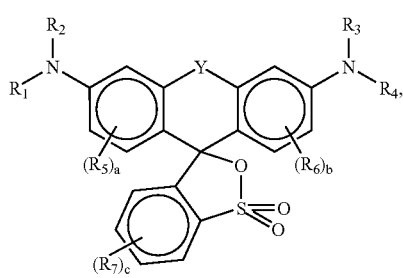

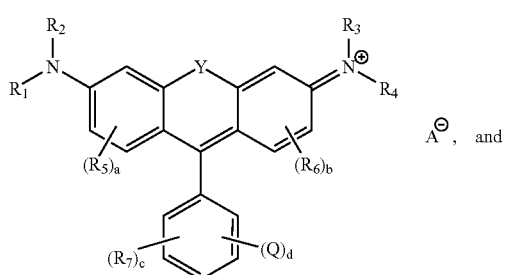

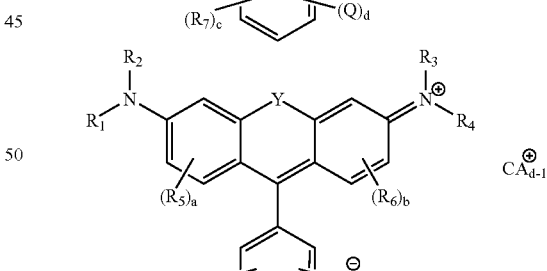

wherein $R_1$, $R_2$, $R_3$, $R_4$, $R_5$, $R_6$, $R_7$, a, b, c, d, Y, Q, $Q^-$, A, and CA are as defined therein.

Copending Application U.S. Ser. No. 10/606,705, filed Jun. 26, 2003, entitled "Phase Change Inks Containing Colorant Compounds," with the named inventors Bo Wu, Jeffery H. Banning, James M. Duff, Wolfgang G. Wedler, and Donald R. Titterington, the disclosure of which is totally incorporated herein by reference, discloses phase change inks comprising a carrier and a colorant of the formula

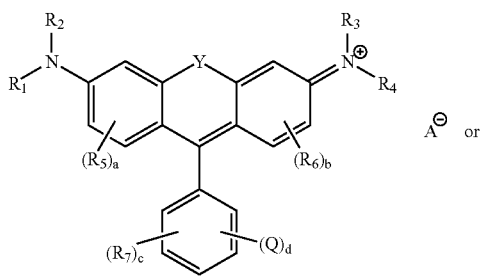

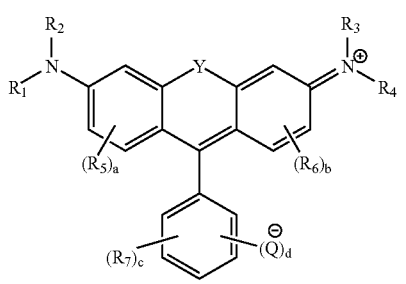

wherein $R_1$, $R_2$, $R_3$, $R_4$, $R_5$, $R_6$, $R_7$, a, b, c, d, Y, Q, $Q^-$, A, and CA are as defined therein.

Copending Application U.S. Ser. No. 10/898,724, filed Jul. 23, 2004, entitled "Processes for Preparing Phase Change Inks," with the named inventors Bo Wu, Jeffery H. Banning, Randall R. Bridgeman, and Donald R. Titterington, the disclosure of which is totally incorporated herein by reference, discloses processes for preparing phase change inks comprising admixing (a) a phase change ink carrier; (b) a colorant of the formula

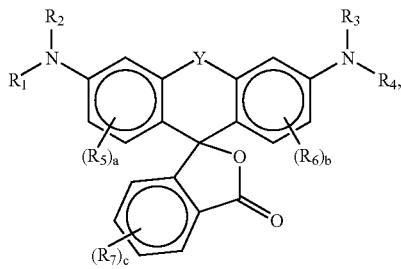

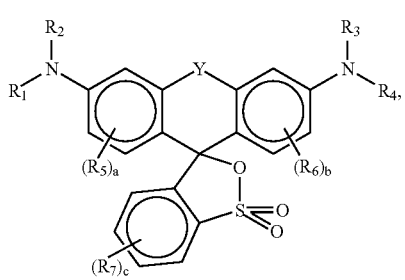

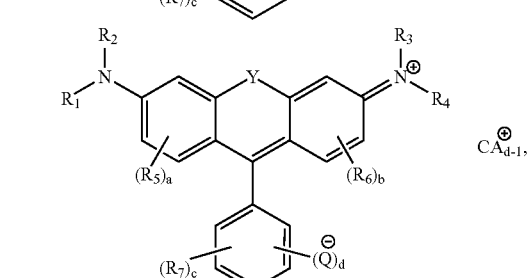

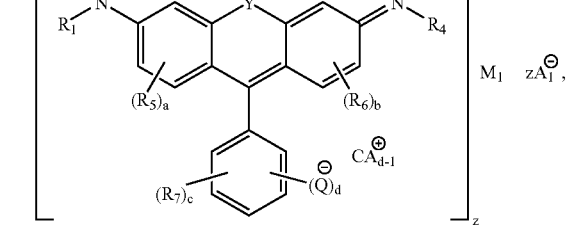

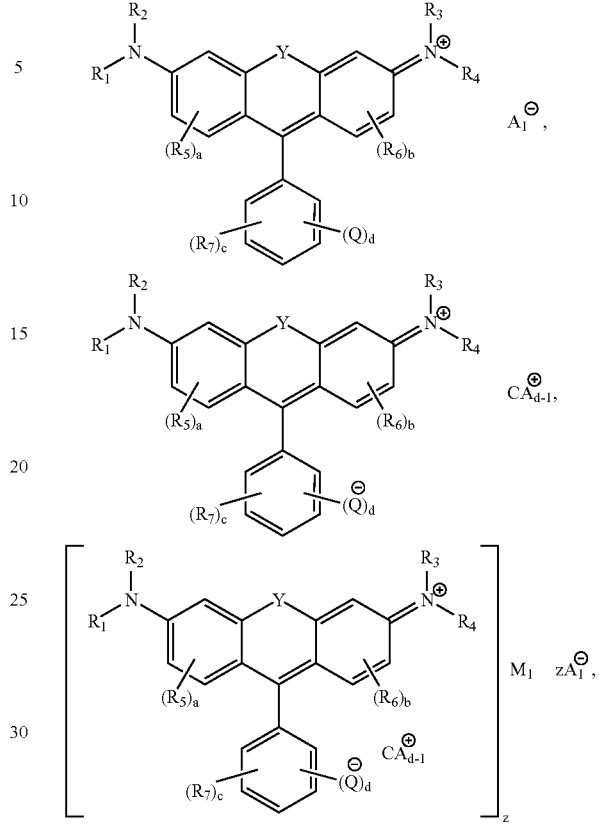

or mixtures thereof, wherein $M_1$, z, $A_1$, $R_1$, $R_2$, $R_3$, $R_4$, $R_5$, $R_6$, $R_7$, a, b, c, d, Y, Q, $Q^-$, $A_1$, and CA are as defined herein; and (c) a metal salt of the formula $(M_2^{v+})_w(A_2^{w-})_v$ of which the metal portion $M_2$ is either a metal ion having positive charge +v, a metal-containing moiety, or a mixture thereof, and $A_2$ is an anion having negative charge −w, wherein $M_1$ and $M_2$ can be the same as or different from each other, wherein $A_1$ and $A_2$ can be the same as or different from each other, said admixing occurring at a temperature at which the ink carrier is a liquid.

Copending Application U.S. Ser. No. 10/898,432, filed concurrently herewith, entitled "Phase Change Inks," with the named inventors Bo Wu, Jeffery H. Banning, Randall R. Bridgeman, and Donald R. Titterington, the disclosure of which is totally incorporated herein by reference, discloses phase change ink compositions comprising a phase change ink carrier and a colorant compound of the formula

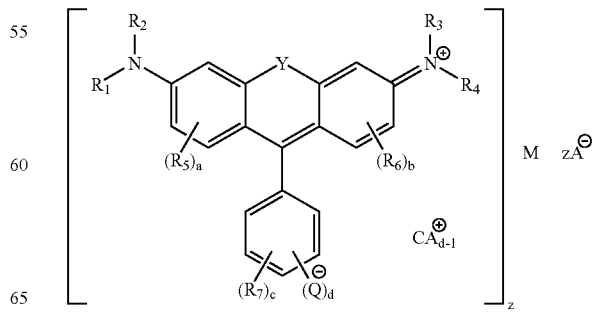

wherein M is either (1) a metal ion having a positive charge of +y wherein y is an integer which is at least 2, said metal ion being capable of forming a compound with at least two

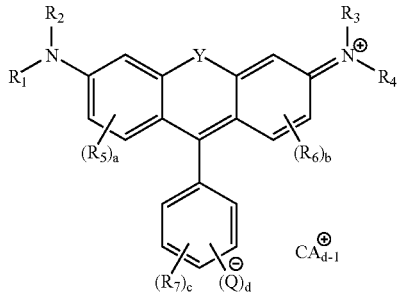

chromogen moieties, or (2) a metal-containing moiety capable of forming a compound with at least two

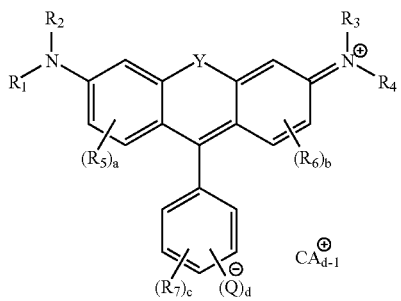

chromogen moieties, z is an integer representing the number of

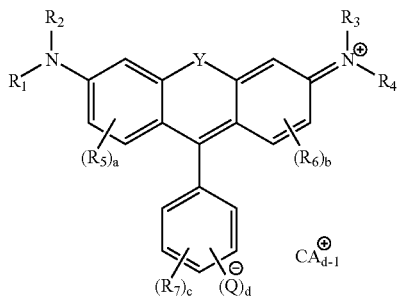

chromogen moieties associated with the metal and is at least 2, $R_1$, $R_2$, $R_3$, $R_4$, $R_5$, $R_6$, $R_7$, a, b, c, d, Y, and z are as defined herein, $Q^-$ is a $COO^-$ group or a $SO_3^-$ group, A is an organic anion, and CA is either a hydrogen atom or a cation associated with all but one of the $Q^-$ groups.

BACKGROUND

Disclosed herein are colorant compounds. More specifically, disclosed herein are colorant compounds particularly suitable for use in hot melt or phase change inks. One embodiment is directed to compounds of the formula

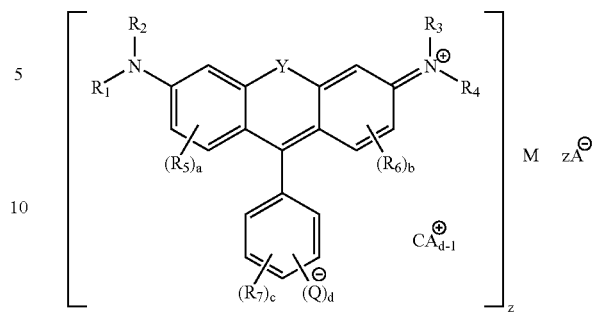

wherein M is either (1) a metal ion having a positive charge of +y wherein y is an integer which is at least 2, said metal ion being capable of forming a compound with at least two

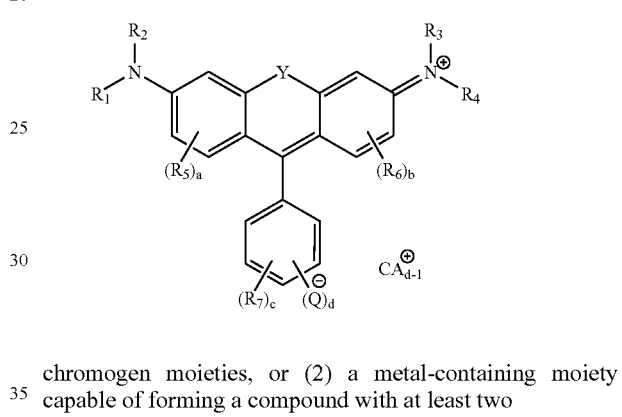

chromogen moieties, or (2) a metal-containing moiety capable of forming a compound with at least two

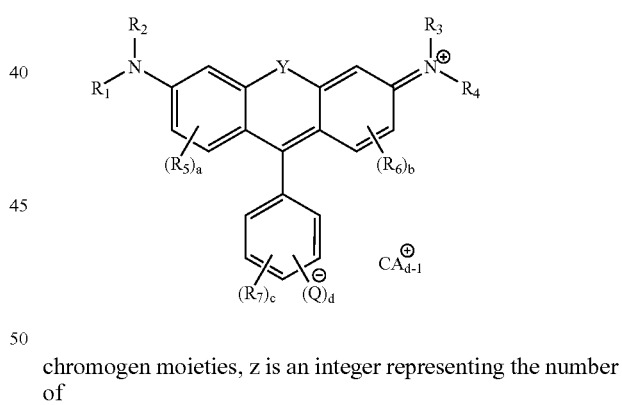

chromogen moieties, z is an integer representing the number of

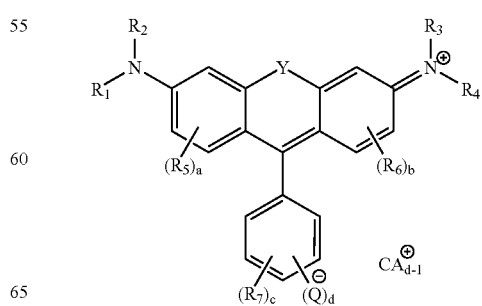

chromogen moieties associated with the metal and is at least 2, $R_1$, $R_2$, $R_3$, and $R_4$ each, independently of the others, is (i) a hydrogen atom, (ii) an alkyl group, (iii) an aryl group, (iv) an arylalkyl group, or (v) an alkylaryl group, wherein $R_1$ and $R_2$ can be joined together to form a ring, wherein $R_3$ and $R_4$ can be joined together to form a ring, and wherein $R_1$, $R_2$, $R_3$, and $R_4$ can each be joined to a phenyl ring in the central structure, a and b each, independently of the others, is an integer which is 0, 1, 2, or 3, c is an integer which is 0, 1, 2, 3, or 4, each $R_5$, $R_6$, and $R_7$, independently of the others, is (i) an alkyl group, (ii) an aryl group, (iii) an arylalkyl group, (iv) an alkylaryl group, (v) a halogen atom, (vi) an ester group, (vii) an amide group, (viii) a sulfone group, (ix) an amine group or ammonium group, (x) a nitrile group, (xi) a nitro group, (xii) a hydroxy group, (xiii) a cyano group, (xiv) a pyridine or pyridinium group, (xv) an ether group, (xvi) an aldehyde group, (xvii) a ketone group, (xviii) a carbonyl group, (xix) a thiocarbonyl group, (xx) a sulfate group, (xxi) a sulfide group, (xxii) a sulfoxide group, (xxiii) a phosphine or phosphonium group, (xxiv) a phosphate group, (xxv) a mercapto group, (xxvi) a nitroso group, (xxvii) an acyl group, (xxviii) an acid anhydride group, (xxix) an azide group, (xxx) an azo group, (xxxi) a cyanato group, (xxxii) an isocyanato group, (xxxiii) a thiocyanato group, (xxxiv) an isothiocyanato group, (xxxv) a urethane group, or (xxxvi) a urea group, wherein $R_5$, $R_6$, and $R_7$ can each be joined to a phenyl ring in the central structure,

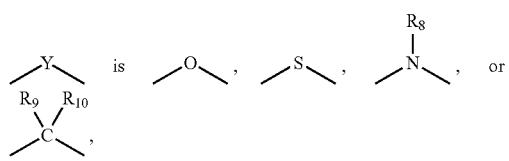

$R_8$, $R_9$, and $R_{10}$ each, independently of the others, is (i) a hydrogen atom, (ii) an alkyl group, (iii) an aryl group, (iv) an arylalkyl group, or (v) an alkylaryl group, provided that the number of carbon atoms in $R_1+R_2+R_3+R_4+R_5+R_6+R_7+R_8+R_9+R_{10}$ is at least about 16, $Q^-$ is a $COO^-$ group or a $SO_3^-$ group, d is an integer which is 1, 2, 3, 4, or 5, A is an organic anion, and CA is either a hydrogen atom or a cation associated with all but one of the $Q^-$ groups.

In general, phase change inks (sometimes referred to as "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing, as disclosed in, for example, U.S. Pat. No. 5,496,879 and German Patent Publications DE 4205636AL and DE 4205713AL, the disclosures of each of which are totally incorporated herein by reference.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. No. 4,889,560, U.S. Pat. No. 4,889,761, and U.S. Pat. No. 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes. The colorants can also include pigments, as disclosed in, for example, U.S. Pat. No. 5,221,335, the disclosure of which is totally incorporated herein by reference. U.S. Pat. No. 5,621,022, the disclosure of which is totally incorporated herein by reference, discloses the use of a specific class of polymeric dyes in phase change ink compositions.

Phase change inks have also been used for applications such as postal marking, industrial marking, and labelling.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Compositions suitable for use as phase change ink carrier compositions are known. Some representative examples of references disclosing such materials include U.S. Pat. No. 3,653,932, U.S. Pat. No. 4,390,369, U.S. Pat. No. 4,484,948, U.S. Pat. No. 4,684,956, U.S. Pat. No. 4,851,045, U.S. Pat. No. 4,889,560, U.S. Pat. No. 5,006,170, U.S. Pat. No. 5,151,120, U.S. Pat. No. 5,372,852, U.S. Pat. No. 5,496,879, European Patent Publication 0187352, European Patent Publication 0206286, German Patent Publication DE 4205636AL, German Patent Publication DE 4205713AL, and PCT Patent Application WO 94/04619, the disclosures of each of which are totally incorporated herein by reference. Suitable carrier materials can include paraffins, microcrystalline waxes, polyethylene waxes, ester waxes, fatty acids and other waxy materials, fatty amide containing materials, sulfonamide materials, resinous materials made from different natural sources (tall oil rosins and rosin esters, for example), and many synthetic resins, oligomers, polymers, and copolymers.

British Patent Publication GB 2 311 075 (Gregory et al.), the disclosure of which is totally incorporated herein by reference, discloses a compound of the formula

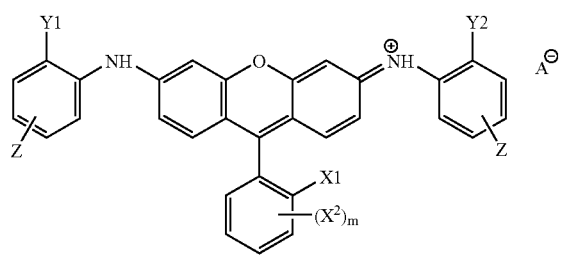

wherein $X^1$ is an ester group or an amide group (such as of a carboxylic or sulfonic acid) or a fatty amine salt of a sulfonic acid, each $X^2$ independently is a substituent, m has a value of from 0 to 2, $Y^1$ and $Y^2$ are each independently H, alkyl, or halo, each Z independently is an ester or amide group, and $A^-$ is an anion. The compound is useful as a colorant for toners, D2T2 printing, plastics, polyesters, nylons, and inks, especially ink jet or hot melt inks.

"Rhodamine Dyestuffs and Related Compounds. XV. Rhodamine Dyestuffs with Hydroaromatic and Polymethylene Radicals," I. S. Ioffe et al., *Zh. Organ. Khim.* (1965), 1(3), 584-6, the disclosure of which is totally incorporated herein by reference, discloses a process wherein heating dichlorofluoran with $ZnCl_2$—ZnO and the appropriate amine for 3 hours at 220° followed by treatment with aqueous HCl gave N,N'-dicyclohexylrhodamine-HCl, m. 180-5°, N,N'-di(tetramethylene)rhodamine-HCl, decompd. 240°, N,N'-di(pentamethylene)rhodamine-HCl, m. 205-10°, N,N'-di(hexamethylene)rhodamine-HCl, decompd. 175°. These dyes gave yellow or orange fluorescence and their spectra were given.

"Rhodamine Dyes and Related Compounds. XI. Biscarboxyaryl- and Biscarboxyalkyl-Rhodamines," I. S. Ioffe et al., *Zh. Obsch. Khim.* (1964), 34(6), 2041-4, the disclosure of which is totally incorporated herein by reference, discloses a process wherein heating aminobenzoic acids with 3,6-dichlorofluoran in the presence of $ZnCl_2$ for 6 hours at 24-50° gave after an aqueous treatment: N,N'-bis(o-carboxyphenyl)rhodamine-HCl; m-isomer-HCl; and p-isomer-HCl. A similar reaction with HCl salts of glycine, α-alanine, or β-alanine gave: N,N'-bis(carboxymethyl)rhodamine-HCl; N,N'-bis(α-carboxyethyl)rhodamine-HCl; and N,N'-bis(β-carboxyethyl)rhodamine-HCl. The latter group showed yellow-green fluorescence, lacking in the aryl derivatives. Spectra of the products are shown.

"Rhodamine Dyes and Related Compounds. X. Fluorescence of Solutions of Alkyl- and Arylalkylrhodamines," I. S. Ioffe et al., *Zh. Obsch. Khim.* (1964), 34(6), 2039-41, the disclosure of which is totally incorporated herein by reference, discloses fluorescence spectra for the following rhodamines: N,N'-diethyl; N,N'-dibenzyl; N,N'-bis(β-phenylethyl); N,N'-bis(β-phenylisopropyl). In symmetrical substituted rhodamines, the entry of an alkyl or arylalkyl group into both amino residues resulted in the displacement of fluorescence max. toward longer wavelengths, a similar displacement of absorption and an increase in the quantum yield of fluorescence. In unsymmetrical derivatives, an aryl group entering one of the amino groups shifted the spectra to a greater degree in the same direction and sharply reduced the quantum yield of fluorescence.

"Rhodamine Dyes and Related Compounds. IX. Sulfonic Acids of Rhodamine B and their Derivatives," I. S. Ioffe et al., *Zh. Obsch. Khim.* (1964), 34(2), 640-44, the disclosure of which is totally incorporated herein by reference, discloses that heating m-$Et_2NC_6H_4OH$ and K β-sulfophthalate at 150° while concentrated $H_2SO_4$ was being added gave after 3 hours at 150-70°, followed by heating with $H_2O$ 15 min., a residue of crude sulforhodamine, purified by solution in hot aqueous $Na_2CO_3$ and precipitation with AcOH. The mixed isomeric rhodamine sulfonic acids refluxed 3 hours with 30% AcOH, clarified, and cooled gave a first isomer with Rf 0.74 on paper in aqueous solution (pH 9) while the residue was the other isomer with Rf 0.98. The first isomer and $PCl_5$ gave the sulfonyl chloride, isolated as HCl salt, red solid (from $CHCl_3$-ligroine), which with $NH_3$ in $CHCl_3$ gave the sulfonamide, a violet powder. The two isomers and Rhodamine B had similar spectral characteristics. The two isomers probably contain the $SO_3H$ group in the 4- and 5-positions of the Ph ring of Rhodamine B. Their absorption and fluorescence spectra are shown. Their solutions in $CHCl_3$ gave stronger fluorescence than those in $Me_2CO$.

"Rhodamine Dyes and Related Compounds. VIII. Amides of Sulforhodamine B Containing β-Hydroxyethyl and β-Chloroethyl Groups," I. S. Ioffe et al., *Zh. Obsch. Khim.* (1963), 33(12), 3943-6, the disclosure of which is totally incorporated herein by reference, discloses that sulforhodamine B chloride heated 10-12 hours with $HOCH_2CH_2NH_2$ at 170-80°, then triturated with saturated NaCl gave, after solution in $CHCl_3$ and precipitation with petroleum ether, 80% red sulforhodamine B N(β-hydroxyethyl)amide; similar reaction with $HN(CH_2CH_2OH)_2$ gave 70% N,N-bis(β-hydroxyethyl)amide, a bright red wax. These treated with $SOCl_2$ in $CHCl_3$ gave, respectively, N-(β-chloroethyl)amide, a brown powder, and N,N-bis(β-chloroethyl)amide, a violet powder. Absorption spectra of the amides are shown. The (hydroxyethyl)amides displayed strong orange fluorescence in solution.

"Rhodamine Dyes and Related Compounds. VII. (β-Phenylethyl)rhodamines," I. S. Ioffe et al., *Zh. Obsch. Khim.* (1963), 33(4), 1089-92, the disclosure of which is totally incorporated herein by reference, discloses a process wherein heating dichlorofluoran with $PhCH_2CH_2NH_2$ or $PhCH_2CH(Me)NH_2$ in the presence of ZnO and $ZnCl_2$ for 5-6 hours at 220° gave, after heating for 2 hours with aqueous HCl, 96-8% crude products which, after crystallization from alc. HCl, gave red, powdery N,N'-bis(β-phenylethyl)rhodamine-HCl, m. 172-5°, or N,N'-bis(α-methyl-β-phenylethyl)rhodamine-HCl, m. 175-8°; N-phenyl-N'-(β-phenylethyl)rhodamine-HCl, m. 162-6°, was prepared from $PhCH_2CH_2NH_2$ and 3'-chloro-6'-anilinofluoran under the above conditions. Treated with alc. NaOH and quenched in $H_2O$, these hydrochlorides gave the free bases of the dyes as brown-red solids, which tended to form colloids in aqueous medium. The free bases m. 123-5°, decompd. 120°, and m. 164-8°, respectively. The ultraviolet and visible spectra of the dyes were similar to the spectra of dibenzylrhodamine, but had deeper color; strong fluorescence was shown by these dyes. The spectrum of the bis(β-phenylethyl)rhodamine was almost identical with that of diethylrhodamine.

"Rhodamine Dyes and Related Compounds. VI. Chloride and Amides of Sulforhodamine B," I. S. Ioffe et al., *Zh. Obsch. Khim.* (1962), 32, 1489-92, the disclosure of which is totally incorporated herein by reference, discloses that sulforhodamine B (5 g., dried at 125°) and 3 g. $PCl_5$ heated in 50 milliliters $CHCl_3$ for 4 hours, then extd. with cold $H_2O$ to remove excess $PCl_6$, gave, after concentration of the dried organic layer and treatment of the residue with much cold petroleum ether, the dark red p-sulfonyl chloride, $C_{27}H_{29}O_6N_2S_2Cl$, which slowly forms the original compound on contact with $H_2O$. With $NH_3$ in $CHCl_3$ it gave the corresponding p-sulfonamide, 81%, red-violet powder, sol. in EtOH or AcOH; similarly was prepared the p-sulfonanilide, brown-violet solid. These have absorption spectra similar to the original compound but with less intense absorption. The p-sulfonyl chloride has a more intense absorption than the amides.

"Rhodamine Dyes and Related Compounds. V. α-Pyridylrhodamine," I. S. Ioffe et al., *Zh. Obsch. Khim.* (1962), 32, 1485-9, the disclosure of which is totally incorporated herein by reference, discloses a process wherein heating 3,6-dichlorofluorane with 2-aminopyridine in the presence of $ZnCl_2$ for 3 hours at 160-80° gave, after extraction with hot $H_2O$ and EtOH and crystallization of the residue from aqueous $Me_2CO$, 3-chloro-6-α-pyridylaminofluorane-HCl, m. 280-2°; free base, m. 185-7°. This heated with 2-aminopyridine and $ZnCl_2$ at 250-60° for 6 hours, then precipitated from hot EtOH—HCl with $H_2O$, gave red N,N'-bis(α-pyridyl)rhodamine-HCl, m. 238-40°, also formed directly from dichlorofluorane and excess aminopyridine at 250-60°. Similarly, 3-chloro-6-anilino-fluorane gave red-violet N-phenyl-N'-α-pyridylrhodamine-HCl, m. 225-30°. All these were converted to N,N'-diphenylrhodamine by heating with $PhNH_2$ and $ZnCl_2$ for 3 hours at 180-200°. The absorption spectra of the products are shown; dipyridylrhodamine has a more intense color than other members of the group.

"Rhodamine Dyes and Related Compounds. IV. Aryl- and Benzylrhodamines," I. S. Ioffe et al., *Zh. Obsch. Khim.* (1962), 32, 1480-5, the disclosure of which is totally incorporated herein by reference, discloses a process wherein heating fluorescein chloride with $ArNH_2$ in the presence of $ZnCl_2$—ZnO for 4 to 5 hours at 210-20° gave, after leaching with hot dil. HCl, soln. of the residue in hot $PhNH_2$, and pptn. with dil. HCl, the following N,N'-diarylrhodamines which were isolated as HCl salts: Ph, m. 255-60°; o-$meC_6H_4$, m. 205-10°; m-$meC_6H_4$, m. 195-200°; p-$meC_6H_4$, m. 255-60°. $PhCH_2NH_2$ similarly gave N,N'-dibenzylrhodamine, m. 160-5°; HCl salt decomp. 160-5°; di-HCl salt decomp. 210°. $PhCH_2NH_2$ and 3-chloro-6-anilinofluorane gave 90-5% N-phenyl-N'-benzylrhodamine isolated as the HCl salt, m. 200-10°. The absorption spectra of these rhodamines are shown. Dibenzylrhodamine fluoresces strongly in solution, while the phenyl benzyl analog has a weak fluorescence. The benzyl groups cause a bathochromic shift of the absorption band in the substituted rhodamines; the diarylrhodamines form blue-violet solutions unlike the orange-yellow produced by unsubstituted rhodamine. The di-HCl salt of dibenzylrhodamine loses one HCl in soln. as shown by behavior in EtOH.

"Rhodamine Dyes and Related Compounds. III. Reaction of m-aminophenol With Phthalic Anhydride in Hot Sulfuric Acid," I. S. Ioffe et al., *Zh. Obsch. Khim.* (1962), 32, 1477-80, the disclosure of which is totally incorporated herein by reference, discloses that heating 25 g. of m-$H_2NC_6H_4OH$ with 20 g. o-$C_6H_4(CO)_2O$ in 100 milliliters concentrated $H_2SO_4$ at 160-200° for 2-8 hours was used to examine the effects of conditions of condensation on the reaction products. Rhodamine formation began at 170° and reached a max. (20%) in 2 hours at 190°. Rhodol was a constant byproduct as a result of partial deamination of rhodamine. The deamination is promoted by longer reaction time and higher temperatures. These factors also promoted the formation of a dark, amorphous material. o-Hydroxysulfanilic acid was formed in the reaction in up to 32% yield at 160° in 2 hours; more drastic conditions lowered its yield rapidly. Prior to the appearance of substantial amounts of rhodamine in the mixture, sulfonation of m-$H_2NC_6H_4OH$ takes place, and the resulting compound appears to be the intermediate which reacts, with this compound forming rhodamine by displacement of the sulfonic acid group. This was confirmed by reaction of o-$C_6H_4(CO)_2O$ with o-hydroxysulfanilic acid under the conditions shown above. m-Aminosalicylic acid also yields the same products in a mixture similar to that formed by m-$H_2NC_6H_4OH$.

"Rhodamine Dyes and Related Compounds. XVIII. N,N'-Dialkylrhodamines with Heavy Hydrocarbon Radicals," I. S. Ioffe et al., *Zh. Organ. Khim.* (1970), 6(2), 369-71, the disclosure of which is totally incorporated herein by reference, discloses a process wherein the condensation of I (X=Cl) with $RNH_2$ (R=$C_6H_{13}$, $C_8H_{17}$, $C_{16}H_{33}$, or $C_{18}H_{37}$) gave the title dyes (I, X=NHR) (II). The presence of alkyl groups in II did not change their color in comparison with II (R=H); all II absorbed strongly at 523-6 nm. However, long alkyl chains altered the hydrophobic properties of II as shown by the change of their partition coefficients in oil-alc. or kerosine-alc. systems with the length of R chain.

"Rhodamine Dyes and Related Compounds. XIX. Mutual Conversions of the Colorless and Colored Forms of N,N'-Substituted Rhodamines," I. S. Ioffe et al., *Zh. Organ. Khim.* (1972), 8(8), 1726-9, the disclosure of which is totally incorporated herein by reference, discloses that substituted rhodamines give colored solutions in polar and colorless solutions in nonpolar solvents. The solvent polarity at which the colorless lactone form is converted to the quinoid, internal salt form depends on the number and structure of alkyl, aryl, or H substituents. Absorption spectra of N,N'-diethylrhodamine in water-dioxane mixtures show how the light absorption increases when the solvent polarity (i.e., water amount in the mixture) is increased.

"Synthesis of N-Substituted Flaveosines, Acridine Analogs of Rhodamine Dyes," I. S. Ioffe et al., *Zh. Org. Khim.* (1966), 2(9), 1721, the disclosure of which is totally incorporated herein by reference, discloses that o-(3,6-chloro-9-acridinyl)benzoic acid heated with $BuNH_2$ or $Bu_2NH$ readily gave the hydrochlorides.

"Rhodamine Dyes and Related Compounds. XVII. Acridine Analogs of Rhodamine and Fluorescein," I. S. Ioffe et al., *Zh. Organ. Khim.* (1966), 2(5), 927-31, the disclosure of which is totally incorporated herein by reference, discloses absorption spectra for flaveosin, fluorescein, azafluorescein, their Et esters and diacetyl derivatives. Replacement of the xanthene structure by the acridine group changed the spectra of such dyes. Azafluorescein heated with $PCl_5$ at 95-100° gave o-(3,6-dichloro-9-acridinyl)-benzoic acid, decomp.>300°; its uv spectrum was similar to that of unsubstituted acridinylbenzoic acid. One of the flaveosin compounds heated with 25% $H_2SO_4$ in a sealed tube 10 hours at 200-20° gave azafluorescein, decomp.>380°; heated with EtOH—$H_2SO_4$ it gave one of the flaveosins, decomp.>300° $Ac_2O$—$H_2SO_4$ gave in 1 hour one of the flaveosins, decomp. 206°. The compound formed by treatment of 3,6-dichlorofluorane with $NH_3$ was prepared. Its uv spectrum is given.

"New Lipophilic Rhodamines and Their Application to Optical Potassium Sensing," T. Werner et al., *Journal of Fluorescence*, Vol. 2, No. 3, pp. 93-98 (1992), the disclosure of which is totally incorporated herein by reference, discloses the synthesis of new lipophilic fluorescent rhodamines directly from 3,6-dichlorofluoresceins and the respective long-chain amines with excellent solubility in lipids and lipophilic membranes. Spectrophotometric and luminescent properties of the dyes are reported and discussed with respect to their application in new optical ion sensors. One rhodamine was applied in a poly(vinyl chloride)-based sensor membrane for continuous and sensitive optical determination of potassium ion, using valinomycin as the neutral ion carrier.

U.S. Pat. No. 1,991,482 (Allemann), the disclosure of which is totally incorporated herein by reference, discloses a process of producing rhodamine dyes which comprises condensing a halogenated primary amine of the benzene series with fluorescein dichloride and sulfonating the condensed product.

U.S. Pat. No. 5,847,162 (Lee et al.), the disclosure of which is totally incorporated herein by reference, discloses a class of 4,7-dichlororhodamine compounds useful as fluorescent dyes having the structure

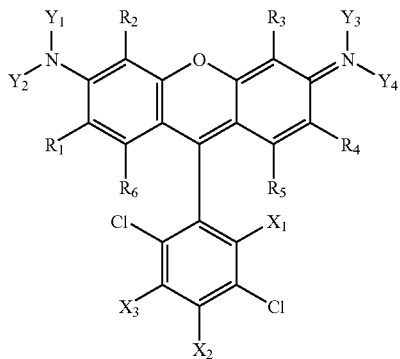
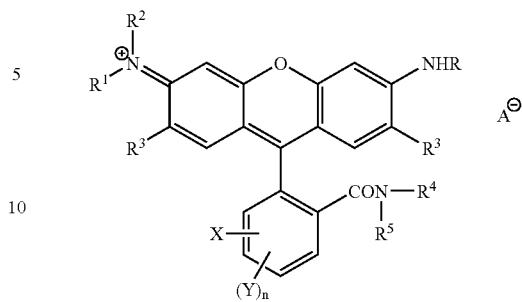

wherein $R_1$-$R_6$ are hydrogen, fluorine, chlorine, lower alkyl lower alkene, lower alkyne, sulfonate, sulfone, amino, amido, nitrile, lower alkoxy, lining group, or combinations thereof or, when taken together, $R_1$ and $R_6$ is benzo, or, when taken together, $R_4$ and $R_5$ is benzo; $Y_1$-$Y_4$ are hydrogen or lower alkyl or, when taken together, $Y_1$ and $R_2$ is propano and $Y_2$ and $R_1$ is propano, or, when taken together, $Y_3$ and $R_3$ is propano and $Y_4$ and $R_4$ is propano; and $X_1$-$X_3$ taken separately are selected from the group consisting of hydrogen, chlorine, fluorine, lower alkyl carboxylate, sulfonic acid, —CH$_2$OH, and linking group. In another aspect, the invention includes reagents labeled with the 4,7-dichlororhodamine dye compounds, including deoxynucleotides, dideoxynucleotides, and polynucleotides. In an additional aspect, the invention includes methods utilizing such dye compounds and reagents including dideoxy polynucleotide sequencing and fragment analysis methods.

U.S. Pat. No. 4,935,059 (Mayer et al.), the disclosure of which is totally incorporated herein by reference, discloses basic rhodamine dyes suitable for use in recording fluids for the ink jet process and for coloring paper stock having the formula where $A^-$ is an anion, R is hydrogen or unsubstituted or substituted alkyl or cycloalkyl, $R^1$ and $R^2$ independently of one another are each hydrogen or unsubstituted or substituted alkyl or cycloalkyl, or one of the radicals may furthermore be aryl, or $R^1$ and $R^2$, together with the nitrogen atom, form a saturated heterocyclic structure, the radicals $R^3$ independently of one another are each hydrogen or $C_1$-$C_4$-alkyl, $R^4$ and $R^5$ independently of one another are each unsubstituted or substituted alkyl or cycloalkyl, or one of the radicals may furthermore be hydrogen, aryl or hetaryl, $R^4$ and $R^5$, together with the nitrogen atom, form a saturated heterocyclic structure, n is 1, 2 or 3, X is hydrogen, chlorine, bromine, $C_1$-$C_4$-alkyl, $C_1$-$C_4$-alkoxy or nitro and Y is hydrogen or chlorine, are particularly useful for dyeing paper stocks.

U.S. Pat. No. 1,981,515 (Kyrides), the disclosure of which is totally incorporated herein by reference, discloses intermediates for rhodamine dyestuffs.

U.S. Pat. No. 1,981,516 (Kyrides), the disclosure of which is totally incorporated herein by reference, discloses intermediates for secondary alkylated rhodamine dyes.

British Patent Publication GB 421 737, the disclosure of which is totally incorporated herein by reference, discloses dyes of the rhodamine series which are prepared by condensing naphthalene-2:3-dicarboxylic acid with a m-aminophe-

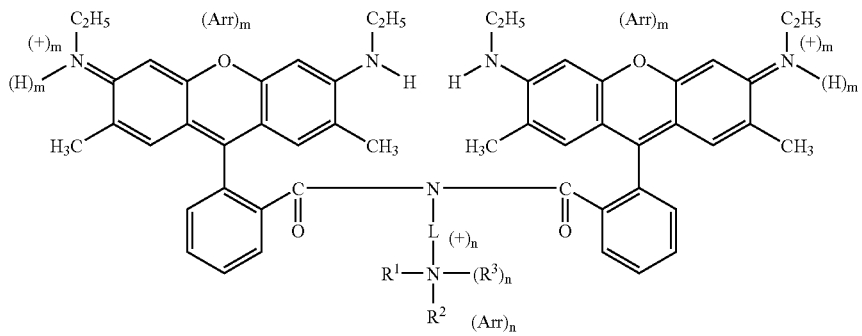

where L is $C_2$-$C_{10}$-alkylene, $R^1$, $R^2$, and $R^3$ are each independently of the others hydrogen, substituted or unsubstituted $C_1$-$C_{10}$-alkyl or $C_5$-$C_7$-cycloalkyl or $R^1$ and $R^2$ together with the nitrogen atom linking them together are a hetero cyclic radical, $An^-$ is one equivalent of an anion and m and n are each independently of the other 0 or 1.

U.S. Pat. No. 4,647,675 (Mayer et al.), the disclosure of which is totally incorporated herein by reference, discloses compounds of the general formula nol in which the nitrogen group is substituted by one or two alkyl groups, the products, if desired, being sulphonated. The unsulphonated products may be used as lake colouring matters whilst the sulphonated dyes are acid wool dyes. In examples, (1) naphthalene-2:3-dicarboxylic acid is condensed with diethyl-m-aminophenol in the presence of zinc chloride giving a product which dyes tannin-mordanted cotton in the same shade as Rhodamine B and a sulphonated product which dyes wool bluish-red shades; (2) monoethyl-m-aminophenol is used instead of the diethyl-m-aminophenol in example (1), yielding a dye, which when sulphonated dyes wool red-orange shades; (3) 2-ethylamino-p-cresol replaces the diethyl-m-aminophenol in example (1), yielding a dye dyeing and printing tannin-mordanted cotton in shades similar to Rhodamine 69BS and when sulphonated dyeing wool red.

Japanese Patent Publication JP 61221265, the disclosure of which is totally incorporated herein by reference, discloses rhodamine compounds of formula I

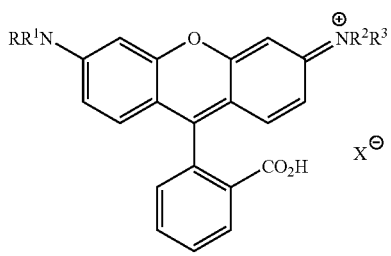

wherein $R_1$, $R_3$ are each lower alkyl; $R_2$ is lower alkyl, 10C or higher long-chain alkyl; $R_4$ is 10C or higher long-chain alkyl; $X^-$ is an anion, or squarylium compounds of formula II

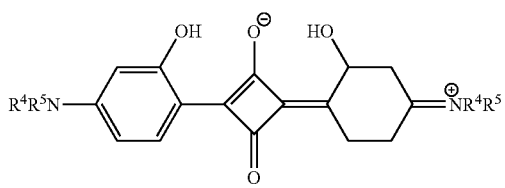

wherein $R_2$ is 10C or higher long-chain alkyl. Example: 3,6-(N,N'-diethyl-N,N'-dioctadecyl) diamino-9-(2-carboxyphenyl) xanthilium perchlorate. Use: materials for molecular electronics, which are suitable for use as materials for photoelectric converter, optical memory, etc. Preparation: 2-(4-N,N'-diethylamino-2-hydroxybenzoyl)-benzoic acid, which is a condensate between N-ethyl-N-octadecyl-m-hydroxyaniline and phthalic anhydride, is reacted with N-ethyl-N-octadecyl-m-hydroxyaniline to obtain the compound of formula I. 3-HOC$_6$H$_4$N(Et)(CH$_2$)$_{17}$Me and phthalic anhydride were heated at 150° for 4 hours, treated with aqueous NH$_3$, and the amorphous intermediate mixed with aqueous HClO$_4$ forming a compound of formula I (R=R$_2$=Et; R$_1$=R$_3$=C$_{18}$H$_{37}$; X=ClO$_4$), having $\lambda_{max}$ (MeOH) 550 nm.

U.S. Pat. No. 5,084,099 (Jaeger et al.), the disclosure of which is totally incorporated herein by reference, discloses modified phase change ink compatible colorants which comprise a phase change ink soluble complex of (a) a tertiary alkyl primary amine and (b) dye chromophores, i.e., materials that absorb light in the visible wavelength region to produce color having at least one pendant acid functional group in the free acid form (not the salt of that acid). These modified colorants are extremely useful in producing phase change inks when combined with a phase change ink carrier, even though the unmodified dye chromophores have limited solubility in the phase change ink carrier. Thin films of uniform thickness of the subject phase change ink compositions which employ the modified phase change ink colorants exhibit a high degree of lightness and chroma. The primary amine-dye chromophore complexes are soluble in the phase change ink carrier and exhibit excellent thermal stability.

U.S. Pat. No. 5,507,864 (Jaeger et al.), the disclosure of which is totally incorporated herein by reference, discloses a phase change ink composition that includes a combination of different dye types such as an anthraquinone dye and a xanthene dye, which is most preferably a rhodamine dye. While each dye type is insufficiently soluble with respect to favored carrier compositions to preserve color saturation in reduced ink quantity prints, the dye type combination permits increased dye loading and maintains print quality. In a preferred embodiment of the invention, a favored carrier composition is adjusted to promote the colored form of a preferred rhodamine dye (C.I. Solvent Red 49) and mixed with a preferred anthraquinone dye (C.I. Solvent Red 172) whose concentration is kept below a critical level to prevent post printed blooming. The resulting preferred phase change ink compositions provide a magenta phase change ink with enhanced light fastness and color saturation, as well as good compatibility with preferred existing subtractive primary color phase change inks.

U.S. Pat. No. 5,621,022 (Jaeger et al.), the disclosure of which is totally incorporated herein by reference, discloses a phase change ink composition wherein the ink composition utilizes polymeric dyes in combination with a selected phase change ink carrier composition.

U.S. Pat. No. 5,747,554 (Sacripante et al.), the disclosure of which is totally incorporated herein by reference, discloses an ink composition comprising a polyesterified-dye (I) or polyurethane-dye (II) with a viscosity of from about 3 centipoise to about 20 centipoise at a temperature of from about 125° C. to about 165° C. and represented by the formulas

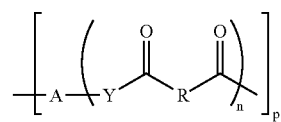

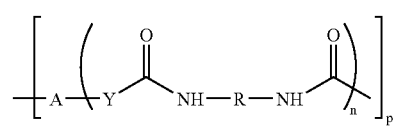

wherein A is an organic chromophore, Y is an oxyalkylene or poly(oxyalkylene), R is an arylene or alkylene, n represents the number of repeating segments, and is an integer of from about 2 to about 50, and p represents the number of chains per chromophore and is an integer of from about 1 to about 6.

U.S. Pat. No. 5,902,841 (Jaeger et al.), the disclosure of which is totally incorporated herein by reference, discloses a phase change ink composition wherein the ink composition utilizes colorant in combination with a selected phase change ink carrier composition containing at least one hydroxy-functional fatty amide compound.

European Patent Publication 0 565 798 (Shustack), the disclosure of which is totally incorporated herein by reference, discloses ultraviolet radiation-curable primary and secondary coating compositions for optical fibers. The primary coatings comprise a hydrocarbon polyol-based reactively terminated aliphatic urethane oligomer; a hydrocarbon monomer terminated with at least one end group capable of reacting with the terminus of the oligomer; and an optional photoinitiator. The secondary coatings comprise a polyester and/or polyether-based aliphatic urethane reactively terminated oligomer; a hydrocarbonaceous viscosity-adjusting component capable of reacting with the reactive terminus of (I); and an optional photoinitiator. Also disclosed are optical fibers coated with the secondary coating alone or with the primary and secondary coatings of the invention.

While known compositions and processes are suitable for their intended purposes, a need remains for new magenta colorant compositions. In addition, a need remains for magenta colorant compositions particularly suitable for use in phase change inks. Further, a need remains for magenta colorants with desirable thermal stability. Additionally, a need remains for magenta colorants that exhibit minimal undesirable discoloration when exposed to elevated temperatures. There is also a need for magenta colorants that exhibit a desirable brilliance. In addition, there is a need for magenta colorants that exhibit a desirable hue. Further, there is a need for magenta colorants that are of desirable chroma. Additionally, there is a need for magenta colorants that have desirably high lightfastness characteristics. A need also remains for magenta colorants that have a desirably pleasing color. In addition, a need remains for magenta colorants that exhibit desirable solubility characteristics in phase change ink carrier compositions. Further, a need remains for magenta colorants that enable phase change inks to be jetted at temperatures of over 135° C. while maintaining thermal stability. Additionally, a need remains for magenta colorants that enable phase change inks that generate images with low pile height. There is also a need for magenta colorants that enable phase change inks that generate images that approach lithographic thin image quality. In addition, there is a need for magenta colorants that exhibit oxidative stability. Further, there is a need for magenta colorants that do not precipitate from phase change ink carriers. Additionally, there is a need for magenta colorants that do not, when included in phase change inks, diffuse into adjacently printed inks of different colors. A need also remains for magenta colorants that do not leach from media such as phase change ink carriers into tape adhesives, paper, or the like. In addition, a need remains for magenta colorants that, when incorporated into phase change inks, do not lead to clogging of a phase change ink jet printhead. Further, there is a need for magenta colorants that enable phase change inks that generate images with sharp edges that remain sharp over time. Additionally, there is a need for magenta colorants that enable phase change inks that generate images which retain their high image quality in warm climates. Further, there is a need for magenta colorants that enable phase change inks that generate images of desirably high optical density. Additionally, there is a need for magenta colorants that, because of their good solubility in phase change ink carriers, enable the generation of images of low pile height without the loss of desirably high optical density. A need also remains for magenta colorants that enable cost-effective inks. In addition, a need remains for magenta colorants that are compounds having metal compounds associated with chromogens, wherein the thermal stability of the metal compound colorants exceeds that of the chromogens unassociated with a metal. Further, a need remains for magenta colorants that can be prepared by simpler methods. Additionally, a need remains for magenta colorants prepared from starting materials that are more easily handled.

SUMMARY

Disclosed herein are compounds of the formula

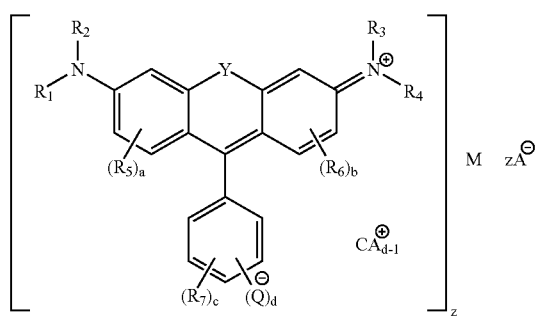

wherein M is either (1) a metal ion having a positive charge of +y wherein y is an integer which is at least 2, said metal ion being capable of forming a compound with at least two

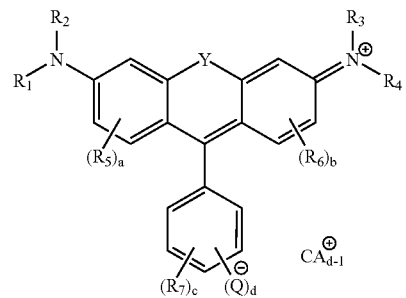

chromogen moieties, or (2) a metal-containing moiety capable of forming a compound with at least two

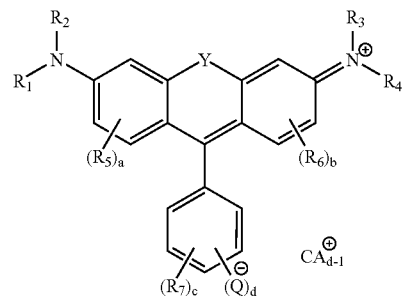

chromogen moieties, z is an integer representing the number of

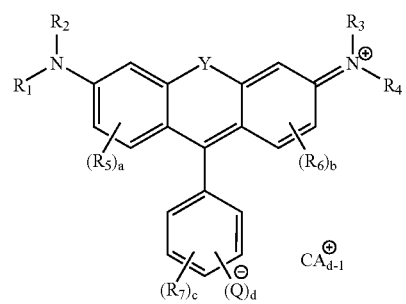

chromogen moieties associated with the metal and is at least 2, $R_1$, $R_2$, $R_3$, and $R_4$ each, independently of the others, is (i) a hydrogen atom, (ii) an alkyl group, (iii) an aryl group, (iv) an arylalkyl group, or (v) an alkylaryl group, wherein $R_1$ and $R_2$ can be joined together to form a ring, wherein $R_3$ and $R_4$ can be joined together to form a ring, and wherein $R_1$, $R_2$, $R_3$, and $R_4$ can each be joined to a phenyl ring in the central structure, a and b each, independently of the others, is an integer which is 0, 1, 2, or 3, c is an integer which is 0, 1, 2, 3, or 4, each $R_5$, $R_6$, and $R_7$, independently of the others, is (i) an alkyl group, (ii) an aryl group, (iii) an arylalkyl group, (iv) an alkylaryl group, (v) a halogen atom, (vi) an ester group, (vii) an amide group, (viii) a sulfone group, (ix) an amine group or ammonium group, (x) a nitrile group, (xi) a nitro group, (xii) a hydroxy group, (xiii) a cyano group, (xiv) a pyridine or pyridinium group, (xv) an ether group, (xvi) an aldehyde group, (xvii) a ketone group, (xviii) a carbonyl group, (xix) a thiocarbonyl group, (xx) a sulfate group, (xxi) a sulfide group, (xxii) a sulfoxide group, (xxiii) a phosphine or phosphonium group, (xxiv) a phosphate group, (xxv) a mercapto group, (xxvi) a nitroso group, (xxvii) an acyl group, (xxviii) an acid anhydride group, (xxix) an azide group, (xxx) an azo group, (xxxi) a cyanato group, (xxxii) an isocyanato group, (xxxiii) a thiocyanato group, (xxxiv) an isothiocyanato group, (xxxv) a urethane group, or (xxxvi) a urea group, wherein $R_5$, $R_6$, and $R_7$ can each be joined to a phenyl ring in the central structure,

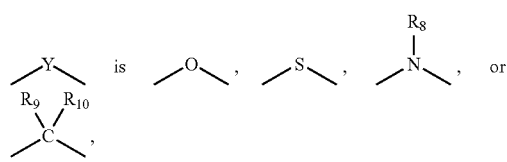

$R_8$, $R_9$, and $R_{10}$ each, independently of the others, is (i) a hydrogen atom, (ii) an alkyl group, (iii) an aryl group, (iv) an arylalkyl group, or (v) an alkylaryl group, provided that the number of carbon atoms in $R_1+R_2+R_3+R_4+R_5+R_6+R_7+R_8+R_9+R_{10}$ is at least about 16, $Q^-$ is a $COO^-$ group or a $SO_3^-$ group, d is an integer which is 1, 2, 3, 4, or 5, A is an organic anion, and CA is either a hydrogen atom or a cation associated with all but one of the $Q^-$ groups.

DETAILED DESCRIPTION

Disclosed herein are compounds of the formula

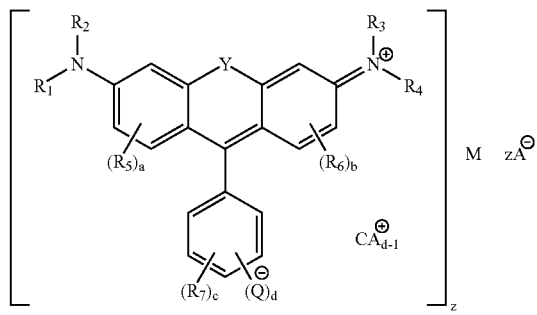

wherein M is either (1) a metal ion having a positive charge of +y wherein y is an integer which is at least 2, said metal ion being capable of forming a compound with at least two

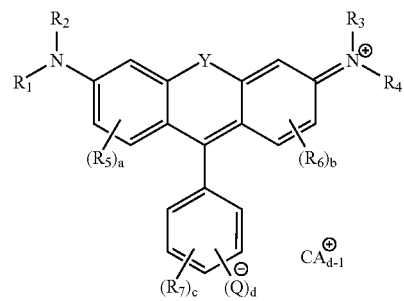

chromogen moieties, or (2) a metal-containing moiety capable of forming a compound with at least two

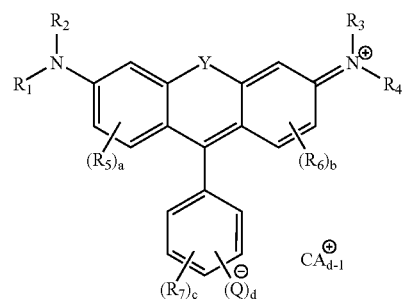

chromogen moieties, and z is an integer representing the number of

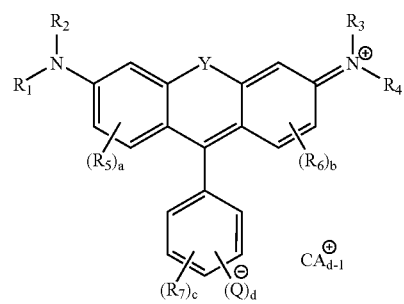

chromogen moieties associated with the metal and is at least 2. There is no necessary upper limit on the value of z.

Examples of metal cations having a positive charge of +y wherein y is an integer which is at least 2 include +2, +3, +4, and higher cations of magnesium, calcium, strontium, barium, radium, aluminum, gallium, germanium, indium, tin, antimony, tellurium, thallium, lead, bismuth, polonium, scandium, titanium, vanadium, chromium, manganese, iron, cobalt, nickel, copper, zinc, zirconium, niobium molybdenum, technetium, ruthenium, rhodium, palladium, silver, cadmium, hafnium, tantalum, tungsten, rhenium, osmium, iridium, platinum, gold, mercury, metals of the lanthanide series, such as europium and the like, metals of the actinide series, and the like.

Examples of metal-containing moieties include:

metal ionic moieties, such as $Me^{3+}X^-$ wherein Me represents a trivalent metal atom and X represents a monovalent anion, such as $Cl^-$, $Br^-$, $I^-$, $HSO_4^-$, $HSO_3^-$, $CH_3SO_3^-$, $CH_3C_6H_4SO_3^-$, $NO_3^-$, $HCOO^-$, $CH_3COO^-$, $H_2PO_4^-$, $SCN^-$, $BF_4^-$, $ClO_4^-$, $SSO_3^-$, $PF_6^-$, $SbCl_6^-$, or the like, or $Me^{4+}X^-$ or $Me^{4+}X^-$ or $Me^{4+}X_2^-$ wherein Me represents a tetravalent metal atom, X represents a monovalent anion, and $X_2$ represents 2 monovalent anions, $Me^{4+}X^{2-}$ wherein Me represents a tetravalent metal atom and $X^{2-}$ represents a divalent anion, and the like;

metal coordination compounds, wherein metals such as magnesium, calcium, strontium, barium, radium, aluminum, gallium, germanium, indium, tin, antimony, tellurium, thallium, lead, bismuth, polonium, scandium, titanium, vanadium, chromium, manganese, iron, cobalt, nickel, copper, zinc, zirconium, niobium molybdenum, technetium, ruthenium, rhodium, palladium, silver, cadmium, hafnium, tantalum, tungsten, rhenium, osmium, iridium, platinum, gold, mercury, metals of the lanthanide series, such as europium and the like, metals of the actinide series, and the like are associated with one or more ligands, such as carbonyl (carbon monoxide) ligands, ferrocene ligands, halide ligands, such as fluoride, chloride, bromide, iodide, or the like, amine ligands of the formula

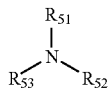

wherein $R_{51}$, $R_{52}$, and $R_{53}$ each, independently of the others, is (i) a hydrogen atom, (ii) a halogen atom, such as fluorine, chlorine, bromine, iodine, or the like, (iii) an alkyl group (including linear, branched, saturated, unsaturated, cyclic, substituted, and unsubstituted alkyl groups, and wherein hetero atoms, such as oxygen, nitrogen, sulfur, silicon, phosphorus, and the like either may or may not be present in the alkyl group), in one embodiment with at least 1 carbon atom, and in one embodiment with no more than about 55 carbon atoms, in another embodiment with no more than about 30 carbon atoms, and in yet another embodiment with no more than about 20 carbon atoms, although the number of carbon atoms can be outside of these ranges, (iv) an aryl group (including unsubstituted and substituted aryl groups, and wherein hetero atoms, such as oxygen, nitrogen, sulfur, silicon, phosphorus, and the like either may or may not be present in the aryl group), in one embodiment with at least about 6 carbon atoms, and in one embodiment with no more than about 26 carbon atoms, in another embodiment with no more than about 22 carbon atoms, and in yet another embodiment with no more than about 18 carbon atoms, although the number of carbon atoms can be outside of these ranges, (v) an arylalkyl group (including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the arylalkyl group), in one embodiment with at least about 7 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as benzyl or the like, or (vi) an alkylaryl group (including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the alkylaryl group), in one embodiment with at least about 7 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as tolyl or the like, wherein one or more of $R_{51}$, $R_{52}$, and $R_{53}$ can be joined together to form a ring, and wherein the substituents on the substituted alkyl, aryl, arylalkyl, and alkylaryl groups can be (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring, with specific examples of suitable amine ligands-including ammonia, trimethylamine, ethylenediamine, bipyridine, and the like, phosphine ligands of the formula

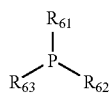

wherein $R_{61}$, $R_{62}$, and $R_{63}$ each, independently of the others, is (i) a hydrogen atom, (ii) a halogen atom, such as fluorine, chlorine, bromine, iodine, or the like, (iii) an alkyl group (including linear, branched, saturated, unsaturated, cyclic, substituted, and unsubstituted alkyl groups, and wherein hetero atoms, such as oxygen, nitrogen, sulfur, silicon, phosphorus, and the like either may or may not be present in the alkyl group), in one embodiment with at least 1 carbon atom, and in one embodiment with no more than about 55 carbon atoms, in another embodiment with no more than about 30 carbon atoms, and in yet another embodiment with no more than about 20 carbon atoms, although the number of carbon atoms can be outside of these ranges, (iv) an aryl group (including unsubstituted and substituted aryl groups, and wherein hetero atoms, such as oxygen, nitrogen, sulfur, silicon, phosphorus, and the like either may or may not be present in the aryl group), in one embodiment with at least about 6 carbon atoms, and in one embodiment with no more than about 26 carbon atoms, in another embodiment with no more than about 22 carbon atoms, and in yet another embodiment with no more than about 18 carbon atoms, although the number of carbon atoms can be outside of these ranges, (v) an arylalkyl group (including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the arylalkyl group), in one embodiment with at least about 7 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as benzyl or the like, (vi) an alkylaryl group (including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the alkylaryl group), in one embodiment with at least about 7 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as tolyl or the like, (vii) an alkoxy group (including linear, branched, saturated, unsaturated, cyclic, substituted, and unsubstituted alkoxy groups, and wherein hetero atoms, such as oxygen, nitrogen, sulfur, silicon, phosphorus, and the like either may or may not be present in the alkoxy group), in one embodiment with at least 1 carbon atom, and in one embodiment with no more than about 55 carbon atoms, in another embodiment with no more than about 30 carbon atoms, and in yet another embodiment with no more than about 20 carbon atoms, although the number of carbon atoms can be outside of these ranges, (viii) an aryloxy group (including unsubstituted and substituted aryloxy groups, and wherein hetero atoms, such as oxygen, nitrogen, sulfur, silicon, phosphorus, and the like either may or may not be present in the aryloxy group), in one embodiment with at least about 6 carbon atoms, and in one embodiment with no more than about 26 carbon atoms, in another embodiment with no more than about 22 carbon atoms, and in yet another embodiment with no more than about 18 carbon atoms, although the number of carbon atoms can be outside of these ranges, (ix) an arylalkyloxy group (including unsubstituted and substituted arylalkyloxy groups, wherein the alkyl portion of the arylalkyloxy group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the arylalkyloxy group), in one embodiment with at least about 7 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as benzyloxy or the like, or (x) an alkylaryloxy group (including unsubstituted and substituted alkylaryloxy groups, wherein the alkyl portion of the alkylaryloxy group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the alkylaryloxy group), in one embodiment with at least about 7 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as tolyloxy or the like, wherein one or more of $R_{61}$, $R_{62}$, and $R_{63}$ can be joined together to form a ring, and wherein the substituents on the substituted alkyl, alkoxy, aryl, aryloxy, arylalkyl, arylalkyloxy, alkylaryl, and alkylaryloxy groups can be (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring, with specific examples of suitable phosphine ligands including phosphine, trifluorophosphine, trichlorophosphine, trimethylphosphine, triphenylphosphine, trethoxyphosphine, and the like, water ligands, cyano ligands, isocyano ligands, hydroxide anions, nitro ligands, nitrito ligands, thiocyanato ligands, nitric oxide ligands, and the like, including monodentate ligands, bidentate ligands, tridentate ligands, tetradentate ligands, pentadentate ligands, hexadentate ligands (such as ethylene diamine tetraacetic acid), bridging ligands joining two or more metal atoms in a complex, crown ether ligands, and the like; a wide variety of ligands and metal complexes are disclosed in, for example, *Advanced Inorganic Chemistry*, Fourth Edition, F. A. Cotton and G. Wilkinson, John Wiley & Sons (1980), the disclosure of which is totally incorporated herein by reference;

heteropolyacids, also known as polyoxometalates, which are acids comprising inorganic metal-oxygen clusters; these materials are discussed in, for example, "Polyoxometalate Chemistry: An Old Field with New Dimensions in Several Disciplines," M. T. Pope et al., *Angew. Chem. Int. Ed. Engl.*, Vol. 30, p. 34 (1991), the disclosure of which is totally incorporated herein by reference; examples of heteropolyacids include phosphotungstic acids, including (but not limited to) those of the general formula $H_3PO_4.12WO_3.XH_2O$ (wherein X is variable, with common values including (but not being limited to) 12, 24, or the like), silicotungstic acids, including (but not limited to) those of the general formula $H_4SiO_2.12WO_3.XH_2O$ (wherein X is variable, with common values including (but not being limited to) 12, 24, 26, or the like), phosphomolybdic acids, including (but not limited to) those of the general formula $12MoO_3.H_3PO_4.XH_2O$ (wherein X is variable, with common values including (but not being limited to) 12, 24, 26, or the like) and the like, all commercially available from, for example, Aldrich Chemical Co., Milwaukee, Wis., as well as mixtures thereof;

and any other metal-containing moiety capable of forming a compound with at least two

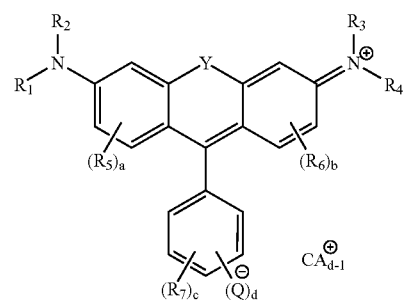

moieties.

By "capable of forming a compound with at least two

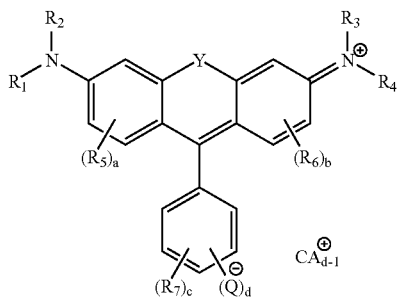

chromogen moieties" is meant that the metal cation or metal-containing moiety can react with two or more

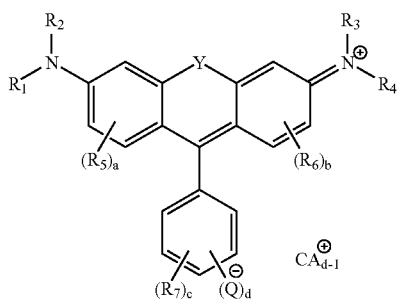

chromogen moieties to form a compound. Any kind of association between the

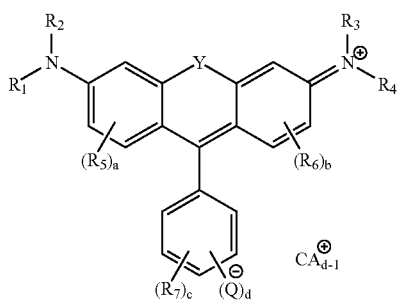

chromogen moiety and the metal cation or metal-containing moiety to form a compound is suitable, including ionic compounds, covalent compounds, coordination compounds, and the like.

$R_1$, $R_2$, $R_3$, and $R_4$ each, independently of the others, is (i) a hydrogen atom, (ii) an alkyl group (including linear, branched, saturated, unsaturated, cyclic, substituted, and unsubstituted alkyl groups, and wherein hetero atoms, such as oxygen, nitrogen, sulfur, silicon, phosphorus, and the like either may or may not be present in the alkyl group), in one embodiment with at least 1 carbon atom, in another embodiment with at least about 2 carbon atoms, in yet another embodiment with at least about 6 carbon atoms, in another embodiment with at least about 8 carbon atoms, and in yet another embodiment with at least about 18 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, (iii) an aryl group (including unsubstituted and substituted aryl groups, and wherein hetero atoms, such as oxygen, nitrogen, sulfur, silicon, phosphorus, and the like either may or may not be present in the aryl group), in one embodiment with at least about 6 carbon atoms, in another embodiment with at least about 10 carbon atoms, and in yet another embodiment with at least about 14 carbon atoms, and in one embodiment with no more than about 26 carbon atoms, in another embodiment with no more than about 22 carbon atoms, and in yet another embodiment with no more than about 18 carbon atoms, although the number of carbon atoms can be outside of these ranges, (iv) an arylalkyl group (including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the arylalkyl group), in one embodiment with at least about 7 carbon atoms, in another embodiment with at least about 12 carbon atoms, and in yet another embodiment with at least about 18 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as benzyl or the like, or (v) an alkylaryl group (including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the alkylaryl group), in one embodiment with at least about 7 carbon atoms, in another embodiment with at least about 12 carbon atoms, and in yet another embodiment with at least about 18 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as tolyl or the like, wherein $R_1$ and $R_2$ can be joined together to form a ring, wherein $R_3$ and $R_4$ can be joined together to form a ring, and wherein $R_1$, $R_2$, $R_3$, and $R_4$ can each be joined to a phenyl ring in the central structure, a and b each, independently of the others, is an integer which is 0, 1, 2, or 3, c is an integer which is 0, 1, 2, 3, or 4, each $R_5$, $R_6$, and $R_7$, independently of the others, is (i) an alkyl group (including linear, branched, saturated, unsaturated, cyclic, substituted, and unsubstituted alkyl groups, and wherein hetero atoms, such as oxygen, nitrogen, sulfur, silicon, phosphorus, and the like either may or may not be present in the alkyl group), in one embodiment with at least 1 carbon atom, and in one embodiment with no more than about 50 carbon atoms, in another embodiment with no more than about 30 carbon atoms, and in yet another embodiment with no more than about 18 carbon atoms, although the number of carbon atoms can be outside of these ranges, (ii) an aryl group (including unsubstituted and substituted aryl groups, and wherein hetero atoms, such as oxygen, nitrogen, sulfur, silicon, phosphorus, and the like either may or may not be present in the aryl group), in one embodiment with at least about 6 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges, (iii) an arylalkyl group (including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the arylalkyl group), in one embodiment with at least about 7 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges, such as benzyl or the like, (iv) an alkylaryl group (including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the alkylaryl group), in one embodiment with at least about 7 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges, such as tolyl or the like, (v) a halogen atom, such as fluorine, chlorine, bromine, iodine, or the like, (vi) an ester group, (vii) an amide group, (viii) a sulfone group, (ix) an amine group or ammonium group, (x) a nitrile group, (xi) a nitro group, (xii) a hydroxy group, (xiii) a cyano group, (xiv) a pyridine or pyridinium group, (xv) an ether group, (xvi) an aldehyde group, (xvii) a ketone group, (xviii) a carbonyl group, (xix) a thiocarbonyl group, (xx) a sulfate group, (xxi) a sulfide group, (xxii) a sulfoxide group, (xxiii) a phosphine or phosphonium group, (xxiv) a phosphate group, (xxv) a mercapto group, (xxvi) a nitroso group, (xxvii) an acyl group, (xxviii) an acid anhydride group, (xxix) an azide group, (xxx) an azo group, (xxxi) a cyanato group, (xxxii) an isocyanato group, (xxxiii) a thiocyanato group, (xxxiv) an isothiocyanato group, (xxxv) a urethane group, or (xxxvi) a urea group, wherein $R_5$, $R_6$, and $R_7$ can each be joined to a phenyl ring in the central structure,

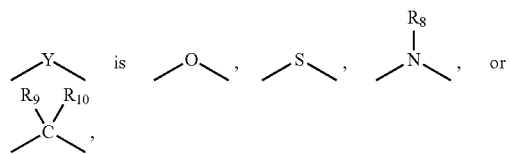

$R_8$, $R_9$, and $R_{10}$ each, independently of the others, is (i) a hydrogen atom, (ii) an alkyl group (including linear, branched, saturated, unsaturated, cyclic, substituted, and unsubstituted alkyl groups, and wherein hetero atoms, such as oxygen, nitrogen, sulfur, silicon, phosphorus, and the like either may or may not be present in the alkyl group), in one embodiment with at least 1 carbon atom, in another embodiment with at least about 2 carbon atoms, in yet another embodiment with at least about 6 carbon atoms, in another embodiment with at least about 8 carbon atoms, and in yet another embodiment with at least about 18 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, (iii) an aryl group (including unsubstituted and substituted aryl groups, and wherein hetero atoms, such as oxygen, nitrogen, sulfur, silicon, phosphorus, and the like either may or may not be present in the aryl group), in one embodiment with at least about 6 carbon atoms, in another embodiment with at least about 10 carbon atoms, and in yet another embodiment with at least about 14 carbon atoms, and in one embodiment with no more than about 26 carbon atoms, in another embodiment with no more than about 22 carbon atoms, and in yet another embodiment with no more than about 18 carbon atoms, although the number of carbon atoms can be outside of these ranges, (iv) an arylalkyl group (including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the arylalkyl group), in one embodiment with at least about 7 carbon atoms, in another embodiment with at least about 12 carbon atoms, and in yet another embodiment with at least about 18 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as benzyl or the like, or (v) an alkylaryl group (including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the alkylaryl group), in one embodiment with at least about 7 carbon atoms, in another embodiment with at least about 12 carbon atoms, and in yet another embodiment with at least about 18 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as tolyl or the like, provided that the number of carbon atoms in $R_1+R_2+R_3+R_4+R_5+R_6+R_7+R_8+R_9+R_{10}$ is in one embodiment at least about 16, in another embodiment at least about 18, in yet another embodiment at least about 20, in still another embodiment at least about 22, in another embodiment at least about 24, in yet another embodiment at least about 26, in still another embodiment at least about 28, in another embodiment at least about 30, in yet another embodiment at least about 32, in still another embodiment at least about 34, in another embodiment at least about 36, in yet another embodiment at least about 38, in still another embodiment at least about 40, in another embodiment at least about 42, in yet another embodiment at least about 44, in still another embodiment at least about 46, in another embodiment at least about 48, in yet another embodiment at least about 50, in still another embodiment at least about 52, in another embodiment at least about 54, in yet another embodiment at least about 56, in still another embodiment at least about 58, in another embodiment at least about 60, in yet another embodiment at least about 62, in still another embodiment at least about 64, in another embodiment at least about 66, in yet another embodiment at least about 68, in still another embodiment at least about 70, and in another embodiment at least about 72, each $Q^-$, independently of the others, is a $COO^-$ group or a $SO_3^-$ group, d is an integer which is 1, 2, 3, 4, or 5, and CA is either a hydrogen atom or a cation associated with all but one of the Q⁻ groups, with examples of suitable cations including (but not being limited to) alkali metal cations, such as $Li^+$, $Na^+$, $K^+$, $Rb^+$, and $Cs^+$, nonpolymeric or monomeric ammonium and quaternary amine cations, including those of the general formula

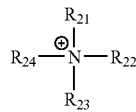

wherein each of $R_{21}$, $R_{22}$, $R_{23}$, and $R_{24}$, independently of the others, is (i) a hydrogen atom, (ii) an alkyl group (including linear, branched, saturated, unsaturated, cyclic, substituted, and unsubstituted alkyl groups, and wherein hetero atoms, such as oxygen, nitrogen, sulfur, silicon, phosphorus, and the like either may or may not be present in the alkyl group), in one embodiment with at least 1 carbon atom, in another embodiment with at least about 2 carbon atoms, in yet another embodiment with at least about 6 carbon atoms, in another embodiment with at least about 8 carbon atoms, and in yet another embodiment with at least about 18 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, (iii) an aryl group (including unsubstituted and substituted aryl groups, and wherein hetero atoms, such as oxygen, nitrogen, sulfur, silicon, phosphorus, and the like either may or may not be present in the aryl group), in one embodiment with at least about 6 carbon atoms, in another embodiment with at least about 10 carbon atoms, and in yet another embodiment with at least about 14 carbon atoms, and in one embodiment with no more than about 26 carbon atoms, in another embodiment with no more than about 22 carbon atoms, and in yet another embodiment with no more than about 18 carbon atoms, although the number of carbon atoms can be outside of these ranges, (iv) an arylalkyl group (including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the arylalkyl group), in one embodiment with at least about 7 carbon atoms, in another embodiment with at least about 12 carbon atoms, and in yet another embodiment with at least about 18 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as benzyl or the like, or (v) an alkylaryl group (including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the alkylaryl group), in one embodiment with at least about 7 carbon atoms, in another embodiment with at least about 12 carbon atoms, and in yet another embodiment with at least about 18 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as tolyl or the like, wherein one or more of $R_{21}$, $R_{22}$, $R_{23}$, and $R_{24}$ can be joined together to form a ring, and wherein the substituents on the substituted alkyl, aryl, arylalkyl, and alkylaryl groups can be (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring, oligomeric and polymeric cations, such as cationic polymers or oligomers, and the like, as well as mixtures thereof.

A is an organic anion. The organic anion can be monomeric, oligomeric, polymeric, or the like. Examples of monomeric organic anions include those of the formula $R_{20}$-$(An)_q$ wherein q is an integer of 1, 2, 3, 4, 5, or 6, each An, independently of the others, is a carboxylate group (COO—) or a sulfonate group (SO₃—), and $R_{20}$ is an alkyl (when q is 1) or alkylene (when q is 2, 3, 4, 5, or 6) group (including linear, branched, saturated, unsaturated, cyclic, substituted, and unsubstituted alkyl and alkylene groups, and wherein hetero atoms, such as oxygen, nitrogen, sulfur, silicon, phosphorus, and the like either may or may not be present in the alkyl or alkylene group), in one embodiment with at least 1 carbon atom, and in one embodiment with no more than about 100 carbon atoms, in another embodiment with no more than about 36 carbon atoms, and in yet another embodiment with no more than about 18 carbon atoms, although the number of carbon atoms can be outside of these ranges, an aryl (when q is 1) or arylene (when q is 2, 3, 4, 5, or 6) group (including unsubstituted and substituted aryl and arylene groups, and wherein hetero atoms, such as oxygen, nitrogen, sulfur, silicon, phosphorus, and the like either may or may not be present in the aryl or arylene group), in one embodiment with at least about 6 carbon atoms, and in one embodiment with no more than about 100 carbon atoms, in another embodiment with no more than about 36 carbon atoms, and in yet another embodiment with no more than about 18 carbon atoms, although the number of carbon atoms can be outside of these ranges, an arylalkyl (when q is 1) or arylalkylene (when q is 2, 3, 4, 5, or 6) group (including unsubstituted and substituted arylalkyl or arylalkylene groups, wherein the alkyl portion of the arylalkyl or arylalkylene group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the arylalkyl or arylalkylene group), in one embodiment with at least about 7 carbon atoms, and in one embodiment with no more than about 100 carbon atoms, in another embodiment with no more than about 36 carbon atoms, and in yet another embodiment with no more than about 18 carbon atoms, although the number of carbon atoms can be outside of these ranges, or an alkylaryl (when q is 1) or alkylarylene (when q is 2, 3, 4, 5, or 6) group (including unsubstituted and substituted alkylaryl or alkylarylene groups, wherein the alkyl portion of the alkylaryl or alkylarylene group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the alkylaryl or alkylarylene group), in one embodiment with at least about 7 carbon atoms, and in one embodiment with no more than about 100 carbon atoms, in another embodiment with no more than about 36 carbon atoms, and in yet another embodiment with no more than about 18 carbon atoms, although the number of carbon atoms can be outside of these ranges, and wherein the substituents on the substituted alkyl, alkylene, aryl, arylene, arylalkyl, arylalkylene, alkylaryl, and alkylarylene groups can be (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring.

Examples of suitable monomeric anions include monocarboxylic acid derived anions, such as acetate ($CH_3COO^-$), propionate ($CH_3CH_2COO^-$), butyrate ($CH_3(CH_2)_2COO^-$), valerate ($CH_3(CH_2)_3COO^-$), hexanoate ($CH_3(CH_2)_4COO^-$), heptanoate ($CH_3(CH_2)_5COO^-$), octanoate ($CH_3(CH_2)_6COO^-$), nonanoate ($CH_3(CH_2)_7COO^-$) decanoate ($CH_3(CH_2)_8COO^-$), undecanoate ($CH_3(CH_2)_9COO^-$), laurate ($CH_3(CH_2)_{10}COO^-$), tridecanoate ($CH_3(CH_2)_{11}COO^-$), myristate ($CH_3(CH_2)_{12}COO^-$), pentadecanoate ($CH_3(CH_2)_{13}COO^-$), palmitate ($CH_3(CH_2)_{14}COO^-$), heptadecanoateq ($CH_3(CH_2)_{15}COO^-$), stearate ($CH_3(CH_2)_{16}COO^-$), nonadecanoate ($CH_3(CH_2)_{17}COO^-$), eicosanoate ($CH_3(CH_2)_{18}COO^-$), heneicosanoate ($CH_3(CH_2)_{19}COO^-$), docosanoate ($CH_3(CH_2)_{20}COO^-$), tricosanoate ($CH_3(CH_2)_{21}COO^-$), tetracosanoate ($CH_3(CH_2)_{22}COO^-$), hexacosanoate ($CH_3(CH_2)_{24}COO^-$), heptacosanoate ($CH_3(CH_2)_{25}COO^-$), octacosanoate ($CH_3(CH_2)_{26}COO^-$), triacontanoate ($CH_3(CH_2)_{28}COO^-$), acetylacetonate, isobutyrate, ethylbutyrate, trimethylacetate, 2-methylbutyrate, isovalerate, 2,2-dimethylbutyrate, tert-butylacetate, 2-methylvalerate, 2,2,6,6-tetramethyl-3,5-heptanedionate, 2-propylpentanoate, 3-methylvalerate, 4-methylvalerate, 2-methylhexanoate, 2-ethylhexanoate, pyruvate, 2-ketobutyrate, 3-methyl-2-oxobutanoate, 2-oxopentanoate, 3-methyl-2-oxopentanoate, 4-methyl-2-oxopentanoate, 2-oxohexanoic acid, 3-fluoropyruvate, 4-methylthio-2-oxobutyrate, acrylate, methacrylate, crotonate, vinylacetate, tiglate, 3,3-dimethylacrylate, trans-2-pentenoate, 4-pentenoate, trans-2-methyl-2-pentenoate, 2,2-dimethyl-4-pentenoate, trans-2-hexenoate, trans-3-hexenoate, 2-ethyl-2-hexenoate, 6-heptenoate, 2-octenoate, citronellate, undecylenate, myristoleate, palmitoleate, oleate, elaidate, 11-eicosenoate, erucate, nervonate, chloroacetate, bromoacetate, iodoacetate, difluoroacetate, dichloroacetate, dibromoacetate, trifluoroacetate, chlorodifluoroacetate, trichloroacetate, tribromoacetate, 2-chloropropionate, 3-chloropropionate, 2-bromopropionate, 3-bromopropionate, 2-iodopropionate, 3-iodopropionate, 2,2-dichloropropionate, 2,3-dibromopropionate, pentafluoropropionate, 2-bromo-2-methylpropionate, 3-bromo-2-(bromomethyl)-propionate, 3-chloropivalate, 3,3-dichloropivalate, 4-chlorobutyrate, 2-bromobutyrate, 4-bromobutyrate, heptafluorobutyrate, 2-bromo-3-methylbutyrate, 5-chlorovalerate, 2-bromovalerate, 5-bromovalerate, nonafluoropentanoate, 2-bromohexanoate, 6-bromohexanoate, tridecafluoroheptanoate, 2-bromooctanoate, 8-bromooctanoate, pentadecafluorooctanoate, heptadecafluorononanoate, nonadecafluorodecanoate, 11-bromoundecanoate, 12-bromododecanoate, perfluorododecanoate, 2-bromotetradecanoate, 2-bromohexadecanoate, 3-chloroacrylate, 2-bromoacrylate, 2-(trifluoromethyl)acrylate, 2-(bromomethyl)acrylate, 4,4,4-trifluoro-3-methyl-2-butenoate, methoxyacetate, ethoxyacetate, 3-methoxypropionate, 2-(2-methoxyethoxy)acetate, 2-(2-(methoxyethoxy)ethoxy) acetate, tetrahydro-2-furoate, tetrahydro-3-furoate, 2,3,4,6-di-O-isopropylidene-2-ketogluconate, 3-nitropropionate, 6-nitrocaproate, 12-nitrododecanoate, levulinate, 4-acetylbutyrate, 6-oxoheptanoate, 7-oxooctanoate, 4,6-dioxoheptanoate, 3,4-dihydro-2,2-dimethyl-4-oxo-2H-pyran-6-carboxylate, cyclopentanecarboxylate, cyclopentylacetate, 3-cyclopentylpropionate, 3-methyl-2-(nitromethyl)-5-oxocyclopentaneacetate, 6,6,7,7,8,8,8-heptafluoro-2,2-dimethyl-3,5,-octanedionate, cyclohexanecarboxylate, cyclohexylacetate, dicyclohexylacetate, cyclohexanepropionate, cyclohexanebutyrate, cyclohexanepentanoate, 1-methyl-1-cyclohexanecarboxylate, 2-methyl-1-cyclohexanecarboxylate, 3-methyl-1-cyclohexanecarboxylate, 4-methyl-1-cyclohexanecarboxylate, 4-tert-butylcyclohexanecarboxylate, 4-pentylcyclohexanecarboxylate, 4-methylcyclohexaneacetate, 3-methoxycyclohexanecarboxylate, 4-methoxycyclohexanecarboxylate, cyclohexanecarboxylate, 2-norbornaneacetate, 4-pentylbicyclo(2.2.2)octane-1-carboxylate, 3-oxotricyclo(2.2.1.0(2,6)) -heptane-1-carboxylate, 3-noradamantanecarboxylate, 1-adamantanecarboxylate, 1-adamantaneacetate, 1-cyclopentene-1-carboxylate, 2-cyclopentene-1-acetate, 1-cyclohexene-1-carboxylate, 1-methyl-2-cyclohexene-1-carboxylate,

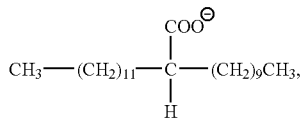

1,4-dihydro-2-methylbenzoate, retinoate, ketopinate, abietate, phenylacetate, 1-phenyl-1-cyclopentanecarboxylate, alpha-phenylcyclopentaneacetate, diphenylacetate, triphenylacetate, 2-phenylpropionate, hydrocinnamate, alpha-methylhydrocinnamate, alpha-(tert-butyl)hydrocinnamate, 2,2-diphenylpropionate, 3,3-diphenylpropionate, 3,3,3-triphenylpropionate, 2-phenylbutyrate, 3-phenylbutyrate, 4-phenylbutyrate, 5-phenylvalerate, 3-methyl-2-phenylvalerate, 6-phenylhexanoate, alpha-fluorophenylacetate, alpha-bromophenylacetate, alpha-methoxyphenylacetate, phenoxyacetate, alpha,beta-dibromohydrocinnamate, 3-phenoxypropionate, 2-phenoxypropionate, 11-phenoxyundecanoate, 2-phenoxybutyrate, alpha-methoxy-alpha-(trifluoromethyl)phenylacetate, (phenylthio)acetate, 3-(phenylthio)acrylate, benzylthioglycolate, 2-ethylthio-2,2-diphenylacetate, 3-benzoylpropionate, 2-methyl-4-oxo-4-phenylbutyrate, 4-benzoylbutyrate, o-tolylacetate, 3-oxo-1-indancarboxylate, 1,2,3,4-tetrahydro-2-naphthoate, (alpha, alpha,alpha-trifluoro-o-tolyl)acetate, 2-fluorophenylacetate, 2-chlorophenylacetate, 2-bromophenylacetate, 2-iodophenylacetate, 2-(2-chlorophenoxy)propionate, 2-methoxyphenylacetate, 3-(2-methoxyphenyl)propionate, 2-nitrophenylacetate, 2-formylphenoxyacetate, m-tolylacetate, 3-fluorophenylacetate, 3-chlorophenylacetate, 3-bromophenylacetate, 2-(3-chlorophenoxy)propionate, (alpha,alpha,alpha-trifluoro-m-tolyl)acetate, 3-methoxyphenylacetate, 3-nitrophenylacetate, p-tolylacetate, 3-(p-tolyl)propionate, (4-methylphenoxy)acetate, 4-isobutyl-alpha-methylphenylacetate, 4-acetylphenoxyacetic acid, 4-(4-chloro-o-tolyloxy)butyrate, 4-fluorophenylacetate, (alpha,alpha,alpha-trifluoro-p-tolyl)acetate, 3-(4-fluorobenzoyl)propionate, 3-(4-chlorobenzoyl)propionate, 4-chlorophenylacetate, bis(4-chlorophenyl)acetate, 4-bromophenylacetate, 3,3,3-tris(4-chlorophenyl)propionate, 4-(bromomethyl)phenylacetate, 1-(4-chlorophenyl)-1-cyclopentanecarboxylate, 4-methoxyphenylacetate, 4-ethoxyphenylacetate, 3-(4-methoxyphenyl)propionate, 4-(4-methoxyphenyl)propionate, 4-chlorophenoxyacetate, bis(4-chlorophenoxy)acetate, 4-(methylthio)-phenylacetate, 4-nitrophenylacetate, 2-(4-nitrophenyl)propionate, 4-(4-nitrophenyl)butyrate, 3-(4-methoxybenzoyl)propionate, 4-fluorophenoxyacetate, 2-(4-chlorophenoxy)propionate, 2-(4-chlorophenoxy)2-methylpropionate, (2,4-di-tert-pentylphenoxy)acetate, 2,6-difluorophenylacetate, 2,4-difluorophenylacetate, 2,5-difluorophenylacetate, 3,5-difluorophyenylacetate, 4-chloro-o-tolyloxyacetate, 2,3-dichlorophenoxyacetate, 2,6-dichlorophenylacetate, 2,4-dichlorophenylacetate, 2,4-dichlorophenoxyacetate, 3,4-dichlorophenylacetate, 3,4-dichlorophenoxyacetate, 3,5-bis(trifluoromethyl) phenylacetate, 4-(2,4-di-tert-pentylphenoxy)butyrate, 2-(2,4-dichlorophenoxy)propionate, 4-(2,4-dichlorophenoxy) propionate, 2,4,5-trichlorophenoxyacetate, 2-(2,4,5-trichlorophenoxy)propionate, (3,4-dimethoxyphenyl) acetate, 4-benzyloxy-3-methoxyphenylacetate, 3,4-(methylenedioxy)phenylacetate, 5-methoxy-1-indanone-3-acetate, 3-(3,4-dimethoxyphenyl)propionate, 4-(3,4-dimethoxyphenyl)butyrate, (2,5-dimethoxyphenyl)acetate, 2,4-dinitrophenylacetate, (3,5-dimethoxyphenyl)acetate, 3,4,5-trimethoxyphenylacetate, 3-(3,4,5-trimethoxyphenyl) propionate, 2,3,4,5,6-pentafluorophenylacetate, 4-biphenylacetate, 1-naphthylacetate, 2-naphthylacetate, alpha-trityl-2-naphthalenepropionate, (1-naphthoxy)acetate, (2-naphthoxy)acetate, 6-methoxy-alpha-methyl-2-naphthaleneacetate, 9-fluoreneacetate, 1-pyreneacetate, 1-pyrenebutyrate, gamma-oxo-1-pyrenebutyrate, styrylacetate, cinnamate, alpha-methylcinnamate, alpha-fluorocinnamate, alpha-phenylcinnamate, 2-methylcinnamate, 2-fluorocinnamate, 2-(trifluoromethy)cinnamate, 2-chlorocinnamate, 2-methoxycinnamate, 2-nitrocinnamate, 3-fluorocinnamate, 3-(trifluoromethyl)cinnamate, 3-chlorocinnamate, 3-bromocinnamate, 3-methoxycinnamate, 3-nitrocinnamate, 4-methylcinnamate, 4-fluorocinnamate, 4-(trifluoromethyl)cinnamate, 4-chlorocinnamate, 4-bromocinnamate, 4-methoxycinnamate, 4-nitrocinnamate, 4-formylcinnamate, 2,6-difluorocinnamate, 2,4-difluorocinnamate, 2,5-difluorocinnamate, 3,4-difluorocinnamate, 3,5-difluorocinnamate, 2-chloro-6-fluorocinnamate, 2,4-dichlorocinnamate, 3,4-dichlorocinnamate, 5-bromo-2-methoxycinnamate, 2,3-dimethoxycinnamate, 2,4-dimethoxycinnamate, 2,5-dimethoxycinnamate, 3,4-dimethoxycinnamate, 3,4-(methylenedioxy)cinnamate, 3,5-dimethoxycinnamate, 2-chloro-5-nitrocinnamate, 4-chloro-3-nitrocinnamate, 2,3,4-trifluorocinnamate, 3,4,5-trimethoxycinnamate, 2,4,5-trimethoxycinnamate, alpha-methyl-2,4,5-trimethoxycinnamate, 4,5-dimethoxy-2-nitrocinnamate, 2,3,4,5,6-pentafluorocinnamate, 3-methylindene-2-carboxylate, 3-(4-methylbenzoyl)acrylate, 3-(2,5-dimethylbenzoyl)acrylate, 3-(2,3,5,6-tetramethylbenzoyl)acrylate, 3-(4-methoxybenzoyl)acrylate, 3-(4-ethoxybenzoyl)acrylate, 6-methylchromone-2-carboxylate, benzoate, o-toluate, 2-fluorobenzoate, alpha,alpha,alpha-trifluoro-o-toluate, 2-chlorobenzoate, 2-bromobenzoate, 2-iodobenzoate, o-anisate, 2-ethoxybenzoate, 2-nitrobenzoate, 2-acetylbenzoate, 2-(p-toluoyl)benzoate, m-toluate, 3-fluorobenzoate, alpha,alpha,alpha-trifluoro-m-toluate, 3-chlorobenzoate, 3-(chloromethyl)benzoate, 3-bromobenzoate, 3-iodobenzoate, m-anisate, 3-nitrobenzoate, p-toluate, 4-ethylbenzoate, 4-n-propylbenzoate, 4-isopropylbenzoate, 4-n-butylbenzoate, 4-tert-butylbenzoate, 4-pentylbenzoate, 4-hexylbenzoate, 4-heptylbenzoate, 4-octylbenzoate, 4-vinylbenzoate, 4-fluorobenzoate, alpha,alpha,alpha-trifluoro-o-toluate, 4-chlorobenzoate, 4-bromobenzoate, 4-iodobenzoate, 4-(chloromethyl)benzoate, alpha-bromo-p-toluate, p-anisate, 4-(trifluoromethoxy)benzoate, 4-ethoxybenzoate, 4-n-propoxybenzoate, 4-butoxybenzoate, 4-pentyloxybenzoate, 4-hexyloxybenzoate, 4-heptyloxybenzoate, 4-octyloxybenzoate, 4-nonyloxybenzoate, 4-decyloxybenzoate, 4-nonyloxybenzoate, 4-dodecyloxybenzoate, 4-isopropoxybenzoate, 4-(2-cyclohexenyloxy)benzoate, 4-(methylthio) benzoate, 4-(ethylthio)benzoate, 4-nitrobenzoate, 4-acetylbenzoate, 2,3-dimethylbenzoate, 2,6-dimethylbenzoate, 3-fluoro-2-methylbenzoate, 2,3-difluorobenzoate, 2,6-difluorobenzoate, 2-fluoro-6-(trifluoromethyl)benzoate, 2-fluoro-3-(trifluoromethyl)benzoate, 2,6-bis(trifluoromethyl)benzoate, 2-chloro-6-fluorobenzoate, 2-chloro-6-fluorophenylacetate, 2,3-dichlorobenzoate, 2,6-dichlorobenzoate, 2,3-dimethoxybenzoate, 2,6-dimethoxybenzoate, 2-methyl-6-nitrobenzoate, 3-methyl-2-nitrobenzoate, 2-methyl-3-nitrobenzoate, 3-chloro-2-nitrobenzoate, 2-chloro-3-nitrobenzoate, 2-bromo-3-nitrobenzoate, 3-methoxy-2-nitrobenzoate, 3,4-dimethylbenzoate, 2,4-dimethylbenzoate, 2,5-dimethylbenzoate, 5-fluoro-2-methylbenzoate, 3-fluoro-4-methylbenzoate, 2-fluoro-5-methylbenzoate, 3-bromo-4-methylbenzoate, 2,4-bis(trifluoromethyl)benzoate, 3-iodo-4-methylbenzoate, 2-chloro-5-(trifluoromethyl)benzoate, 2,5-bis(trifluoromethyl)benzoate, 2,4-difluorobenzoate, 3,4-difluorobenzoate, 4-fluoro-2-(trifluoromethyl)benzoate, 2-fluoro-4-(trifluoromethyl)benzoate, 2-chloro-4-fluorobenzoate, 3-chloro-4-fluorobenzoate, 2,4-dichlorobenzoate, 3,4-dichlorobenzoate, 2,5-difluorobenzoate, 2,5-dichlorobenzoate, 3-bromo-4-fluorobenzoate, 5-bromo-2-chlorobenzoate, 3-methoxy-4-methylbenzoate, 3-fluoro-4-methoxybenzoate, 4-chloro-o-anisate, 5-chloro-o-anisate, 2-bromo-5-methoxybenzoate, 2,4-dimethoxybenzoate, 2,5-dimethoxybenzoate, 3,4-dimethoxybenzoate, 3,4-diethoxybenzoate, piperonylate, 2-chloro-5-(methylthio)benzoate, 2-methoxy-4-(methylthio)benzoate; 5-methyl-2-nitrobenzoate, 4-methyl-3-nitrobenzoate, 3-methyl-4-nitrobenzoate, 2-nitro-alpha,alpha,alpha-trifluoro-p-toluate, 2-fluoro-5-nitrobenzoate, 4-chloro-2-nitrobenzoate, 2-chloro-4-nitrobenzoate, 4-fluoro-3-nitrobenzoate, 4-chloro-3-nitrobenzoate, 5-chloro-2-nitrobenzoate, 2-chloro-5-nitrobenzoate, 2-bromo-5-nitrobenzoate, 4-(bromomethyl)-3-nitrobenzoate, 2-methoxy-4-nitrobenzoate, 4-methoxy-3-nitrobenzoate, 3-methoxy-4-nitrobenzoate, 5-methoxy-2-nitrobenzoate, 2,4-dinitrobenzoate, 3,5-dimethylbenzoate, 3,5-di-tert-butylbenzoate, 3,5-difluorobenzoate, 3,5-bis (trifluoromethyl)benzoate, 3,5-dichlorobenzoate, 3,5-dibromobenzoate, 3-bromo-5-iodobenzoate, 3,5-dimethoxybenzoate, 3,5-dinitrobenzoate, 2,3,4-trifluorobenzoate, 2,3,6-trifluorobenzoate, 2,4,6-trimethylbenzoate, 2,4,6-trifluorobenzoate, 3,4,5-trifluorobenzoate, 2,4,6-trichlorobenzoate, 2,3,5-trichlorobenzoate, 2,3,5-triiodobenzoate, 2-bromo-4,5- dimethoxybenzoate, 3,4,5-trimethoxybenzoate, 3,4,5-triethoxybenzoate, 4,5-dimethoxy-2-nitrobenzoate, 3,5-dinitro-o-toluate, 3,5-dinitro-p-toluate, 2-chloro-3,5-dinitrobenzoate, 4-chloro-3,5-dinitrobenzoate, 2,5-dichloro-3-nitrobenzoate, 2,6-dichloro-3-nitrobenzoate, 2,3,4-trimethoxybenzoate, 2,4,5-trifluorobenzoate, 2-chloro-4,5-difluorobenzoate, 2,4-dichloro-5-fluorobenzoate, 2,4,5-trimethoxybenzoate, 2,3,4,5-tetrafluorobenzoate, 2,3,5,6-tetrafluorobenzoate, 2,4-dichloro-3,5-dinitrobenzoate, 2,3,5,6-tetrafluoro-p-toluate, 4-bromo-2,3,5,6-tetrafluorobenzoate, pentafluorobenzoate, 2-biphenylcarboxylate, 4'-(trifluoromethyl)-2-biphenylcarboxylate, 4-biphenylcarboxylate, 4'-ethyl-4-biphenylcarboxylate, 4'-octyloxy-4-biphenylcarboxylate, alpha-phenyl-o-toluate, 2-bibenzylcarboxylate, 2,3,4,5,6-pentafluorophenoxyacetate, 2-phenoxybenzoate, 3-phenoxybenzoate, 2-benzoylbenzoate, 3-benzoylbenzoate, 4-benzoylbenzoate, 2-(4-fluorobenzoyl)benzoate, 2-(4-chlorobenzoyl)benzoate, 2-(4-chloro-3-nitrobenzoyl)benzoate, 1-naphthoate, 2-naphthoate, 4-fluoro-1-naphthoate, 2-ethoxy-1-naphthoate, 1,8-naphthalaldehydate, naphthenate, 2-biphenylenecarboxylate, gamma-oxo-5-acenaphthenebutyrate, 9-fluorenecarboxylate, 1-fluorenecarboxylate, 4-fluorenecarboxylate, 9-fluorenone-1-carboxylate, 9-fluorenone-2-carboxylate, 9-fluorenone-4-carboxylate, 7-nitro-4-fluorenecarboxylate, chromone-2-carboxylate, 9-anthracenecarboxylate, anthraquinone-2-carboxylate, xanthene-9-carboxylate, 1-pyrenecarboxylate, and the like, dicarboxylic acid derived anions, such as malonate, methylmalonate, ethylmalonate, butylmalonate, dimethylmalonate, diethylmalonate, succinate, methylsuccinate, dimethylsuccinate, 2-ethyl-2-methylsuccinate, 2,3-dimethylsuccinate, glutarate, 2-methylglutarate, 3-methylglutarate, 2,2-dimethylglutarate, 3,3-dimethylglutarate, 2-ketoglutarate, adipate, 3-methyladipate, 3-tert-butyladipate, pimelate, suberate, azelate, sebacate, perfluorosebacate, 1,11-undecanedicarboxylate ($^-OOC(CH_2)_{11}COO^-$), undecanedioate ($^-OOC(CH_2)_9COO^-$), 1,10-decanedicarboxylate ($^-OOC(CH_2)_{10}COO^-$), 1,12-dodecanedicarboxylate ($^-OOC(CH_2)_{12}COO^-$), hexadecanedioate ($^-OOC(CH_2)_{14}COO^-$), docosanedioate ($^-OOC(CH_2)_{20}COO^-$), tetracosanedioate ($^-OOC(CH_2)_{22}COO^-$), itaconate, maleate, fumarate, citraconate, mesaconate, glutaconate, β-hydromuconate, traumatate, muconate, chlorosuccinate, bromosuccinate, 2,3-dibromosuccinate, tetrafluorosuccinate, hexafluoroglutarate, perfluoroadipate, perfluorosuberate, 3-chlorododecanedioate, dibromomaleate, diglycolate, 3,6-dioxaoctanedioate, thiodiglycolate, 3,3'-thiodipropionate, 1,3-acetonedicarboxylate, 3-oxoadipate, 4-ketopimelate, 5-oxoazelate, chelidonate, 1,2-cyclopentanedicarboxylate, 3,3-tetramethyleneglutarate, camphorate, cyclohexylsuccinate, 1,1-cyclohexanediacetate, 1,2-cyclohexanedicarboxylate, 1,3-cyclohexanedicarboxylate, 1,4-cyclohexanedicarboxylate, 1,3-adamantanedicarboxylate, 1,3-adamantanediacetate, 5-norbornene-2,3-dicarboxylate, 1,4,5,6,7,7-hexachloro-5-norbornene-2,3-dicarboxylate, phenylsuccinate, 3-phenylglutarate, 1,2-phenylenediacetate, 1,2-phenylenedioxydiacetate, homophthalate, 1,3-phenylenediacetate, 4-carboxyphenoxyacetate, 1,4-phenylenediacetate, 1,4-phenylenedipropionate, 2-carboxycinnamate, 1,4-phenylenediacrylate, 2-carboxybenzenepropanoate, 4,4'-(hexafluoroisopropylidene)bis(benzoate), 4,4'-oxybis(benzoate), phthalate, isophthalate, terephthalate, 3-fluorophthalate, 2-methoxyisophthalate, 3-nitrophathalate, 4-methylphthalate, 2-bromoterephthalate, 4-bromoisophthalate, 4-nitrophthalate, nitroterephthalate, 5-tert-butylisophthalate, 5-octadecyloxyisophthalate, 5-nitroisophthalate, 4,5-dichlorophthalate, tetrafluoroterephthalate, tetrafluoroisophthalate, tetrafluorophthalate, diphenate, 4,4'-biphenyldicarboxylate, 4-(4-(2-carboxybenzoyl)phenyl)butyrate, 1,4-naphthalenedicarboxylate, 2,3-naphthalenedicarboxylate, 2,6-naphthalenedicarboxylate, 2,7-di-tert-butyl-9,9-dimethyl-4,5-xanthenedicarboxylate, phenylmalonate, benzylmalonate, and the like, tricarboxylic acid derived anions, such as tricarballylate, of the formula

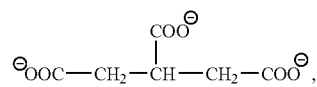

aconitate, nitromethanetrispropionate, 1,3,5-cyclohexanetricarboxylate, 1,3,5-trimethyl-1,3,5-cyclohexanetricarboxylate, 1,2,3-benzenetricarboxylate, 1,2,4-benzenetricarboxylate, 1,3,5-benzenetricarboxylate, 5-(4-carboxy-2-nitrophenoxyisophthalate, and the like, tetracarboxylic acid derived anions, such as 1,2,3,4-butanetetracarboxylate, tetrahydrofuran-2,3,4,5-tetracarboxylate, 2,2',2'',2'''-(1,2-ethanediylidene-tetrakis(thio))-tetrakisacetate, cyclobutanetetracarboxylate, 1,2,4,5-benzenetetracarboxylate, 1,4,5,8-naphthalenetetracarboxylate, and the like monomeric compounds with higher degrees of carboxylate substitution, such as 1,2,3,4,5,6-cyclohexanehexacarboxylate, mellitate, and the like, sulfonic acid derived anions, such as methanesulfonate, ethanesulfonate, 1-propanesulfonate, 2-propanesulfonate, 1-butanesulfonate, 1-pentanesulfonate, 1-hexanesulfonate, 1-heptanesulfonate, 1-octanesulfonate, 1-nonanesulfonate, 1-decanesulfonate, 1-dodecanesulfonate, 1-tetradecanesulfonate, 1-hexadecanesulfonate, vinylsulfonate, 2-methyl-2-propene-1-sulfonate, trifluoromethanesulfonate, 2-chloroethanesulfonate, 2-bromoethanesulfonate, nonafluoro-1-butanesulfonate, perfluoro-1-octanesulfonate, PIPES, of the formula

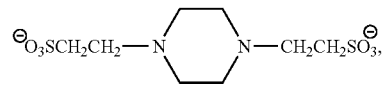

MES, of the formula

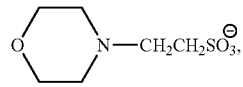

MOPS, of the formula

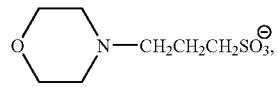

10-camphorsulfonate, 3-bromocamphor-8-sulfonate, 3-bromocamphor-10-sulfonate, 3-sulfopropylacrylate, 3-sulfopropylmethacrylate, dioctyl sulfosuccinate, p-toluene sulfonate, 4-ethylbenzenesulfonate, 4-chlorobenzenesulfonate, 2,4-dinitrobenzenesulfonate, 2-mesitylenesulfonate, 1-naphthalenesulfonate, 2-naphthalenesulfonate, 5-dimethylamino-1- naphthalenesulfonate, 1,5-naphthalene disulfonate, 4-sulfo-1,8-naphthalic anhydride salt, benzenesulfonate, xylenesulfonate, 4-octylbenzenesulfonate, dodecylbenzenesulfonate, 4-styrenesulfonate, 3-nitrobenzenesulfonate, 2-formylbenzenesulfonate, 4-acetylbenzenesulfonate, 4-sulfophenylisothiocyanate salt, 1,2-benzenedisulfonate, 1,3-benzenedisulfonate, 2-formyl-1,3-benzenedisulfonate, 4-chloro-3-nitrobenzenesulfonate, 4,4'-diisothiocyanato-2,2'-distilbenesulfonate, pentafluorobenzenesulfonate, 1,2-naphthoquinone-4-sulfonate, 2,6-naphthalenedisulfonate, 1,3,6-naphthalenetrisulfonate, 1,3,7-naphthalenetrisulfonate, 9,10-dimethoxy-2-anthracenesulfonate, anthraquinone-2-sulfonate, anthraquinone-1,5-disulfonate, anthraquinone-2,6-disulfonate, and the like, compounds having both sulfonate groups and carboxylate groups, such as sulfoacetate, sulfosuccinate, 2-sulfobenzoate, 3-sulfobenzoate, 4-sulfobenzoate, 4-sulfophthalate, 5-sulfoisophthalate, dimethyl-5-sulfoisophthalate, and the like, diethyldithiocarbamate, and the like, as well as mixtures thereof.

In a specific embodiment, the anion can be an organic dianion of the formula $A_{11}$-$R_{11}$-$A_{22}$ wherein $A_{11}$ and $A_{22}$ each, independently of the other, are anionic groups, such as carboxylate, sulfonate, or the like, and wherein $R_{11}$ is (i) an alkylene group (including linear, branched, saturated, unsaturated, cyclic, substituted, and unsubstituted alkylene groups, and wherein hetero atoms, such as oxygen, nitrogen, sulfur, silicon, phosphorus, and the like either may or may not be present in the alkylene group), in one embodiment with at least 1 carbon atom, in another embodiment with at least about 2 carbon atoms, in yet another embodiment with at least about 6 carbon atoms, in another embodiment with at least about 8 carbon atoms, and in yet another embodiment with at least about 18 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, (ii) an arylene group (including unsubstituted and substituted arylene groups, and wherein hetero atoms, such as oxygen, nitrogen, sulfur, silicon, phosphorus, and the like either may or may not be present in the arylene group), in one embodiment with at least about 6 carbon atoms, in another embodiment with at least about 10 carbon atoms, and in yet another embodiment with at least about 14 carbon atoms, and in one embodiment with no more than about 26 carbon atoms, in another embodiment with no more than about 22 carbon atoms, and in yet another embodiment with no more than about 18 carbon atoms, although the number of carbon atoms can be outside of these ranges, (iii) an arylalkylene group (including unsubstituted and substituted arylalkylene groups, wherein the alkyl portion of the arylalkylene group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the arylalkylene group), in one embodiment with at least about 7 carbon atoms, in another embodiment with at least about 12 carbon atoms, and in yet another embodiment with at least about 18 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as benzyl or the like, or (iv) an alkylarylene group (including unsubstituted and substituted alkylarylene groups, wherein the alkyl portion of the alkylarylene group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the alkylarylene group), in one embodiment with at least about 7 carbon atoms, in another embodiment with at least about 12 carbon atoms, and in yet another embodiment with at least about 18 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as tolyl or the like, and wherein the substituents on the substituted alkylene, arylene, arylalkylene, and alkylarylene groups can be (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring. Examples of suitable organic dianions include unsubstituted and substituted naphthalene disulfonates, unsubstituted and substituted benzene disulfonates, and the like, as well as mixtures thereof.

In another specific embodiment, the organic anion can be an organic trianion, tetraanion, and higher, an oligomeric or polymeric anion, such as a polysulfonate or polycarboxylate, or the like. Mixtures of two or more different anions can also be used.

A few specific examples of commercially available metal salts include (but are not limited to) Zn HEX-CEM (zinc 2-ethylhexanoate, available from OMG Americas, Inc., Cleveland, Ohio), zinc trifluoroacetate hydrate $((CF_3COO)_2Zn.xH_2O$, available from Aldrich Chemical Co., Milwaukee, Wis.), zinc p-toluenesulfonate hydrate $((CH_3C_6H_4SO_3)_2Zn.xH_2O$, available from Aldrich Chemical Co.), zinc diethyldithiocarbamate $([(C_2H_5)_2NCS_2]_2Zn$, available from Aldrich Chemical Co.), zinc acetylacetonate hydrate $((CH_3COCH=C(O-)CH_3)_2Zn.xH_2O$, available from Aldrich Chemical Co.), zinc bis(2,2,6,6-tetramethyl-3,5-heptanedionate) $([(CH_3)_3CCOCH=C(O-)C(CH_3)_3]_2Zn$, available from Aldrich Chemical Co.), zinc citrate dihydrate $([OOC-CH_2C(OH)(COO)CH_2COO]_2Zn_3.2H_2O$, available from Aldrich Chemical Co.), zinc naphthenate (available from Aldrich Chemical Co.), zinc stearate $([CH_3(CH_2)_{16}COO]_2Zn$, available from Aldrich Chemical Co.), zinc undecylenate $([H_2C=CH(CH_2)_8COO]_2Zn$, available from Aldrich Chemical Co.), calcium acetate hydrate $((CH_3COO)_2Ca.xH_2O$, available from Aldrich Chemical Co.), calcium bis(6,6,7,7,8,8,8-heptafluoro-2,2-dimethyl-3,5,-octanedionate) (available from Aldrich Chemical Co.), calcium citrate tetrahydrate $([OOCCH_2C(OH)(COO)CH_2COO]_2Ca_3.4H_2O$, available from Aldrich Chemical Co.), calcium cyclohexanebutyrate $([C_6H_{11}(CH_2)_3COO]_2Ca$, available from Aldrich Chemical Co.), and the like, as well as mixtures thereof.

In situations wherein 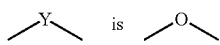 is /Y\ O /Y\ and either (i) one of the $R_7$ groups is in the ortho position and is either an ester based on a carboxylic acid, an ester based on a sulfonic acid, an amide based on a carboxylic acid, or an amide based on a sulfonic acid, or (ii) one of the $Q^-$ groups is a sulfonate salt, i.e., when the chromogen is of the formula

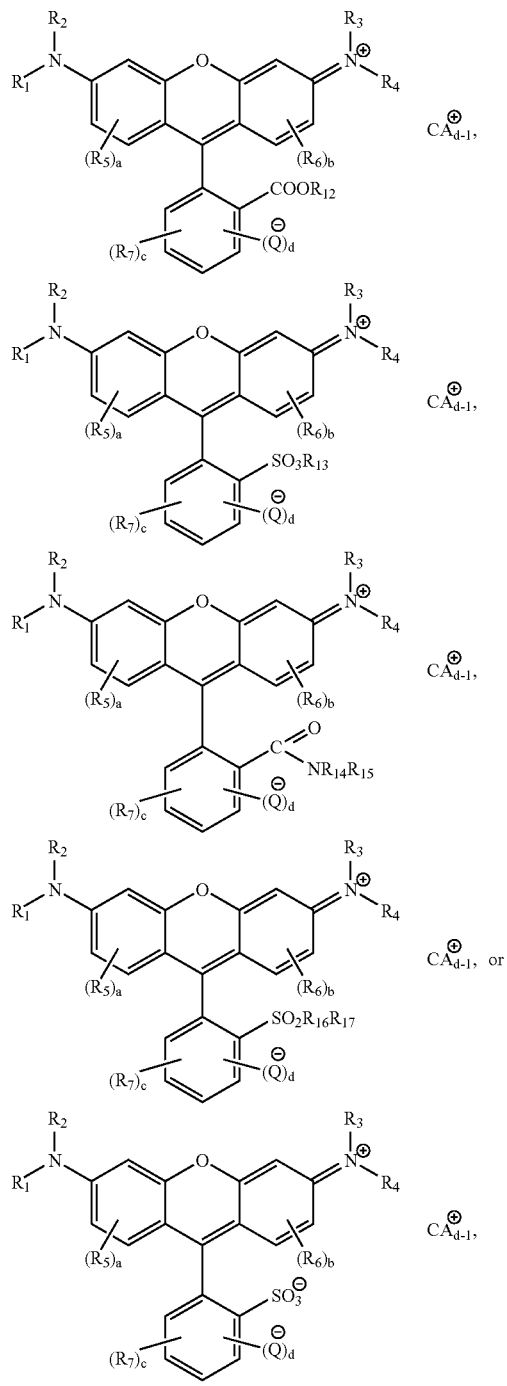

wherein $R_{12}$, $R_{13}$, $R_{14}$, $R_{15}$, $R_{16}$, and $R_{17}$ each, independently of the other, is (i) an alkyl group (including linear, branched, saturated, unsaturated, cyclic, substituted, and unsubstituted alkyl groups, and wherein hetero atoms, such as oxygen, nitrogen, sulfur, silicon, phosphorus, and the like either may or may not be present in the alkyl group), in one embodiment with at least 1 carbon atom, and in one embodiment with no more than about 50 carbon atoms, in another embodiment with no more than about 30 carbon atoms, and in yet another embodiment with no more than about 18 carbon atoms, although the number of carbon atoms can be outside of these ranges, (ii) an aryl group (including unsubstituted and substituted aryl groups, and wherein hetero atoms, such as oxygen, nitrogen, sulfur, silicon, phosphorus, and the like either may or may not be present in the aryl group), in one embodiment with at least about 6 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges, (iii) an arylalkyl group (including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the arylalkyl group), in one embodiment with at least about 7 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges, such as benzyl or the like, or (iv) an alkylaryl group (including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, and the like either may or may not be present in either or both of the alkyl portion and the aryl portion of the alkylaryl group), in one embodiment with at least about 7 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges, such as tolyl or the like, wherein the substituents on the substituted alkyl, aryl, arylalkyl, and alkylaryl groups can be (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring, in one specific embodiment, (I) either (a) c is an integer which is 0, 1, 2, or 3, or (b) d is an integer which is 1, 2, 3, or 4, and (II) either (a) three of $R_1$, $R_2$, $R_3$, and $R_4$ are hydrogen atoms; (b) only one of $R_1$, $R_2$, $R_3$, and $R_4$ is a hydrogen atom; (c) $R_1$ and $R_2$ are both hydrogen atoms; (d) $R_3$ and $R_4$ are both hydrogen atoms; or (e) $R_1$ and $R_3$ are both hydrogen atoms and $R_2$ and $R_4$ are each, independently of the other, either alkyl groups or arylalkyl groups.

In one embodiment, the number of carbon atoms in $R_1+R_2+R_3+R_4$ is at least about 16, in another embodiment at least about 18, in yet another embodiment at least about 20, in still another embodiment at least about 22, in another embodiment at least about 24, in yet another embodiment at least about 26, in still another embodiment at least about 28, in another embodiment at least about 30, in yet another embodiment at least about 32, in still another embodiment at least about 34, in another embodiment at least about 36, in yet another embodiment at least about 38, in still another embodiment at least about 40, in another embodiment at least about 42, in yet another embodiment at least about 44, in still another embodiment at least about 46, in another embodiment at least about 48, in yet another embodiment at least about 50, in still another embodiment at least about 52, in another embodiment at least about 54, in yet another embodiment at least about 56, in still another embodiment at least about 58, in another embodiment at least about 60, in yet another embodiment at least about 62, in still another embodiment at least about 64, in another embodiment at least about 66, in yet another embodiment at least about 68, in still another embodiment at least about 70, and in another embodiment at least about 72.

Since hetero atoms can be included in the alkyl, aryl, arylalkyl, and alkylaryl groups, and since the groups can be substituted, it is to be understood that $R_1$, $R_2$, $R_3$, $R_4$, $R_5$, $R_6$, $R_7$, $R_8$, $R_9$, and $R_{10}$ can also be groups such as alkoxy, polyalkyleneoxy, aryloxy, polyaryleneoxy, arylalkyloxy, polyarylalkyleneoxy, alkylaryloxy, or polyalkylaryleneoxy groups, provided that the oxygen atom in such a group is not directly bonded to a nitrogen, oxygen, or sulfur atom in the

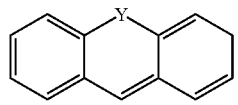

central structure.

Examples of situations wherein one of the $R_{1-4}$ groups is a cycloalkyl is when

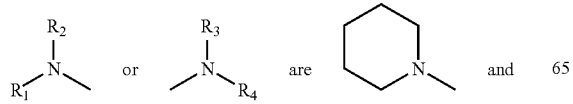

Examples of situations wherein the $R_{1-4}$ groups are joined together to form a ring are when -continued

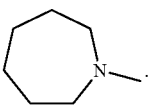

Examples of situations wherein one of the $R_{1-4}$ groups is joined to a phenyl ring in the central structure is when

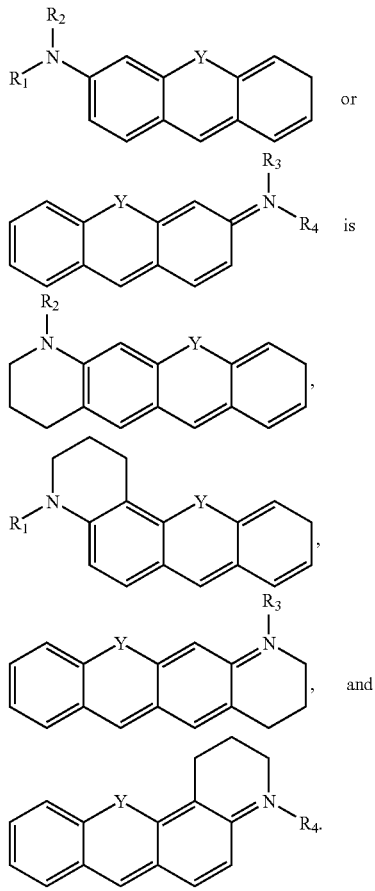

The compounds include those wherein the chromogen is a monocarboxylic acid or a monocarboxylate, wherein

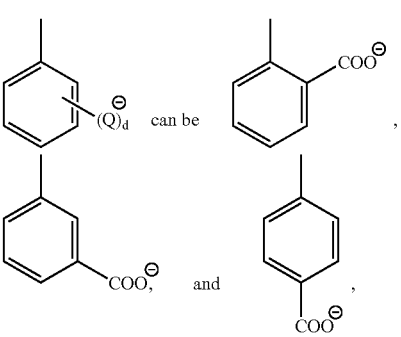

a dicarboxylic acid or a dicarboxylate, wherein

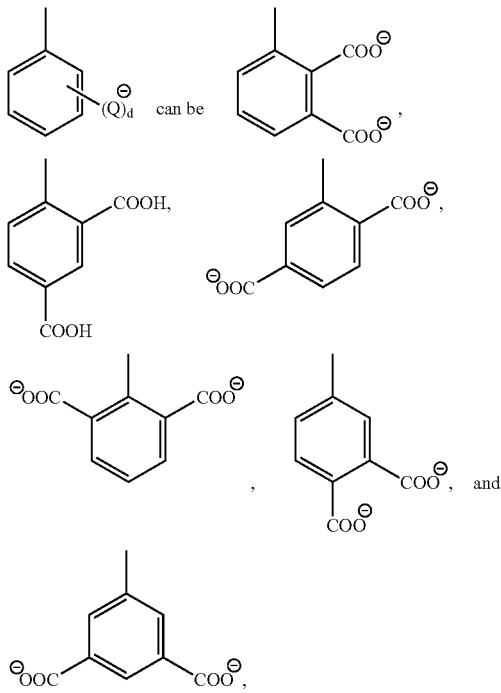

tricarboxylic acids and tricarboxylates, tetracarboxylic acids and tetracarboxylates, pentacarboxylic acids and pentacarboxylates, monosulfonic acids and monosulfonates, wherein

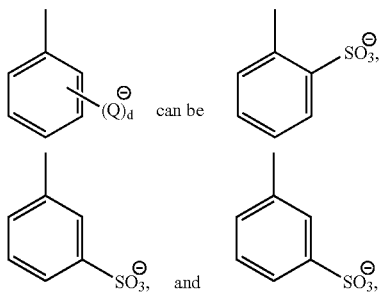

disulfonic acids and disulfonates, wherein

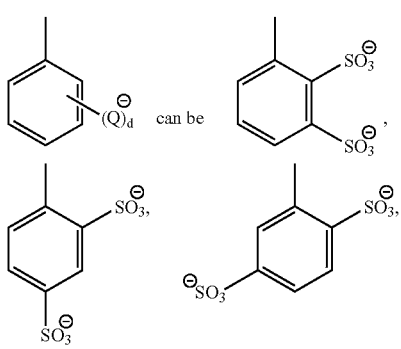

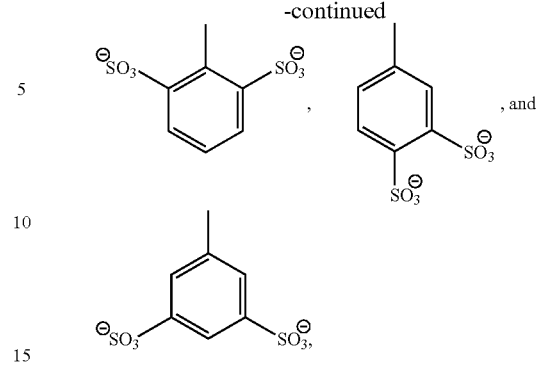

trisulfonic acids and trisulfonates, tetrasulfonic acids and tetrasulfonates, pentasulfonic acids and pentasulfonates, monocarboxylic acid monosulfonic acids and monocarboxylate monosulfonates, wherein

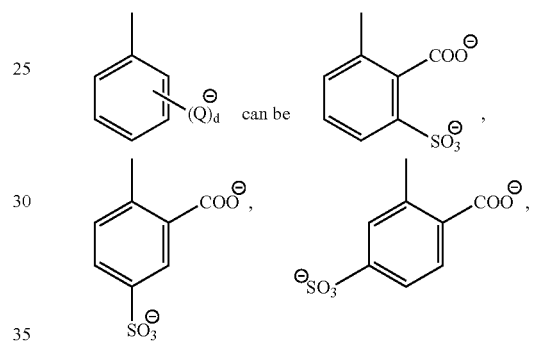
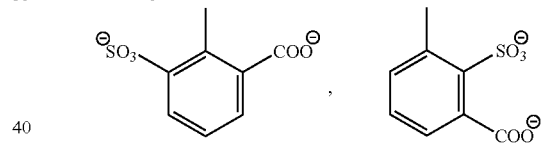
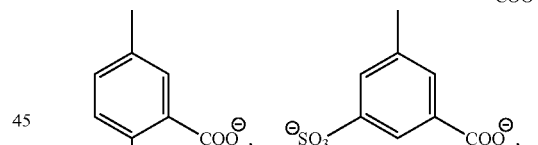
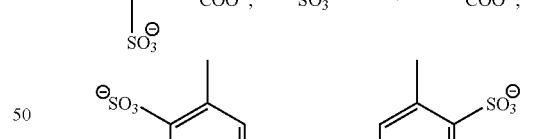
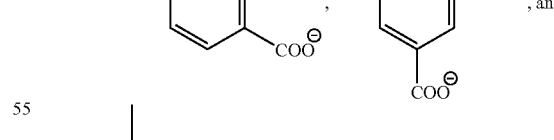
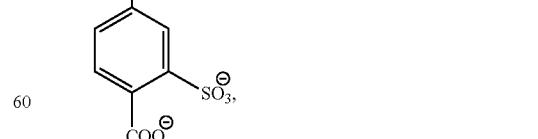
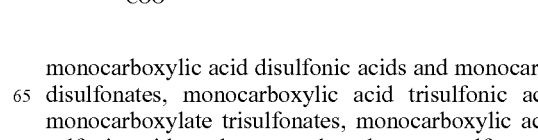

monocarboxylic acid disulfonic acids and monocarboxylate disulfonates, monocarboxylic acid trisulfonic acids and monocarboxylate trisulfonates, monocarboxylic acid tetrasulfonic acids and monocarboxylate tetrasulfonates, dicarboxylic acid monosulfonic acids and dicarboxylate monosulfonates, dicarboxylic acid disulfonic acids and dicarboxylate disulfonates, dicarboxylic acid trisulfonic acids and dicarboxylate trisulfonates, tricarboxylic acid monosulfonic acids and tricarboxylate monosulfonates, tricarboxylic acid disulfonic acids and tricarboxylate disulfonates, tetracarboxylic acid monosulfonic acids and tetracarboxylate monosulfonates, and the like. In addition, it is possible for a compound to have both one or more acid groups (i.e., COOH or $SO_3H$) and one or more anionic salt groups (i.e., $COO^-$ or $SO_3^-$) present in the molecule.

The colorant compounds include rhodamines, wherein

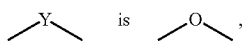

wherein the chromogen is of the general formula

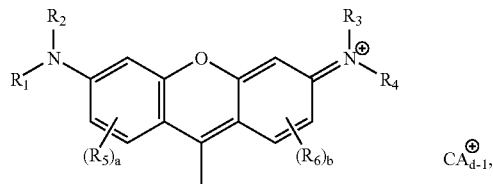

acridines, wherein

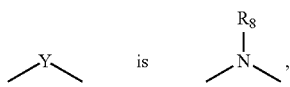

wherein the chromogen is of the general formula

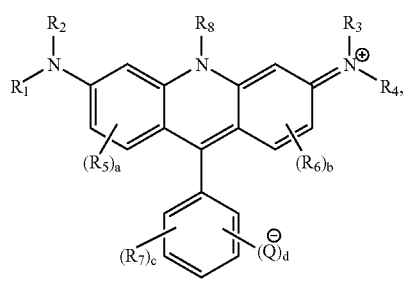

sulforhodamines, wherein

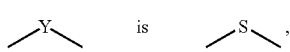

wherein the chromogen is of the general formula

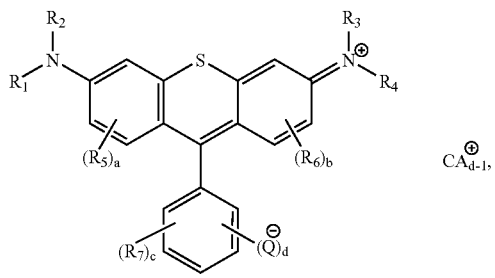

anthracenes, wherein

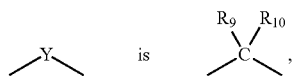

wherein the chromogen is of the general formula

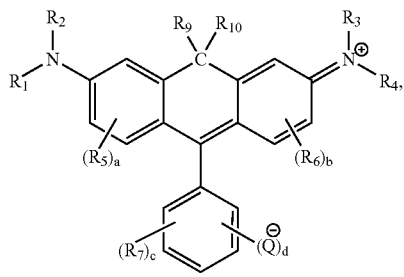

and the like.

In one specific embodiment, the chromogen for the compounds is of the formula

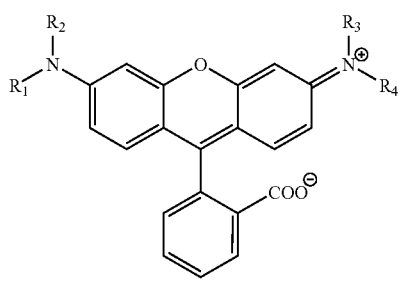

It is to be understood that in chromogens of the formula

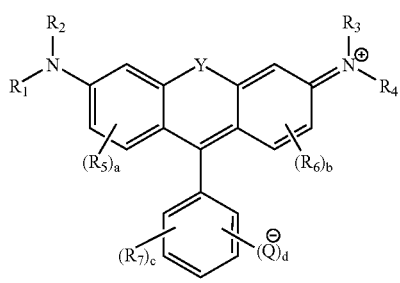

the positive charge is delocalized, and that other tautomeric structures can be drawn, including (but not limited to)

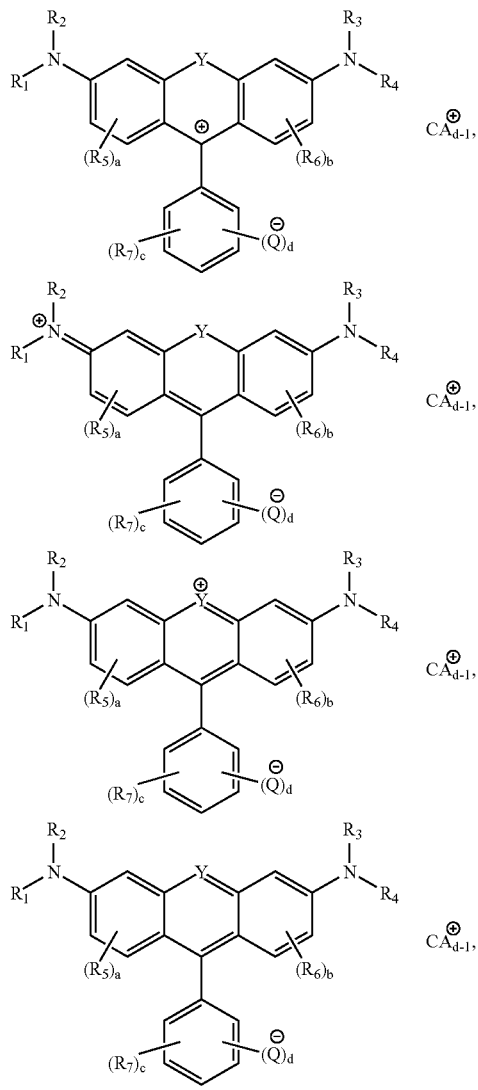

and the like. It is to be understood that all possible tautomeric forms of these colorants are included within the above formulae.

In one specific embodiment, the compounds are of the general formula

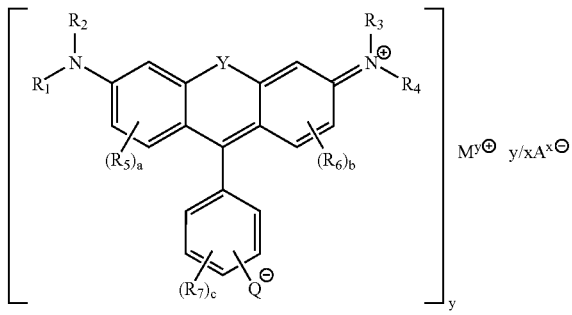

wherein M is a metal cation, y is an integer representing the charge on the metal cation and is at least 2, A is an organic anion, and x is an integer representing the charge on the anion.

The colorant compounds can be prepared by any desired or effective procedure. Preparation of the chromogen will be discussed first. By "chromogen" is meant the

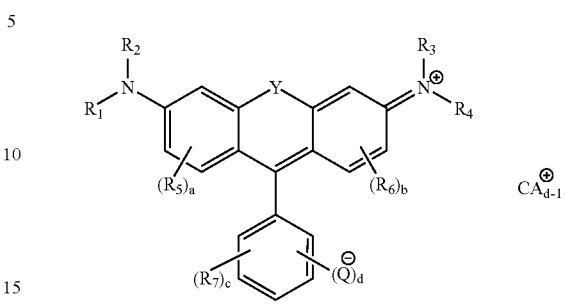

component of the metal compound which is later reacted with the metal cation or metal containing moiety to form the colorant. For example, a dihalofluorescein, such as dichlorofluorescein or the like, can be admixed with one or more amines having the desired $R_1$, $R_2$, $R_3$, and $R_4$ groups thereon, an optional zinc halide, such as zinc chloride or the like, and an optional nonnucleophilic base, such as calcium oxide, zinc oxide, or the like, either neat or, optionally, in the presence of a solvent.

The amine and the dihalofluorescein are present in any desired or effective relative amounts, in one embodiment at least about 0.9 mole of base per every one mole of dihalofluorescein, in another embodiment at least about 0.95 mole of base per every one mole of dihalofluorescein, and in yet another embodiment at least about 1 mole of base per every one mole of dihalofluorescein, and in one embodiment no more than about 20 moles of base per every one mole of dihalofluorescein, in another embodiment no more than about 10 moles of base per every one mole of dihalofluorescein, and in yet another embodiment no more than about 2 moles of base per every one mole of dihalofluorescein, although the relative amounts can be outside of these ranges.

Dichlorofluorescein is commercially available from, for example, Aldrich Chemical Co., Milwaukee, Wis. Dihalofluoresceins can also be prepared by the reaction of fluorescein with $PX_5$ wherein X is fluorine, chlorine, bromine, or iodine, or with a toluenesulfonylhalide, such as toluenesulfonylchloride or the like.

When an optional zinc halide is used, the dihalofluorescein and the zinc halide are present in any desired or effective relative amounts, in one embodiment at least about 2 moles of zinc halide per every one mole of dihalofluorescein, in another embodiment at least about 2.5 moles of zinc halide per every one mole of dihalofluorescein, and yet in another embodiment at least about 3 moles of zinc halide per every one mole of dihalofluorescein, and in one embodiment no more than about 5 moles of zinc halide per every one mole of dihalofluorescein, in another embodiment no more than about 4.5 moles of zinc halide per every one mole of dihalofluorescein, and in yet another embodiment no more than about 4 moles of zinc halide per every one mole of dihalofluorescein, although the relative amounts can be outside of these ranges.

When an optional base is used, the base is present in any desired or effective amount, in one embodiment at least about 2 equivalents of base per every one mole of dihalofluorescein (i.e., about 2 moles of monobasic base per every one mole of dihalofluorescein, about 1 mole of dibasic base, such as calcium oxide, per every one mole of dihalofluorescein, and the like), in another embodiment at least about 2.5 equivalents of base per every one mole of dihalofluorescein, and yet in another embodiment at least about 3 equivalents of base per every one mole of dihalofluorescein, and in one embodiment no more than about 10 equivalents of base per every one mole of dihalofluorescein, in another embodiment no more than about 5 equivalents of base per every one mole of dihalofluorescein, and in yet another embodiment no more than about 3.2 equivalents of base per every one mole of dihalofluorescein, although the relative amounts can be outside of these ranges.

If desired, the reaction can be run neat, in the absence of a solvent. In addition, if desired, the reaction can be run in the presence of an optional solvent. Examples of suitable solvents include tetramethylene sulfone (sulfolane), N-methyl pyrrolidone, dimethyl formamide, dimethyl sulfoxide, octanol, or the like, as well as mixtures thereof. When present, the optional solvent is present in any desired or effective amount, in one embodiment at least about 1 liter per every 0.1 mole of dihalofluorescein, in another embodiment at least about 1 liter per every 0.3 mole of dihalofluorescein, and in yet another embodiment at least about 1 liter per every 0.35 mole of dihalofluorescein, and in one embodiment no more than about 1 liter per every 2 moles of dihalofluorescein, in another embodiment no more than about 1 liter per every 1.5 moles of dihalofluorescein, and in yet another embodiment no more than about 1 liter per every 1 mole of dihalofluorescein, although the relative amounts can be outside of these ranges.

The mixture of dihalofluorescein, amine, optional zinc halide, optional base, and optional solvent is then heated to any effective temperature, in one embodiment at least about 62° C., in another embodiment at least about 150° C., and in yet another embodiment at least about 190° C., and in one embodiment no more than about 280° C., in another embodiment no more than about 220° C., and in yet another embodiment no more than about 200° C., although the temperature can be outside of these ranges.

The mixture of dihalofluorescein, amine, optional zinc halide, optional base, and optional solvent is heated for any effective period of time, in one embodiment at least about 5 minutes, in another embodiment at least about 2 hours, and in yet another embodiment at least about 3 hours, and in one embodiment no more than about 4 days, in another embodiment no more than about 60 hours, and in yet another embodiment no more than about 40 hours, although the time can be outside of these ranges.

If desired, the resulting chromogen product can be purified by pouring the reaction mixture into an organic non-water-soluble and non-water-miscible solvent in which the product is soluble or miscible and in which undesirable salt byproducts are not soluble, such as methyl isobutyl ketone, toluene, hexane, heptane, or the like, followed by admixing the solvent containing the product with water in a separatory funnel and separating the aqueous and organic phases.

The crude chromogen product can then, if desired, be further purified by washing it with aqueous EDTA to remove metal salts, followed by washing with water. If desired, a titration or other instrumental technique, such as AA (atomic absorption) or ICP (inductively coupled plasma) can be performed to determine if the metal salts have been completely removed. The purified product can be isolated by distilling off any solvents.

Various substituents can be placed on the rings of the chromogens by any desired or effective method, such as, for example, the methods disclosed in U.S. Pat. No. 5,847,162 and U.S. Pat. No. 1,991,482, the disclosures of each of which are totally incorporated herein by reference.

Additional numbers of carbon atoms can be placed on the central structure by, for example, selecting long chain amines as reactants. Examples of such compounds include (but are not limited to) those of the formulae

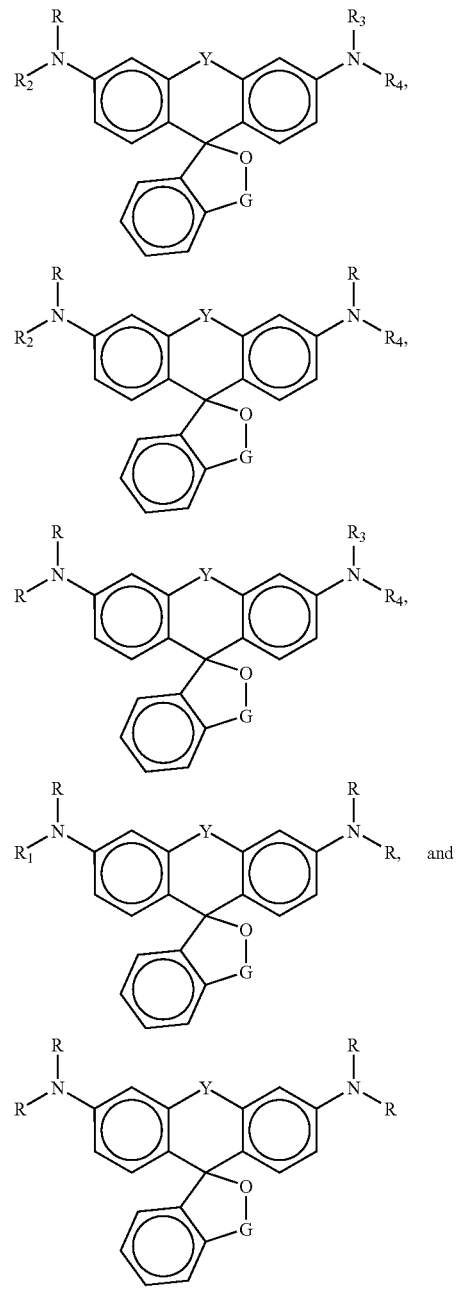

wherein Y, $R_1$, $R_2$, $R_3$, and $R_4$ have the same definitions as given hereinabove, G is either

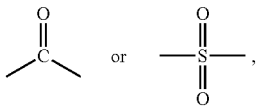

and (1) R is a linear alkyl group of the formula —$C_nH_{2n+1}$ wherein n is at least about 12, (2) R is a branched alkyl group of the formula —$C_nH_{2n+1}$ wherein n is at least about 12, (3) R is an ether group of the formula —$(CH_2)_3$—O—$C_nH_{2n+1}$ wherein n is at least about 11, and the like, as well as their ring-opened, or protonated, or free-base forms and their zwitterionic forms.

Additional numbers of carbon atoms can also be placed on the central structure by, for example, first preparing the corresponding alcohols and then reacting these alcohols with, for example, high-carbon-number acids to prepare esters, high-carbon-number isocyanates to prepare urethanes, or the like. Examples of such compounds include (but are not limited to) those of the formulae

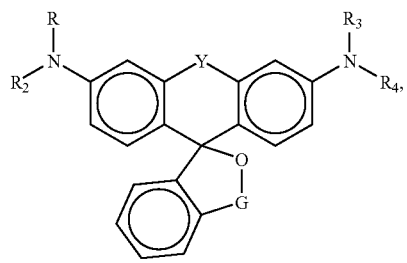

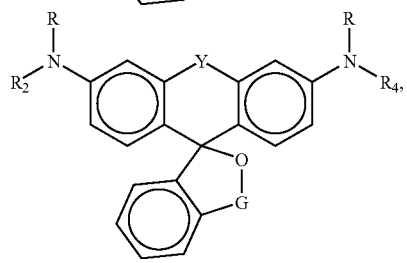

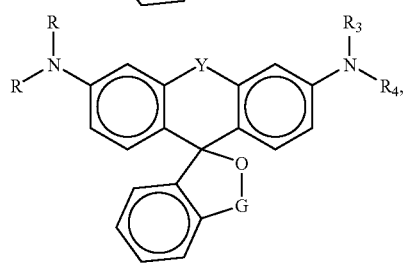

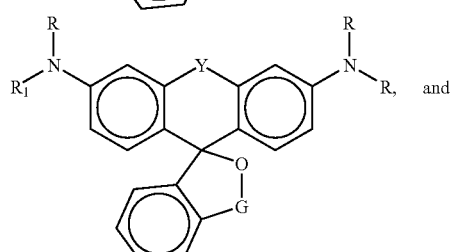

and

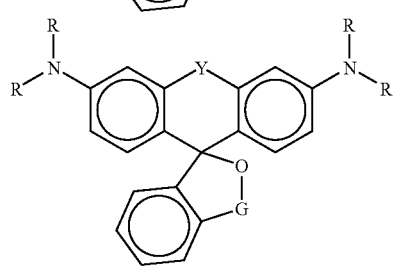

wherein Y, $R_1$, $R_2$, $R_3$, and $R_4$ have the same definitions as given hereinabove, G is either

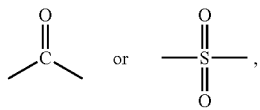

and (1) R is a group of the formula

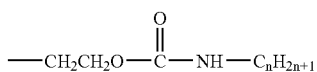

wherein n is at least about 12, (2) R is a group of the formula

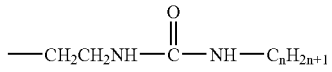

wherein n is at least about 12, (3) R is a group of the formula

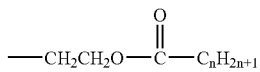

wherein n is at least about 12, (4) R is a group of the formula

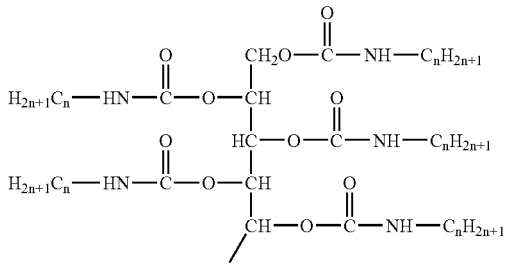

wherein n is at least about 12, (5) R is a group of the formula

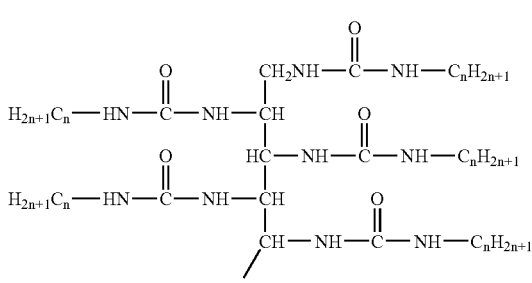

wherein n is at least 12, (6) R is a group of the formula

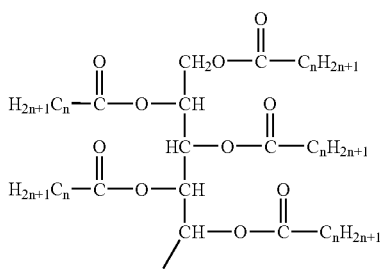

wherein n is at least about 12, (7) two R groups on the same nitrogen atom form a group, with the nitrogen atom, of the formula

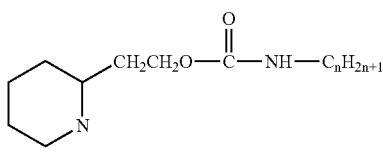

wherein n is at least about 12, (8) two R groups on the same nitrogen atom form a group, with the nitrogen atom, of the formula

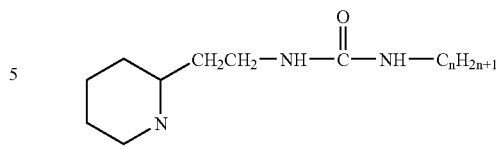

wherein n is at least about 12, (9) two R groups on the same nitrogen atom form a group, with the nitrogen atom, of the formula

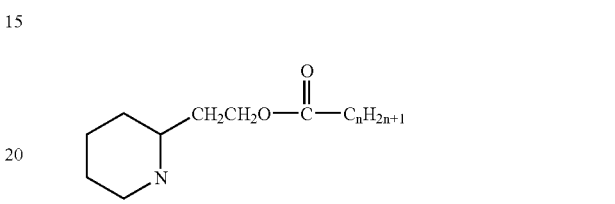

wherein n is at least about 12, and the like, as well as their ring-opened, or protonated, or free-base forms and their zwitterionic forms.

Some specific examples of such compounds include (a) those of the formulae

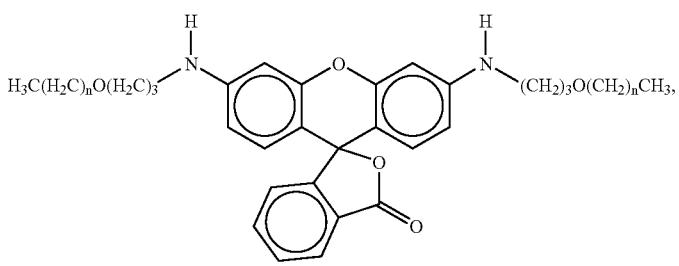

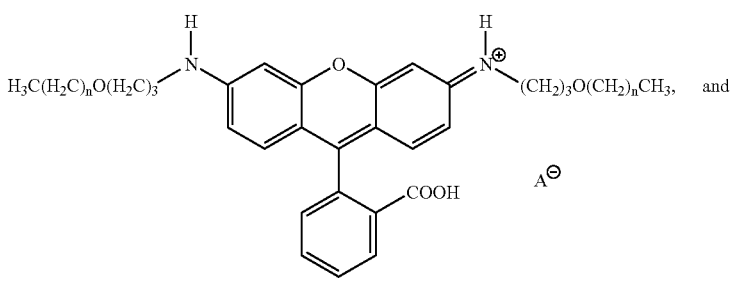

and

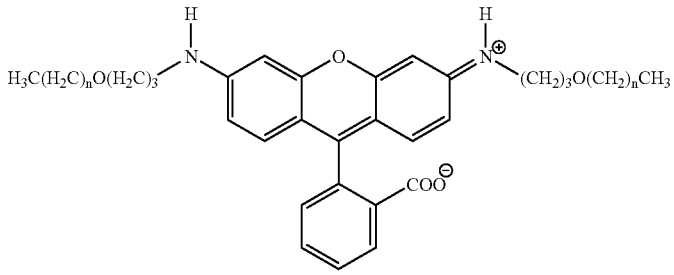

herein n is at least about 11, (b) those of the formulae
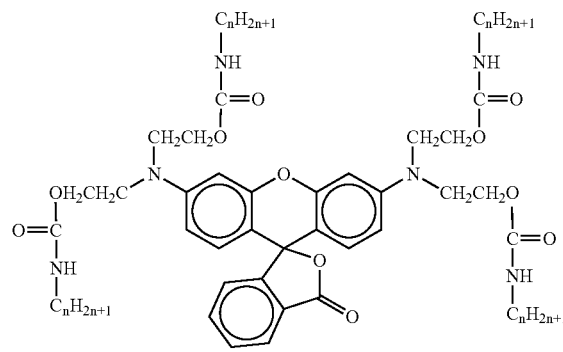
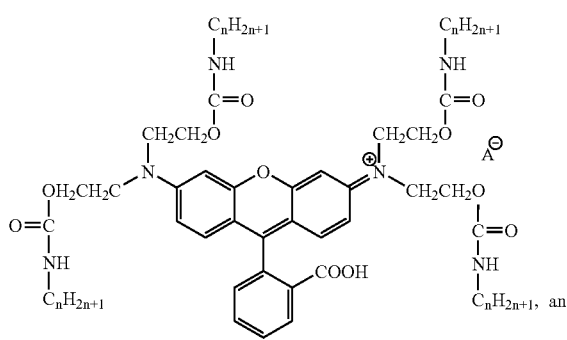
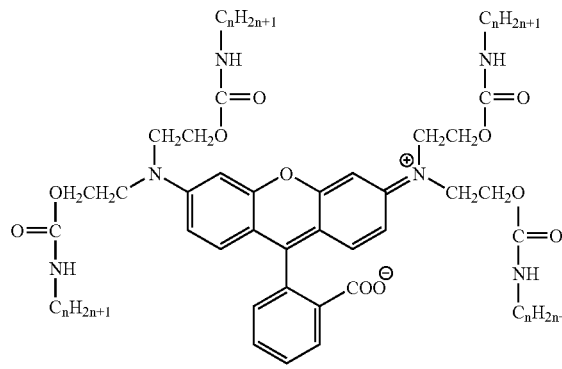
wherein n is at least about 12, (c) those of the formulae
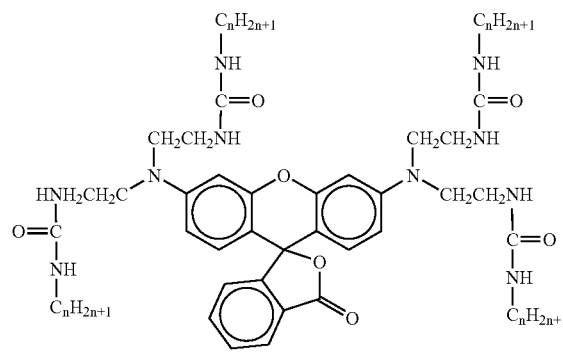
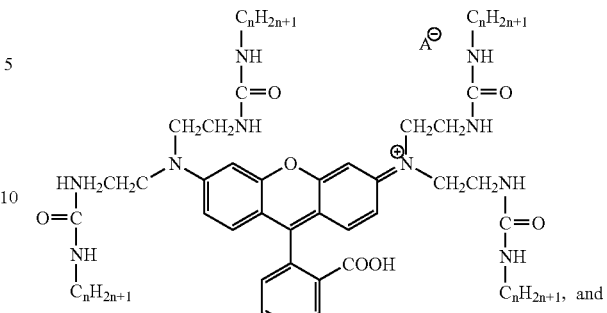
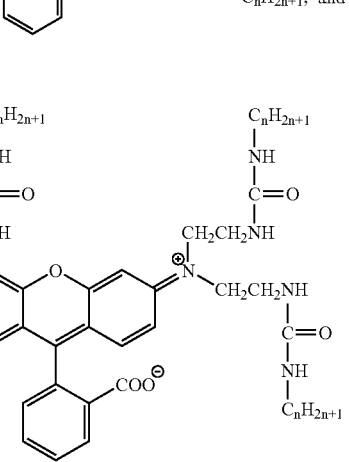
wherein n is at least about 12, (d) those of the formulae
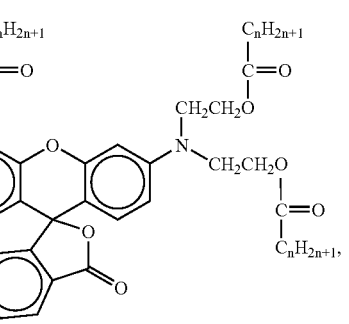
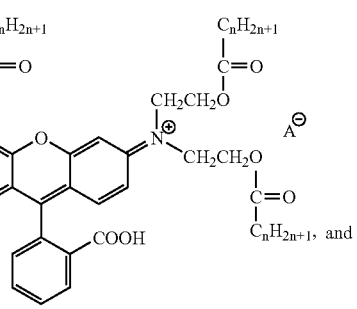

-continued
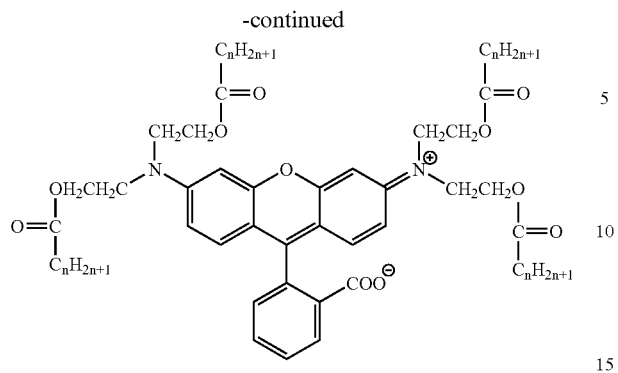
wherein n is at least about 12, (e) those of the formulae
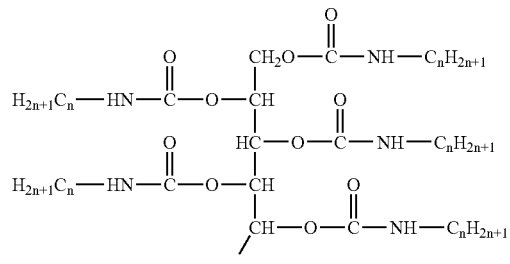
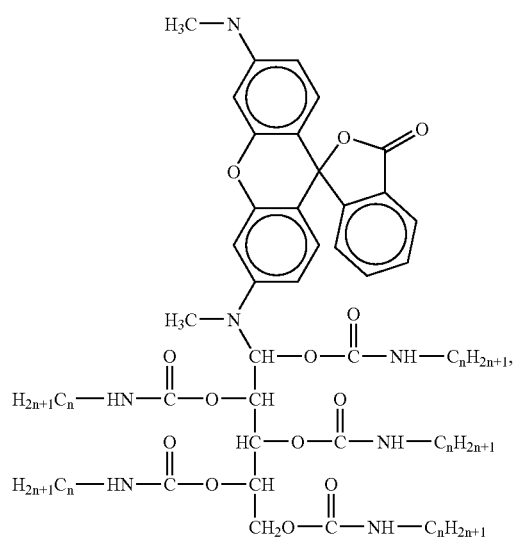
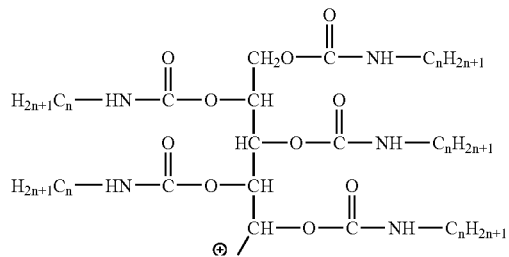
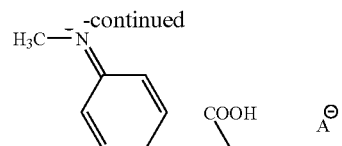
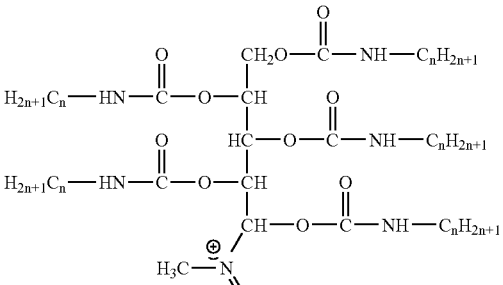
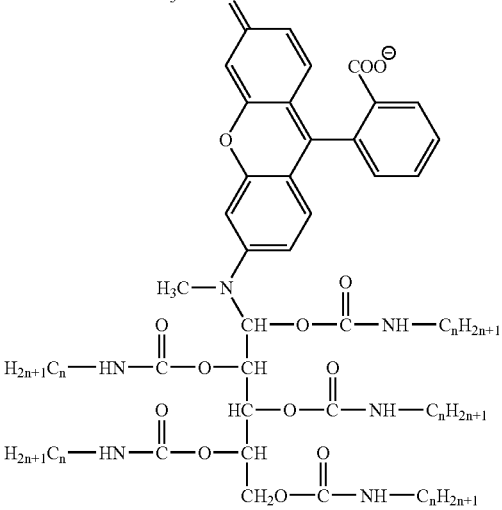
wherein n is at least 12, (f) those of the formulae
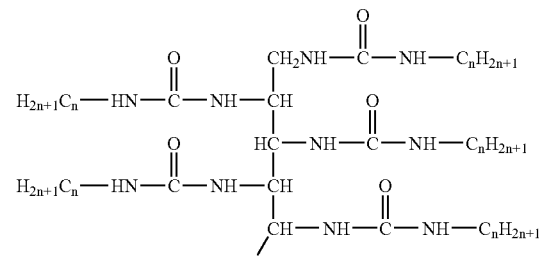

-continued
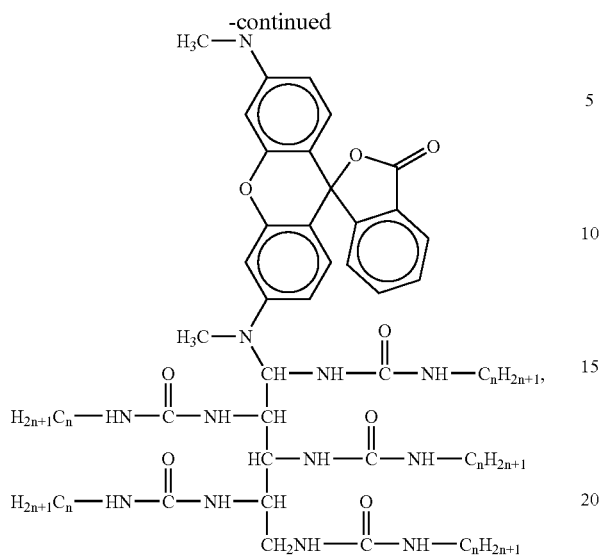
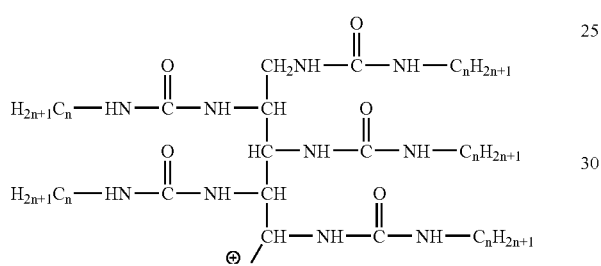
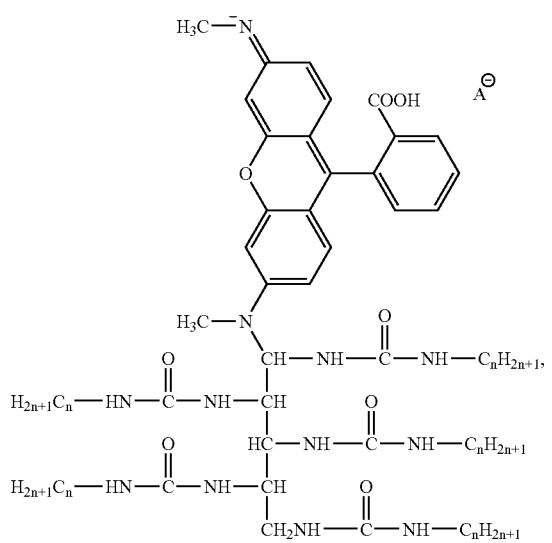
and
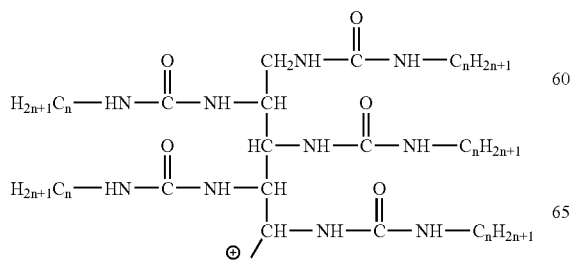
-continued
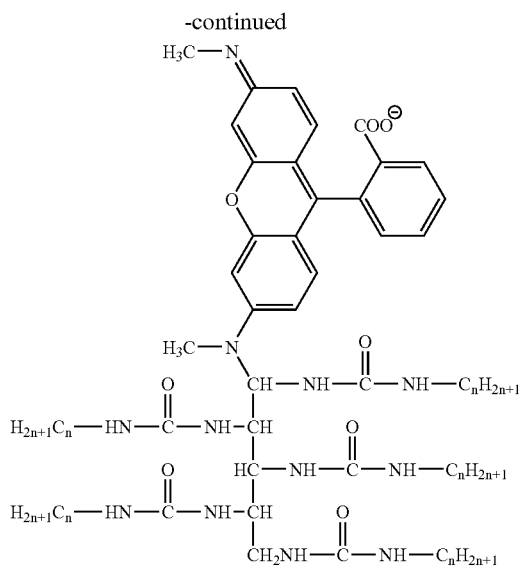
wherein n is at least about 12, (g) those of the formulae
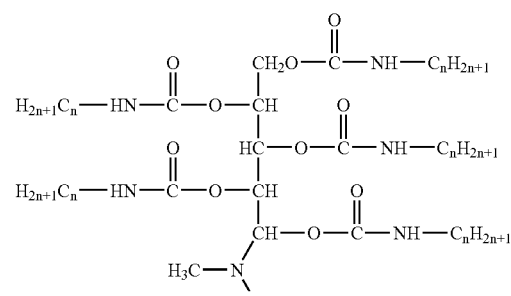
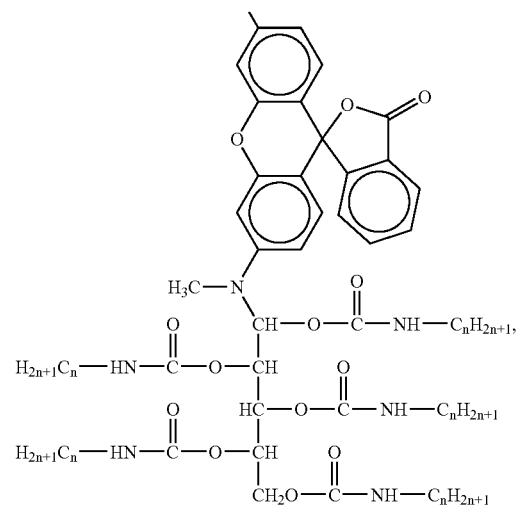

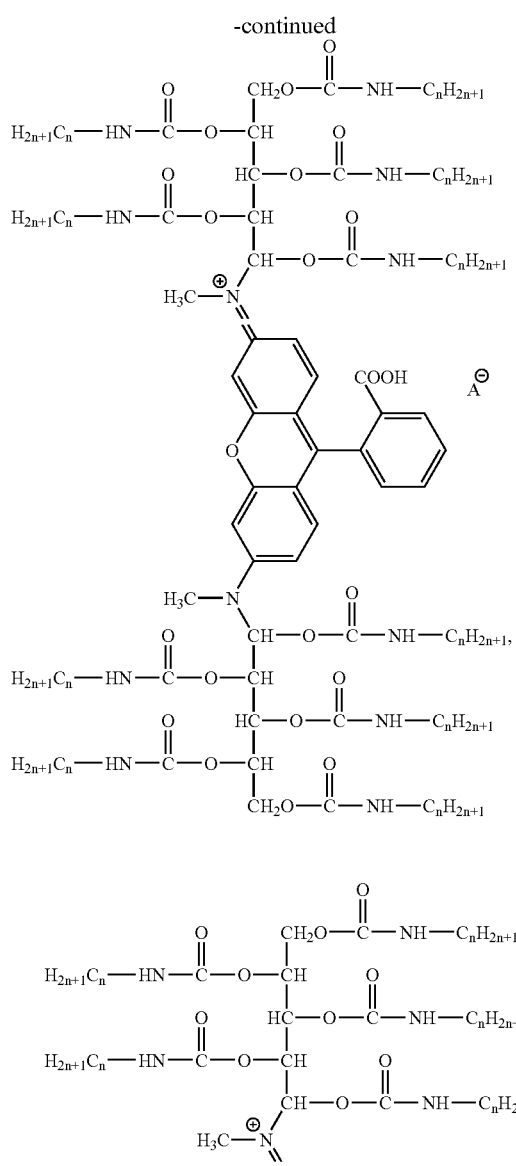
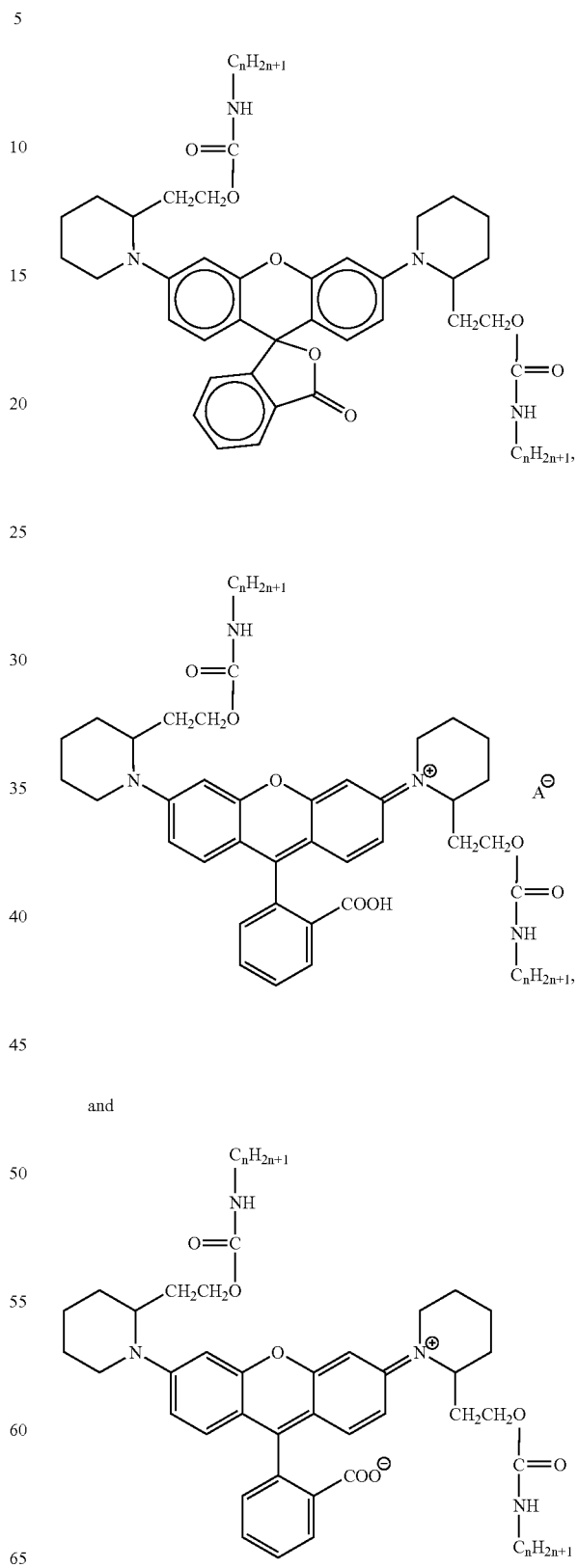
wherein n is at least about 12, (h) those of the formulae wherein n is at least about 12, (i) those of the formulae
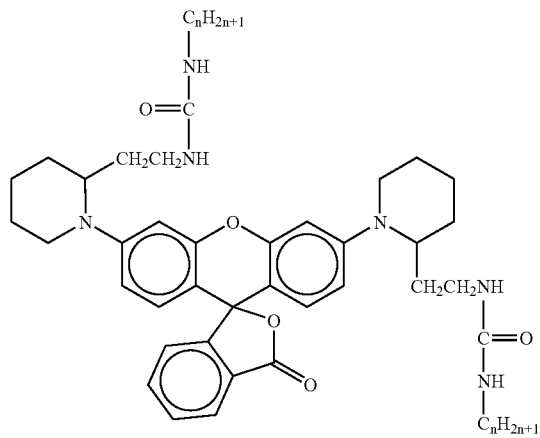
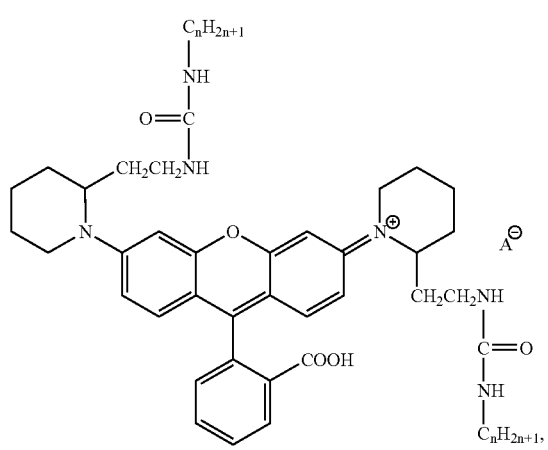
and
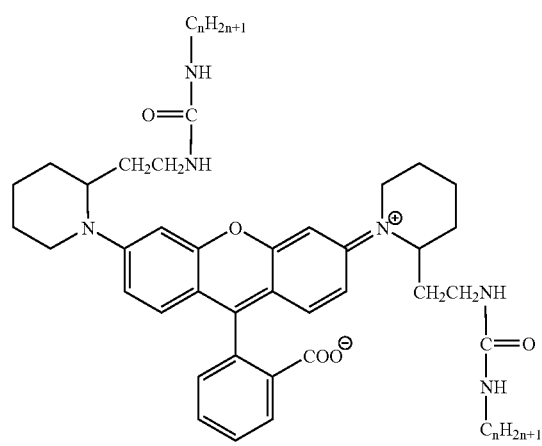
wherein n is at least about 12, (j) those of the formulae
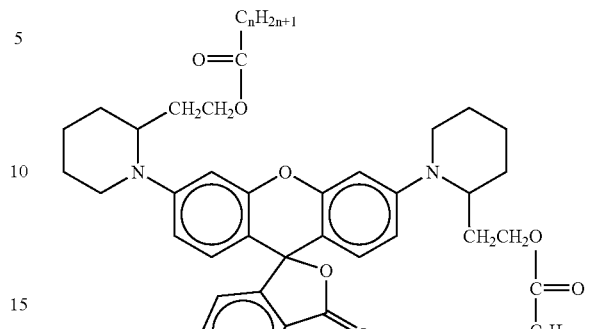
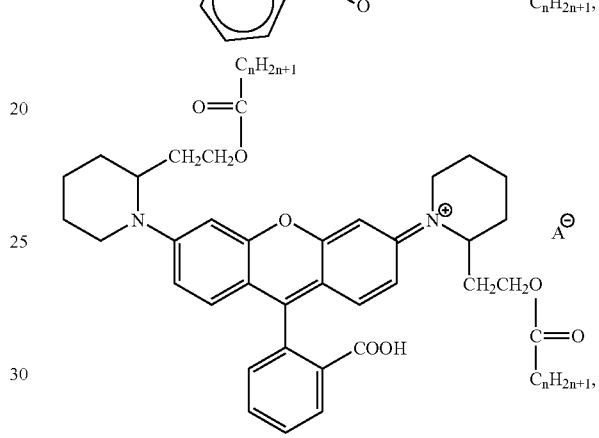
and
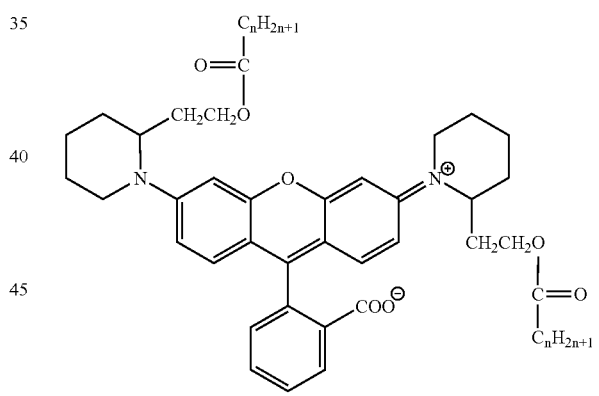
wherein n is at least about 12, (k) those of the formulae
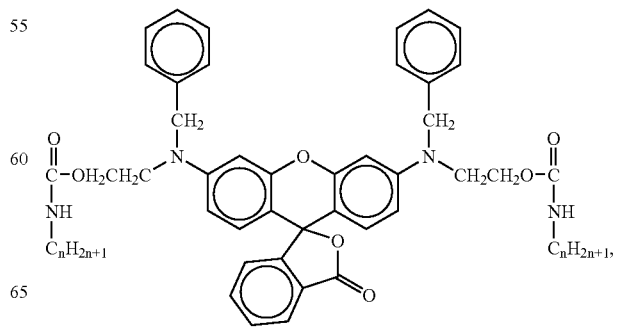

-continued
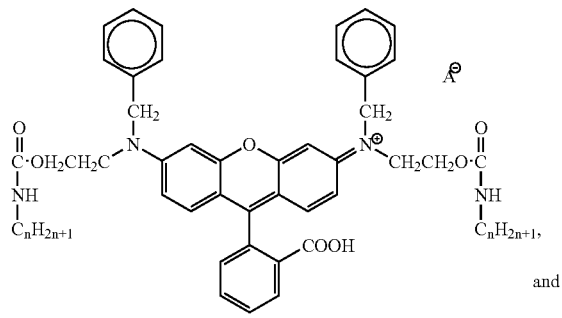
and
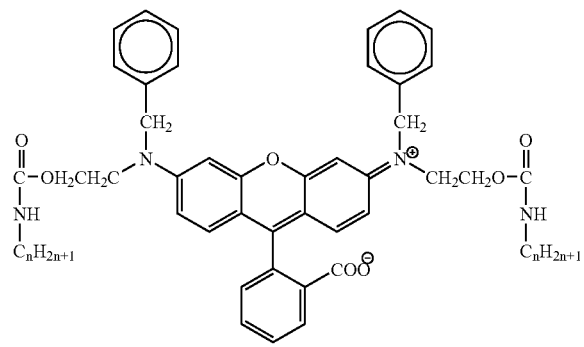
wherein n is at least about 12, (l) those of the formulae
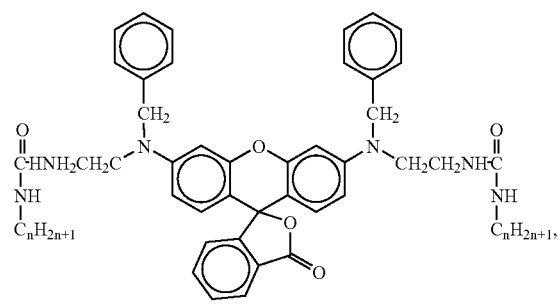
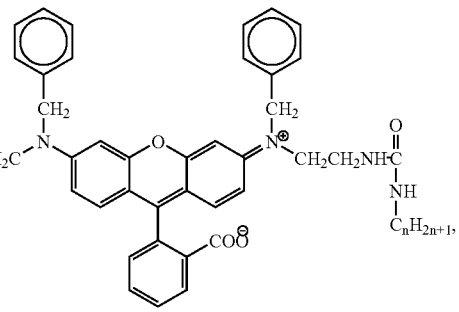
wherein n is at least about 12, (m) those of the formulae
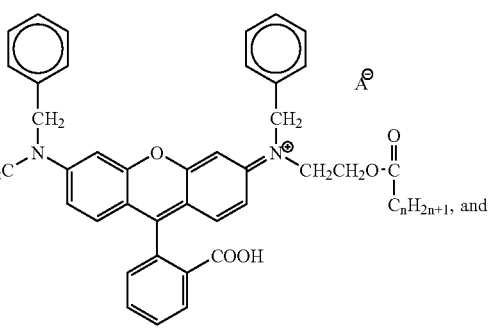
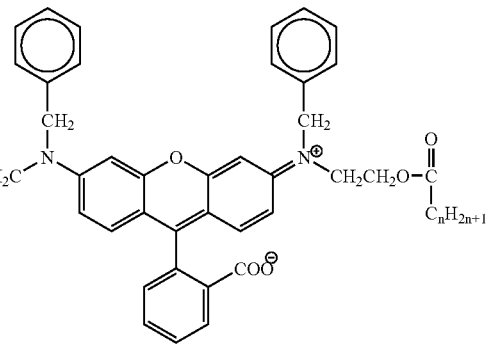

wherein n is at least about 12, (n) those of the formulae
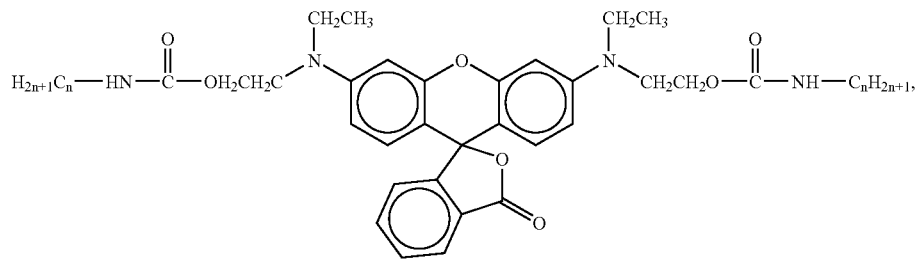
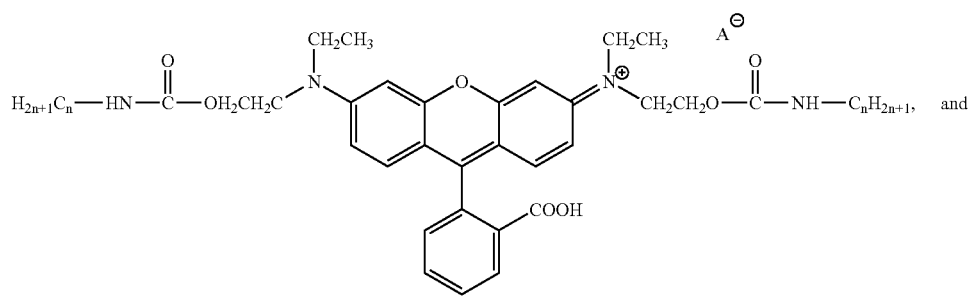
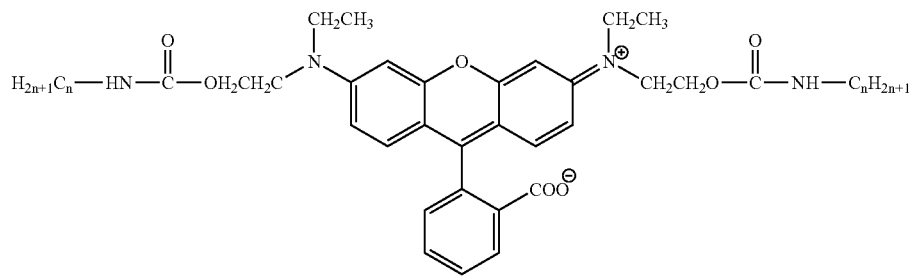
wherein n is at least about 12, (o) those of the formulae
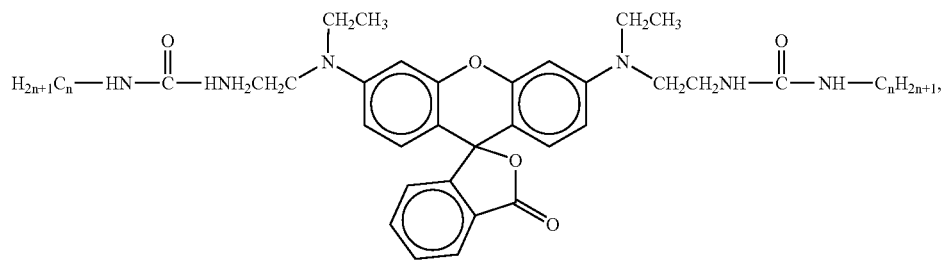
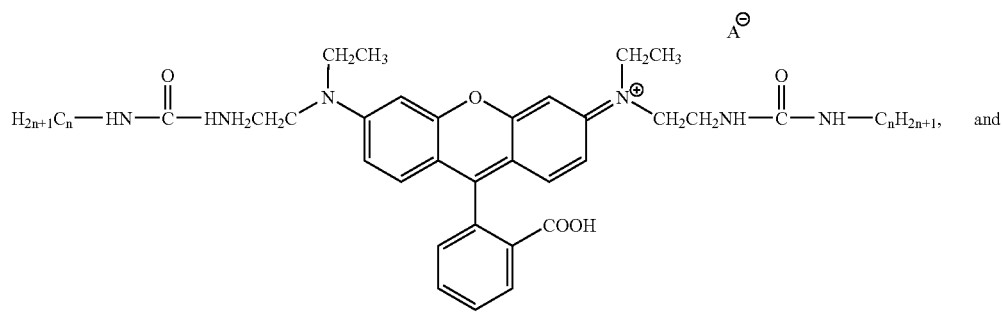

-continued

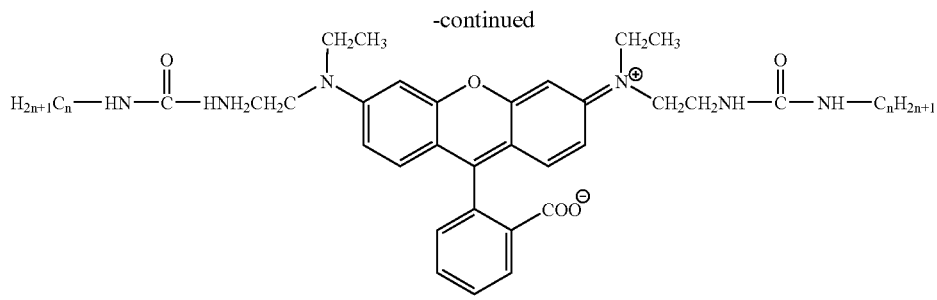

wherein n is at least about 12, (p) those of the formulae

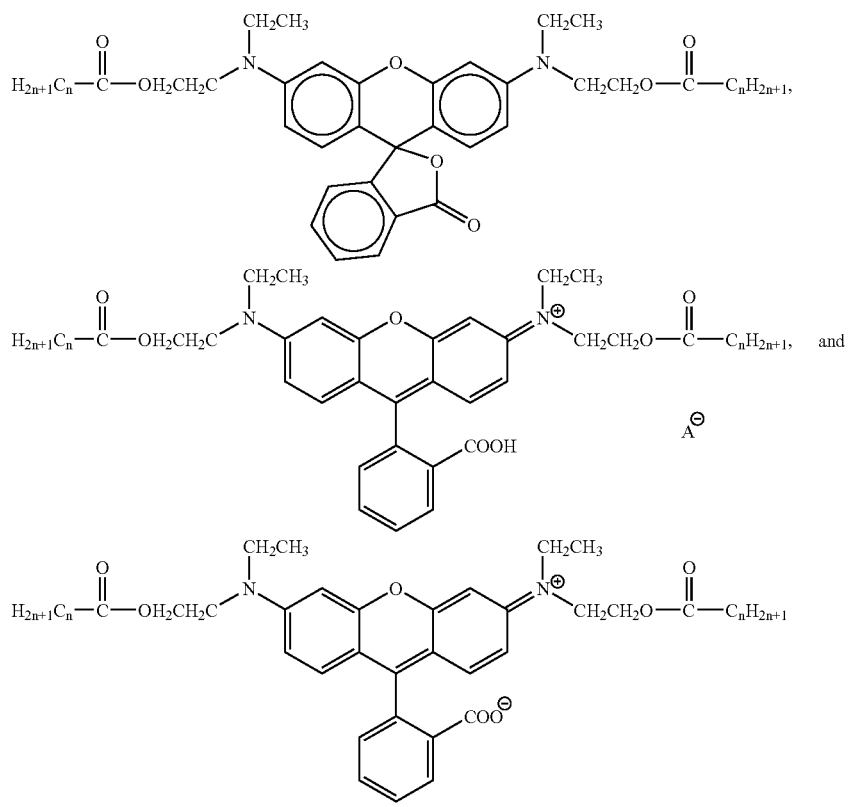

wherein n is at least about 12, and the like.

The chromogen can then be formed into a metal compound colorant by admixing it with an appropriate metal salt, optionally in the presence of a solvent, such as acetone, toluene, methyl isobutyl ketone, or the like. Examples of suitable metals are provided hereinabove. Examples of suitable salts include those formed from the desired metal and the desired organic anion.

The chromogen and the metal salt are present in any desired or effective relative amounts, generally at least about 2 moles of chromogen per every one mole of metal salt, and higher when higher ratios of chromogen to metal or metal containing moiety are desired, although the relative amounts can be outside of these ranges.

When present, the optional solvent is present in any desired or effective amount, in one embodiment at least about 1 liter per every 0.01 mole of chromogen, in another embodiment at least about 1 liter per every 0.04 mole of chromogen, and in yet another embodiment at least about 1 liter per every 0.08 mole of chromogen, and in one embodiment no more than about 1 liter per every 0.5 mole of chromogen, in another embodiment no more than about 1 liter per every 0.1 mole of chromogen, and in yet another embodiment no more than about 1 liter per every 0.09 mole of chromogen, although the relative amounts can be outside of these ranges.

The chromogen and the metal salt are allowed to react for any desired or effective period of time, in one embodiment at least about 0.5 hour, in another embodiment at least about 8 hours, and in yet another embodiment at least about 12 hours, and in one embodiment no more than about 96 hours, in another embodiment no more than about 48 hours, and in yet another embodiment no more than about 24 hours, although the time can be outside of these ranges.

The chromogen and the metal salt are allowed to react at any desired or effective temperature, in one embodiment at least about 25° C., in another embodiment at least about 55° C., and in yet another embodiment at least about 100° C., and in one embodiment no more than about 190° C., in another embodiment no more than about 150° C., and in yet another embodiment no more than about 110° C., although the time can be outside of these ranges. When an optional solvent is used, generally lower temperatures can be employed, whereas when the reaction is run neat, the temperature is sufficiently high to render the chromogen molten.

The resulting product can then be isolated by any desired or effective method, such as by distilling off the solvent, cooling the reaction mixture (when the product is soluble in the solvent at elevated temperatures and insoluble in the solvent at lowered temperatures), or the like.

Another embodiment is directed to a compound comprising the reaction product of (a) a chromogen of the formula

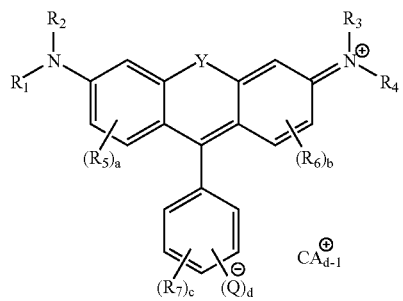

wherein $R_1$, $R_2$, $R_3$, and $R_4$ each, independently of the others, is (i) a hydrogen atom, (ii) an alkyl group, (iii) an aryl group, (iv) an arylalkyl group, or (v) an alkylaryl group, wherein $R_1$ and $R_2$ can be joined together to form a ring, wherein $R_3$ and $R_4$ can be joined together to form a ring, and wherein $R_1$, $R_2$, $R_3$, and $R_4$ can each be joined to a phenyl ring in the central structure, a and b each, independently of the others, is an integer which is 0, 1, 2, or 3, c is an integer which is 0, 1, 2, 3, or 4, each $R_5$, $R_6$, and $R_7$, independently of the others, is (i) an alkyl group, (ii) an aryl group, (iii) an arylalkyl group, (iv) an alkylaryl group, (v) a halogen atom, (vi) an ester group, (vii) an amide group, (viii) a sulfone group, (ix) an amine group or ammonium group, (x) a nitrile group, (xi) a nitro group, (xii) a hydroxy group, (xiii) a cyano group, (xiv) a pyridine or pyridinium group, (xv) an ether group, (xvi) an aldehyde group, (xvii) a ketone group, (xviii) a carbonyl group, (xix) a thiocarbonyl group, (xx) a sulfate group, (xxi) a sulfide group, (xxii) a sulfoxide group, (xxiii) a phosphine or phosphonium group, (xxiv) a phosphate group, (xxv) a mercapto group, (xxvi) a nitroso group, (xxvii) an acyl group, (xxviii) an acid anhydride group, (xxix) an azide group, (xxx) an azo group, (xxxi) a cyanato group, (xxxii) an isocyanato group, (xxxiii) a thiocyanato group, (xxxiv) an isothiocyanato group, (xxxv) a urethane group, or (xxxvi) a urea group, wherein $R_5$, $R_6$, and $R_7$ can each be joined to a phenyl ring in the central structure,

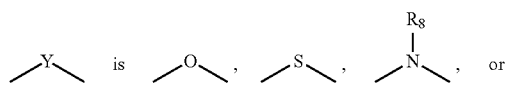

$R_8$, $R_9$, and $R_{10}$ each, independently of the others, is (i) a hydrogen atom, (ii) an alkyl group, (iii) an aryl group, (iv) an arylalkyl group, or (v) an alkylaryl group, provided that the number of carbon atoms in $R_1+R_2+R_3+R_4+R_5+R_6+R_7+R_8+R_9+R_{10}$ is at least about 16, $Q^-$ is a COO— group or a $SO_3$— group, d is an integer which is 1, 2, 3, 4, or 5, A is an organic anion, and CA is either a hydrogen atom or a cation associated with all but one of the $Q^-$ groups, and (b) a metal salt of which the metal portion is either (1) a metal ion having a positive charge of +y wherein y is an integer which is at least 2, said metal ion being capable of forming a compound with at least two

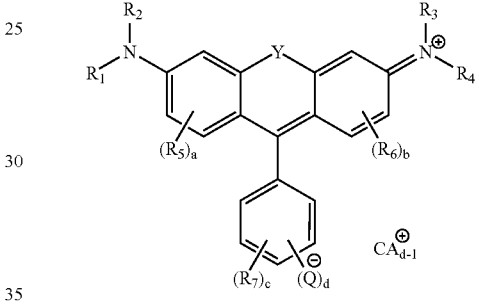

moieties, or (2) a metal-containing moiety capable of forming a compound with at least two

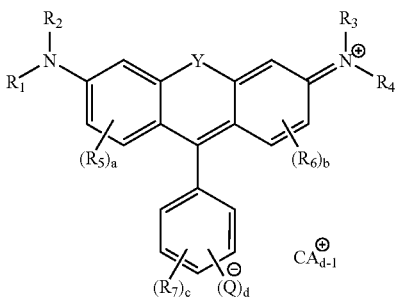

moieties.

While not being limited to any particular theory, it is believed that in at least some embodiments and with at least some metal cations or metal-containing moieties, coordination complexes may form. For example, when Q is a carboxylate anion, d is 1, and the metal is capable of coordinating to four ligands, a metal colorant compound as disclosed herein may have the formula

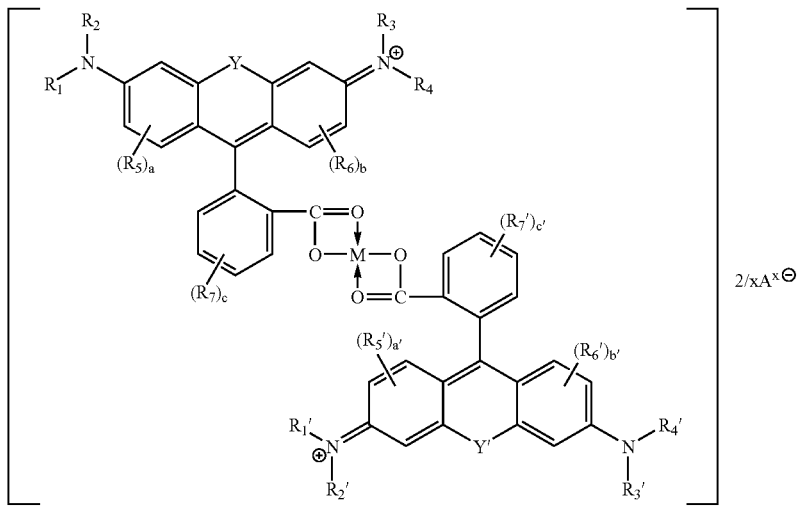

wherein the arrowheaded bonds represent coordination bonds between lone pairs of electrons on a carbonyl group and the metal. For example, when M is a metal that makes square planar coordination complexes, the metal colorant compound may have the structure When M is a metal that makes tetrahedral coordination complexes, the metal colorant compound may have the structure

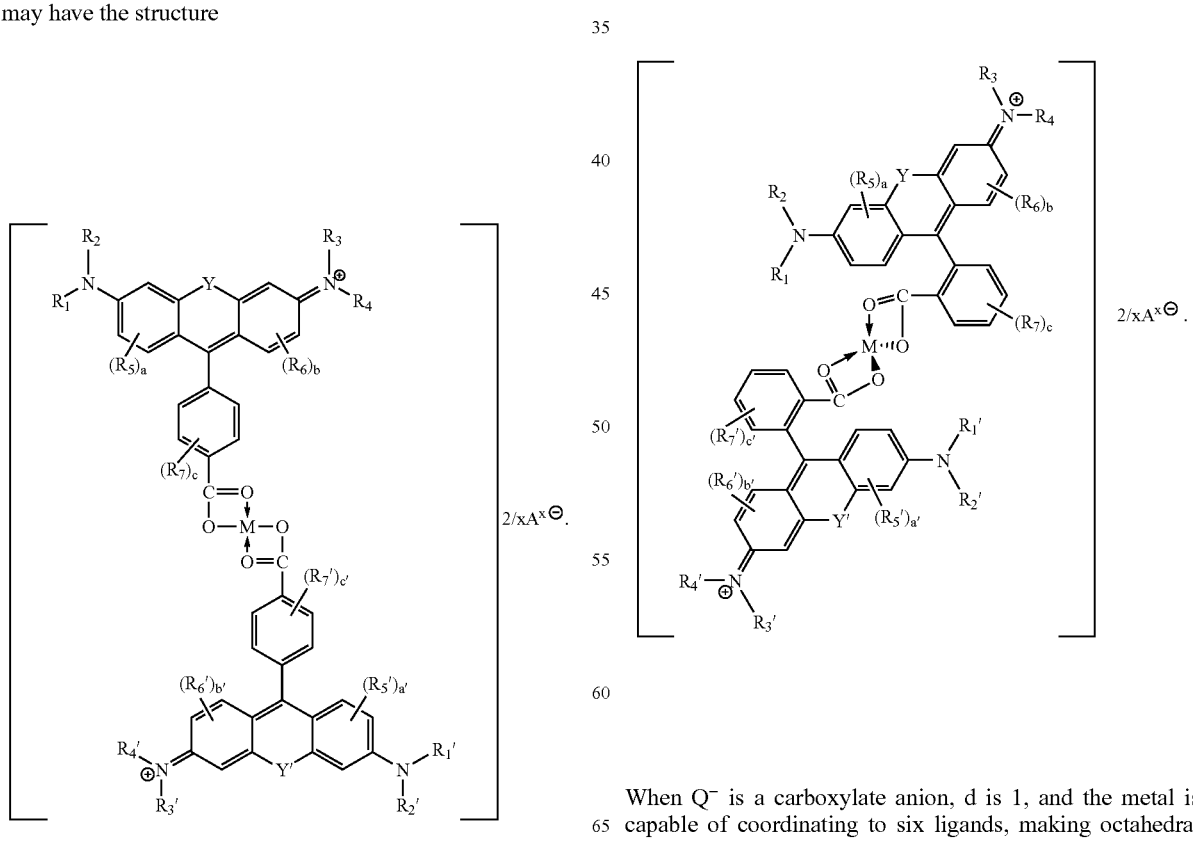

When $Q^-$ is a carboxylate anion, d is 1, and the metal is capable of coordinating to six ligands, making octahedral coordination complexes, the metal colorant compound may have the structure

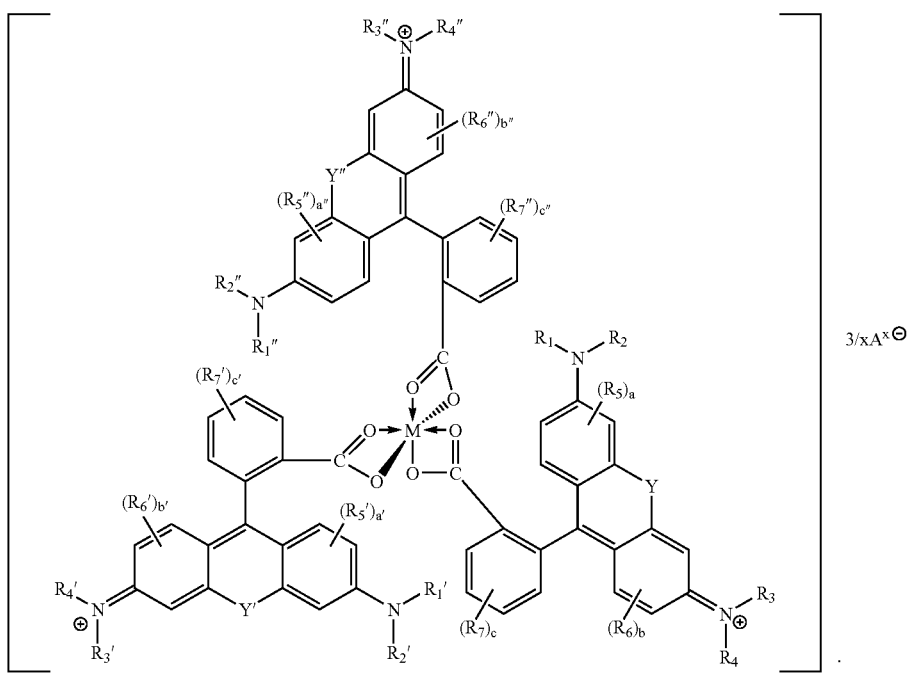

It is believed that sulfonate anions will form complexes similar to those formed by carboxylate anions.

Specific embodiments will now be described in detail. These examples are intended to be illustrative, and the claims are not limited to the materials, conditions, or process parameters set forth in these embodiments. All parts and percentages are by weight unless otherwise indicated.

Example IA

Synthesis of Dichlorofluorescein

A mixture of fluorescein (100 grams, 0.331 mole; obtained from Aldrich Chemical Co., Milwaukee, Wis.) and $PCl_5$ (128.5 grams, 0.62 mole; obtained from Aldrich Chemical Co.) in 650 milliliters of chlorobenzene was stirred and heated to 140° C. in a 1 liter round bottom flask equipped with a reflux condenser. After 6 hours of heating, the reflux condenser was replaced with a distillation setup, and $POCl_3$ formed during the reaction as well as the chlorobenzene were distilled off. After all of the $POCl_3$ and chlorobenzene were removed, 300 grams of N-methyl pyrrolidinone was added and the resulting mixture was heated to 100° C. with stirring until all of the crude dichlorofluorescein dissolved. The solution was then poured into a 4 liter beaker containing 1 liter of deionized water, A tan solid precipitated out and was collected on a filter and dried in a vacuum oven. The final tan solid matched the IR, NMR, and TLC of commercially available dichlorofluorescein.

Other synthetic processes can also be used. For example, a one-pot process using DMF solvent can be employed wherein the $POCl_3$ intermediate is not distilled off but is removed by reaction with methanol, which also precipitates the dichlorofluorescein as a white solid. Methods using toluenesulfonylchloride, a less reactive and corrosive chlorinating agent than $PCl_5$, can also be used.

Example IB

Synthesis of Tetrastearyl Colorant

A mixture of dichlorofluorescein (105 grams, 0.284 mole, prepared as described above), calcium oxide (24 grams, 0.62 mole; obtained from Aldrich Chemical Co., Milwaukee, Wis.), $ZnCl_2$ (116 grams, 0.85 mole; obtained from Aldrich Chemical Co.), and distearyl amine (288 grams, 0.585 mole; ARMEEN 2HT, obtained from Akzo-Nobel, McCook, Ill.) in 650 milliliters of tetramethylene sulfone (obtained from Chevron Phillips Chemical Co., LP, The Woodlands, Tex.) was stirred and heated to 190° C. in a 1 liter round bottom flask. After 10 hours of heating, the deeply magenta colored mixture was cooled to 120° C. and poured into 2.5 liters of methyl isobutyl ketone (MIBK) and stirred until totally dissolved.

Example IC

Purification of Tetrastearyl Colorant

The solution of crude tetrastearyl colorant in MIBK was then transferred to a 4 liter separatory funnel. Three aqueous EDTA washes were then performed (50 grams of the tetrasodium salt of EDTA in 1,000 milliliters of water for each wash) to remove all of the zinc and calcium salts in the crude reaction product. The product, dissolved in MIBK, remained on the top layer with the water/EDTA chelated metal waste on the bottom layer, which was discarded. Two washes with deionized water (1 liter each) were then performed. At this point, the MIBK solution was no longer magenta, but a faint orangeish-red color. The lack of a brilliant magenta color at this point indicated a ring-closed, or free base, form of the colorant, believed to be of the formula

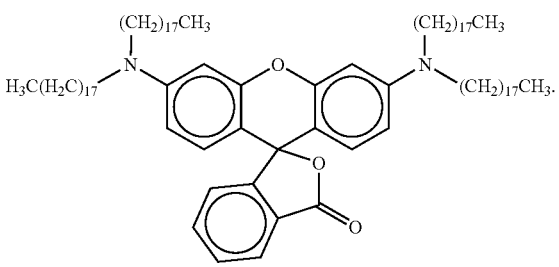

Example ID

Isolation of Tetrastearyl Colorant

The solution of the ring-closed, purified tetrastearyl colorant in MIBK was then transferred to a 2 liter round bottom flask with distillation setup. The MIBK and residual water were distilled off and the product, a slightly viscous wax when hot, was transferred to a jar and allowed to harden. The wax was a deep red colored, somewhat hard wax when cooled to room temperature.

Example IE

Protonation of Tetrastearyl Colorant 250 grams of the solid, ring-closed, purified tetrastearyl colorant prepared in Example ID was then transferred to a 1 liter beaker and 500 milliliters of MIBK were added and allowed to dissolve the solid with stirring. A stoichiometric amount of dodecyl benzene sulfonic acid was added to this solution and stirred for 1 hour. A deep magenta hue was observed with the addition of the acid. The solution was then transferred to a distillation setup and the MIBK removed. The molten ring-opened waxy colorant was then transferred to an aluminum tin and allowed to cool to room temperature. The ring-opened, or protonated, or free-base form of this colorant is believed to be of the formula

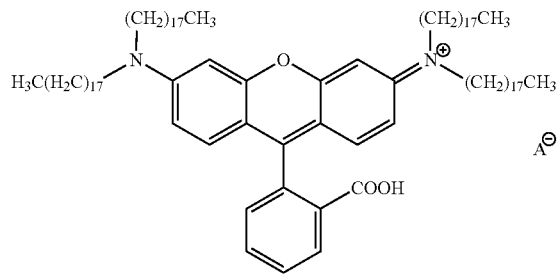

wherein A is the anion corresponding to the acid used for protonaton. The zwitterionic form of this colorant is believed to be of the formula

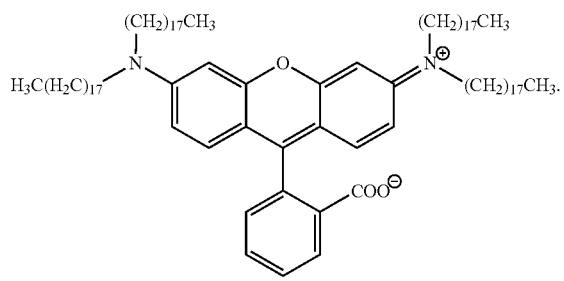

The process was repeated a number of times substituting for dodecyl benzene sulfonic acid the following acids: p-toluene sulfonic acid; hydrochloric acid; trifluoroacetic acid; methyl sulfonic acid; trifluoromethyl sulfonic acid; and hydrobromic acid. Similar results were observed in all cases.

Example IF

Preparation of Isolated Zinc Tetrastearyl Colorant

To a 1-liter 3-necked roundbottom flask with TEFLON® coated magnet and silicone oil bath was added 229 grams of the ring-closed purified tetrastearyl chromogen and 200 grams of MIBK. The mixture was heated to reflux. Thereafter, about 12.2 grams of $ZnCl_2$ (obtained from Aldrich Chemical Co., Milwaukee, Wis.) was added in a stoichiometric amount of one mole of zinc chloride per every 2 moles of tetrastearyl chromogen. The solution was stirred for about 18 hours. Thereafter, the MIBK was distilled off. The product, a slightly viscous wax when warm, was transferred to a jar and allowed to harden. At room temperature, the product was a deep magenta/red colored somewhat hard wax, believed to be a coordination compound of the formula

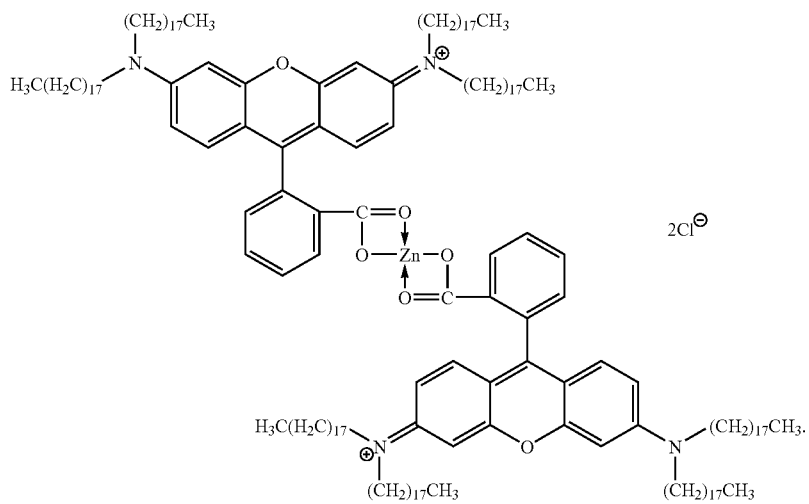

Example IG

Synthesis of Tetrastearyl Chromogen

A mixture of dichlorofluorescein (105 grams, 0.284 mole, prepared as described in Example IA), calcium oxide (24 grams, 0.62 mole; obtained from Aldrich Chemical Co., Milwaukee, Wis.), $ZnCl_2$ (116 grams, 0.85 mole; obtained from Aldrich Chemical Co.), and distearyl amine (288 grams, 0.585 mole; ARMEEN 2HT, obtained from Akzo-Nobel, McCook, Ill.) in 650 milliliters of tetramethylene sulfone (obtained from Chevron Phillips Chemical Co., LP, The Woodlands, Tex.) was stirred and heated to 190° C. in a 1 liter round bottom flask. After 10 hours of heating, the deeply magenta colored mixture was cooled to 150° C. and poured onto a flat tray to cool further and solidify.

Example IH

Purification of Tetrastearyl Chromogen

The crude mixture produced in Example IG was then added to 5 liters of glacial acetic acid. The mixture was stirred and heated to reflux (120° C.). After 1 hour of refluxing, the mixture was cooled to 80° C. The mixture was then slowly poured into 9 liters of deionized water while stirring. Ice was added during the addition to keep the water temperature below 28° C. When addition was complete, the mixture was allowed to stir for 30 minutes. Thereafter, the reaction mixture was filtered using a large Buchner funnel and 4 liter side arm vacuum flask. The filtered solids were added to 12 liters of deionized water, stirred for 30 minutes, and filtered. This water wash procedure was repeated one additional time. The filtered solids were then added to 12 liters of methanol, stirred for 30 minutes, and filtered. The recovered magenta powder was placed in a tray and allowed to air dry.

Example IJ

Preparation of Zinc Tetrastearyl Colorant

To a 2-liter 3-necked roundbottom flask with TEFLON® coated magnetic stir bar in a silicone oil bath is added 229 grams of the ring-closed purified tetrastearyl chromogen prepared as described in Example ID and 600 grams of MIBK. The mixture is heated to reflux. Thereafter, about 372 grams of zinc stearate (available from Aldrich Chemical Co., Milwaukee, Wis.) is added in a stoichiometric amount of 2 moles of zinc stearate per every one mole of tetrastearyl chromogen. The solution is stirred for about 18 hours. Thereafter, the MIBK is distilled off. The product is transferred to a jar and allowed to harden. It is believed that the product will be a deep magenta/red colored somewhat hard wax, believed to be a coordination compound of the formula

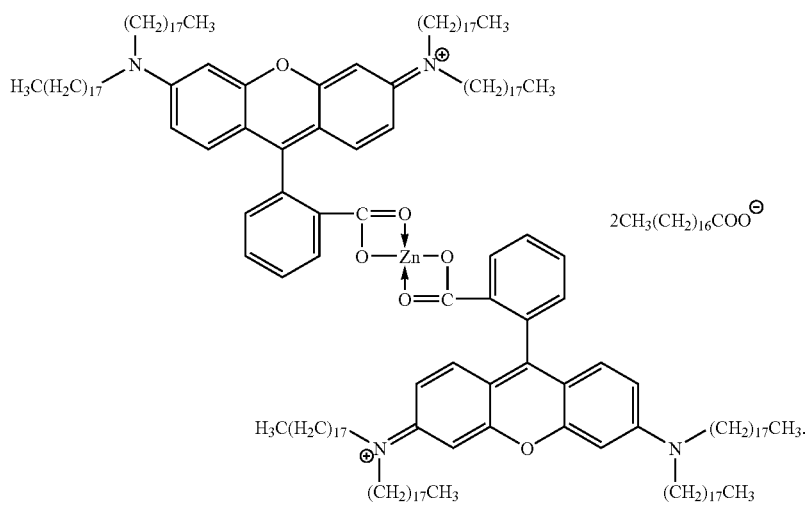

Example IIB

The process of Example IB was repeated except that dioctyl amine ($NH((CH_2)_7CH_3)_2$, obtained from Aldrich Chemical Co., Milwaukee, Wis.) was used instead of distearyl amine. The dioctyl amine was present in an amount of 1.95 moles of dioctyl amine per every one mole of dichlorofluorescein.

Example IIC

The process of Example IC was repeated using the product obtained in Example IIB. It is believed that the purified product was of the formula

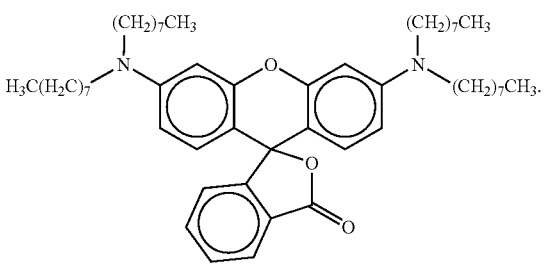

The ring-opened, or protonated, or free-base form of this chromogen is believed to be of the formula

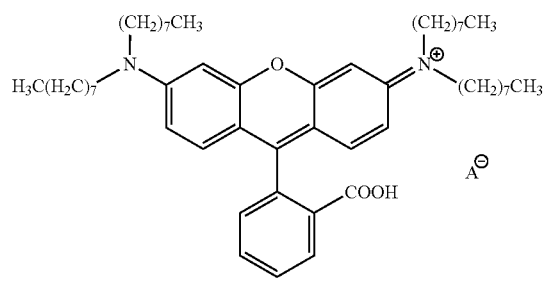

wherein A is the anion corresponding to the acid used for protonaton. The zwitterionic form of this chromogen is believed to be of the formula

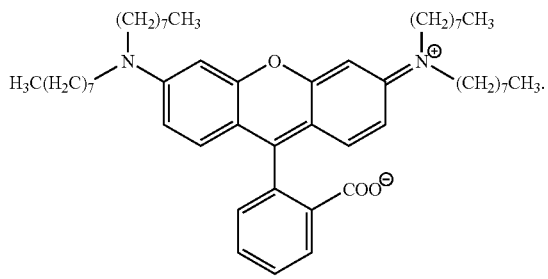

Example IID

The process of Example ID was repeated using the product obtained in Example IIC.

Example IIIB

The process of Example IB was repeated except that the reaction was run with 2.05 moles of stearyl amine per every one mole of dichlorofluorescein.

Example IIIC

The process of Example IC was repeated using the product obtained in Example IIIB. It is believed that the purified product was of the formula

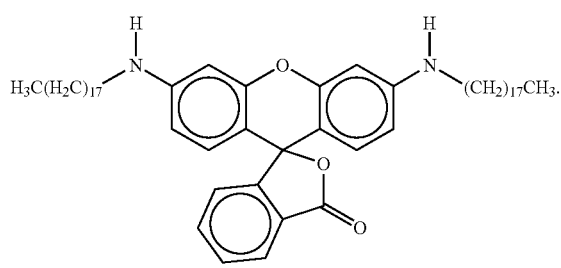

The ring-opened, or protonated, or free-base form of this chromogen is believed to be of the formula

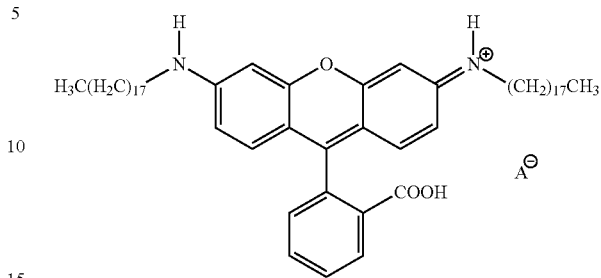

wherein A is the anion corresponding to the acid used for protonaton. The zwitterionic form of this chromogen is believed to be of the formula

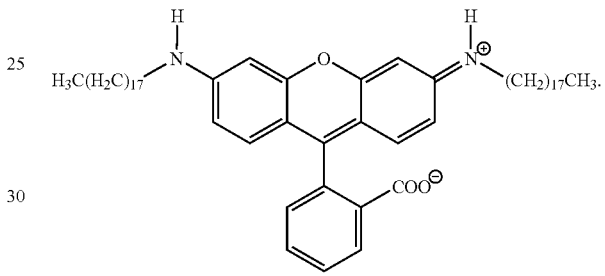

Example IIID

The process of Example ID was repeated using the product obtained in Example IIIC.

Example IVB

The process of Example IB was repeated except that PRIMENE JM-T (obtained from Rohm and Haas Company, Philadelphia, Pa.), of the formula

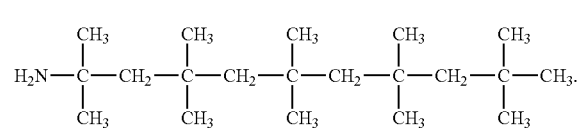

was used instead of distearyl amine. The PRIMENE JM-T was present in an amount of 2 moles of PRIMENE JM-T per every one mole of dichlorofluorescein.

Example IVC

The process of Example IC was repeated using the product obtained in Example IVB. It is believed that the purified product was of the formula

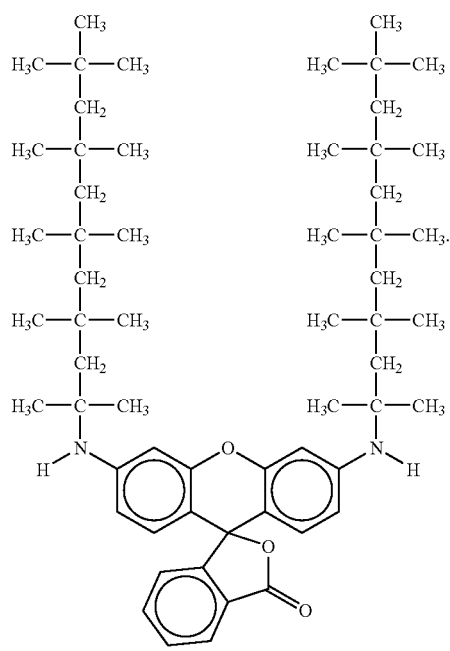

The ring-opened, or protonated, or free-base form of this chromogen is believed to be of the formula

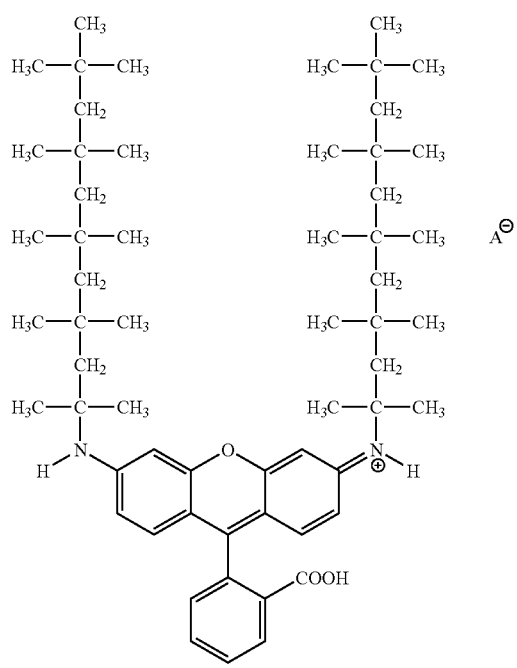

wherein A is the anion corresponding to the acid used for protonaton. The zwitterionic form of this chromogen is believed to be of the formula

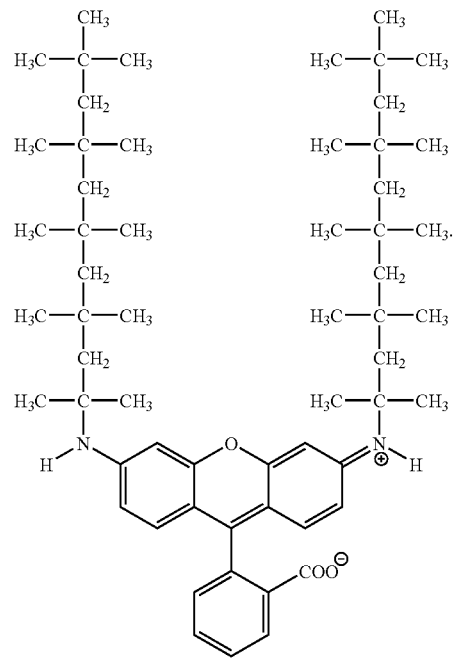

Example IVD

The process of Example ID was repeated using the product obtained in Example IVC.

Example VB

The process of Example IB was repeated except that UNILIN 425-PA (obtained from Tomah Products, Milton, Wis., of the formula $CH_3(CH_2)_{31}$—O—$CH_2CH_2CH_2NH_2$) was used instead of distearyl amine. The UNILIN 425-PA was present in an amount of 2 moles of UNILIN 425-PA per every one mole of dichlorofluorescein, It is believed that the product was of the formula

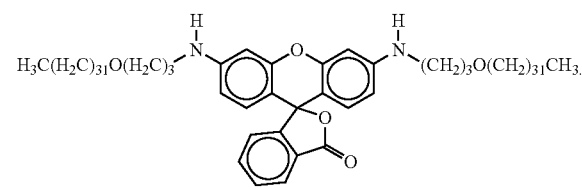

The ring-opened, or protonated, or free-base form of this chromogen is believed to be of the formula

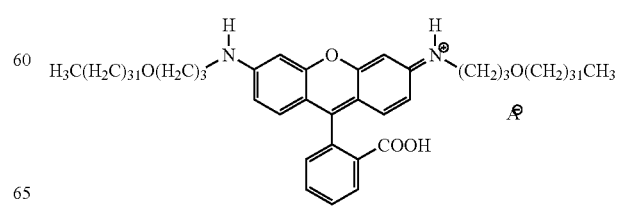

wherein A is the anion corresponding to the acid used for protonaton. The zwitterionic form of this chromogen is believed to be of the formula

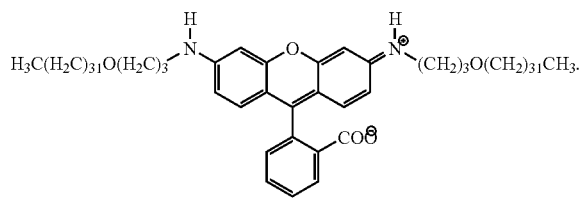

Example VIB

The process of Example IB was repeated except that diethanol amine (obtained from Aldrich Chemical Co., Milwaukee, Wis., of the formula $HN(CH_2CH_2OH)_2$) was used instead of distearyl amine. The diethanol amine was present in an amount of 2.5 moles of diethanol amine per every one mole of dichlorofluorescein. In addition, 2 moles of zinc chloride were used per every one mole of dichlorofluorescein and 1 mole of calcium oxide was used per every one mole of dichlorofluorescein, the solvent was N-methyl pyrrolidone instead of tetramethylene sulfone, and the reaction mixture was heated to 125° C. for 100 hours.

Example VIC

The process of Example IC was repeated using the product obtained in Example VIB except that the product was poured into methanol and sufficient EDTA was added to remove all of the $Zn^{2+}$ and $Ca^{2+}$ ions. It is believed that the purified product was of the formula

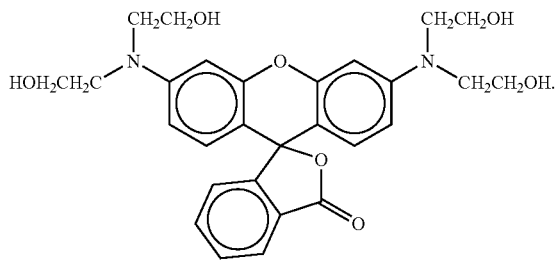

Example VIC-1

About 10 grams of the product obtained in Example VIC is added to 23.4 grams of octadecylisocyanate (available from Aldrich Chemical Co., Milwaukee, Wis.) at 120° C., after which 2 drops of dibutyltindilaurate catalyst (available from Aldrich Chemical Co.) is added and the reaction is stirred and heated until disappearance of the isocyanate peak in the IR is observed. The tetraurethane rhodamine is poured into aluminum tins and is believed to be of the formula

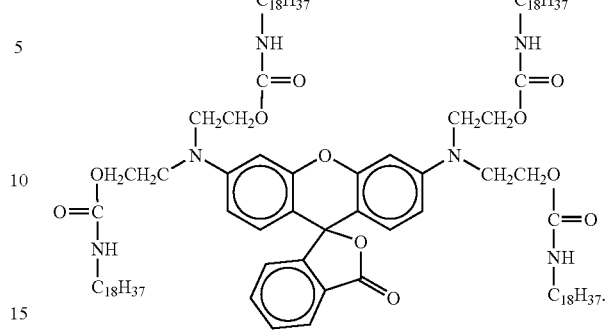

The ring-opened, or protonated, or free-base form of this chromogen is believed to be of the formula

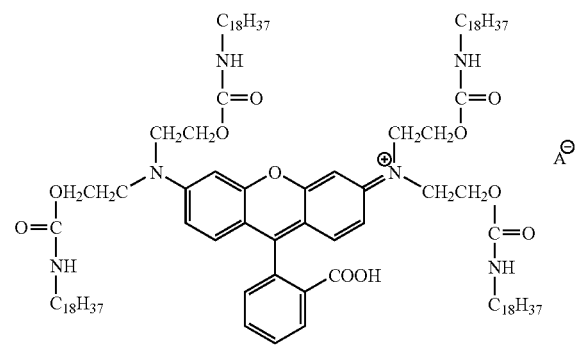

wherein A is the anion corresponding to the acid used for protonaton. The zwitterionic form of this chromogen is believed to be of the formula

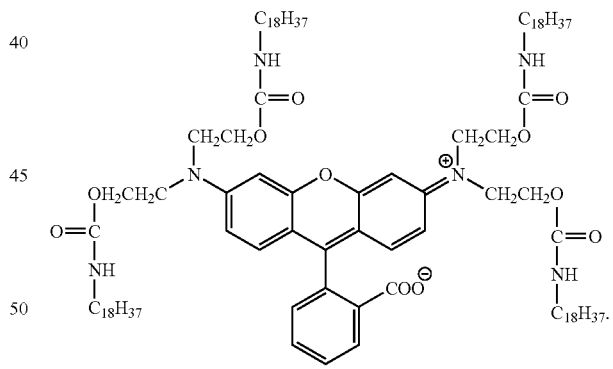

Example VIIB

The process of Example IB was repeated except that N-methyl-D-glucamine (obtained from Aldrich Chemical Co., Milwaukee, Wis.), of the formula

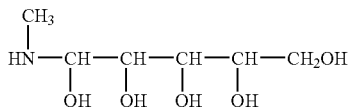

was used instead of distearyl amine. The N-methyl-D-glucamine was present in an amount of 2.5 moles of N-methyl-D-glucamine per every one mole of dichlorofluorescein. In addition, 2 moles of zinc chloride were used per every one mole of dichlorofluorescein and 1.5 moles of calcium oxide was used per every one mole of dichlorofluorescein, the solvent was N-methyl pyrrolidone instead of tetramethylene sulfone, and the reaction mixture was heated to 130° C. for 7 days.

Example VIIC

The process of Example IC was repeated using the product obtained in Example VIIB except that the product was poured into methanol and sufficient EDTA was added to remove all of the $Zn^{2+}$ and $Ca^{2+}$ ions. It is believed that the purified product was of the formula

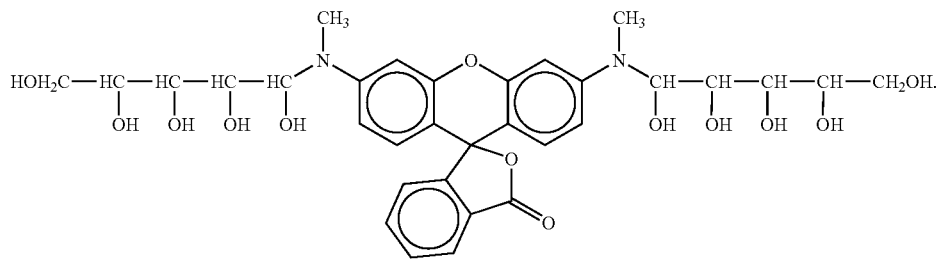

Example VIIC-1

About 10 grams of the product obtained in Example VIIC is added to 45 grams of octadecylisocyanate (available from Aldrich Chemical Co., Milwaukee, Wis.) at 120° C., after which 4 drops of dibutyltindilaurate catalyst (available from Aldrich Chemical Co.) is added and the reaction is stirred and heated until disappearance of the isocyanate peak in the IR is observed. The deca-urethane rhodamine is poured into aluminum tins and is believed to be of the formula

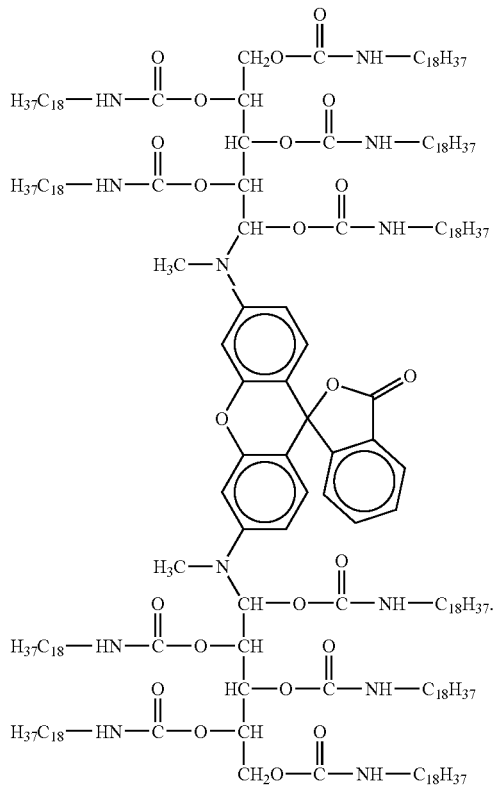

The ring-opened, or protonated, or free-base form of this chromogen is believed to be of the formula

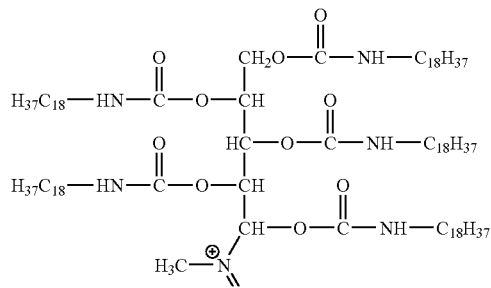

-continued

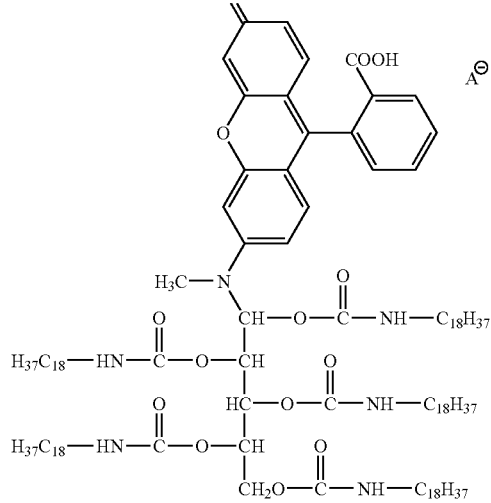

wherein A is the anion corresponding to the acid used for protonaton. The zwitterionic form of this chromogen is believed to be of the formula

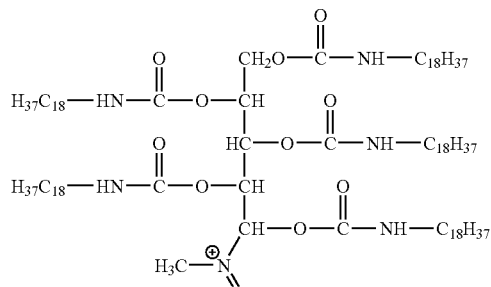

-continued

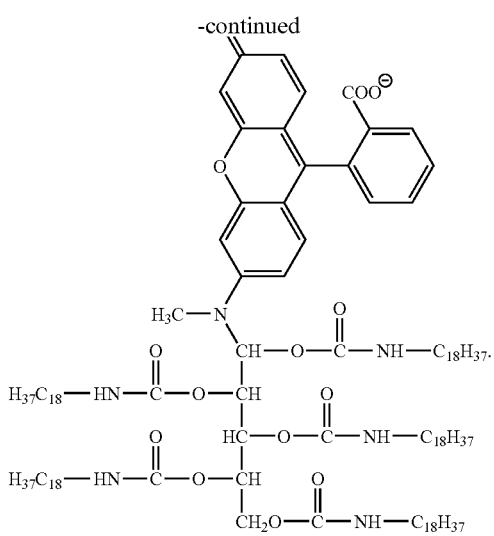

Example VIIIB

The process of Example IB was repeated except that 2-piperidine ethanol (obtained from Aldrich Chemical Co., Milwaukee, Wis.), of the formula

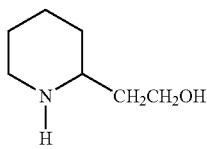

was used instead of distearyl amine. The 2-piperidine ethanol was present in an amount of 2.5 moles of 2-piperidine ethanol per every one mole of dichlorofluorescein. In addition, 2 moles of zinc chloride were used per every one mole of dichlorofluorescein and 1 mole of calcium oxide was used per every one mole of dichlorofluorescein, the solvent was N-methyl pyrrolidone instead of tetramethylene sulfone, and the reaction mixture was heated to 160° C. for 24 hours. The reaction product was then poured into water and filtered and washed with water. It is believed that the product was of the formula

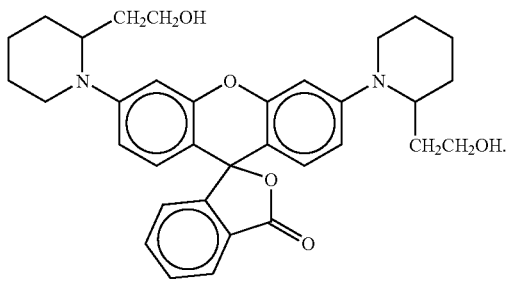

Example VIIIC-1

About 10 grams of the product obtained in Example VIIIB is added to 10.7 grams of octadecylisocyanate (available from Aldrich Chemical Co., Milwaukee, Wis.) at 120° C., after which 1 drop of dibutyltindilaurate catalyst (available from Aldrich Chemical Co.) is added and the reaction is stirred and heated until disappearance of the isocyanate peak in the IR is observed. The di-urethane rhodamine is poured into aluminum tins and is believed to be of the formula

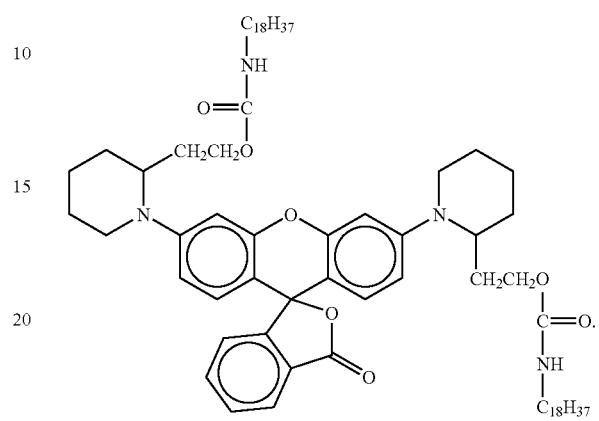

The ring-opened, or protonated, or free-base form of this chromogen is believed to be of the formula

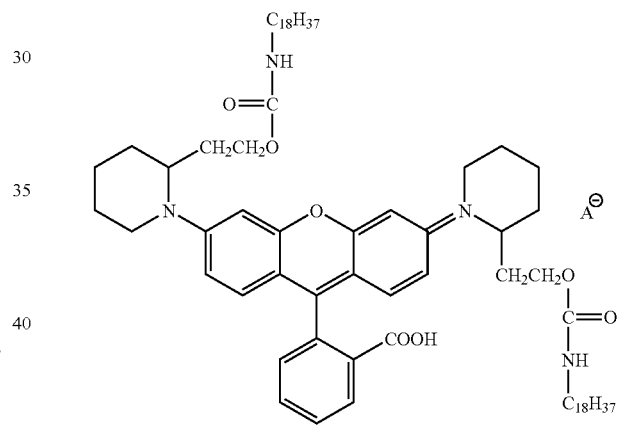

wherein A is the anion corresponding to the acid used for protonaton. The zwitterionic form of this chromogen is believed to be of the formula

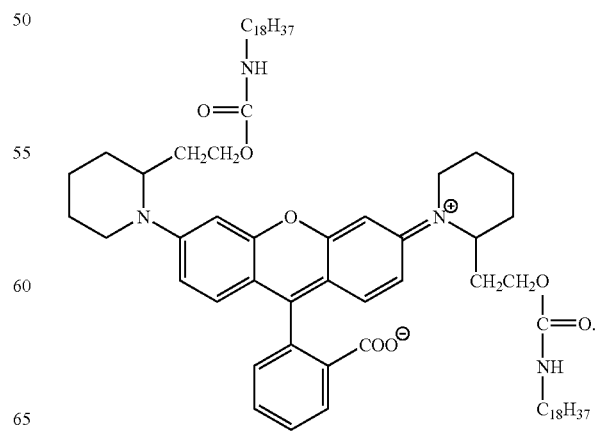

Example IXB

The process of Example IB was repeated except that N,N-dimethyl-1,4-phenylene diamine (obtained from Aldrich Chemical Co., Milwaukee, Wis.), of the formula

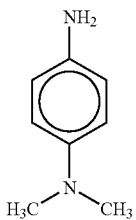

was used instead of distearyl amine. The N,N-dimethyl-1,4-phenylene diamine was present in an amount of 2.5 moles of N,N-dimethyl-1,4-phenylene diamine per every one mole of dichlorofluorescein. In addition, 2 moles of zinc chloride were used per every one mole of dichlorofluorescein and 1 mole of calcium oxide was used per every one mole of dichlorofluorescein, the solvent was N-methyl pyrrolidone instead of tetramethylene sulfone, and the reaction mixture was heated to 140° C. for 48 hours. The reaction product was then poured into water and filtered and washed with water. It is believed that the product was of the formula

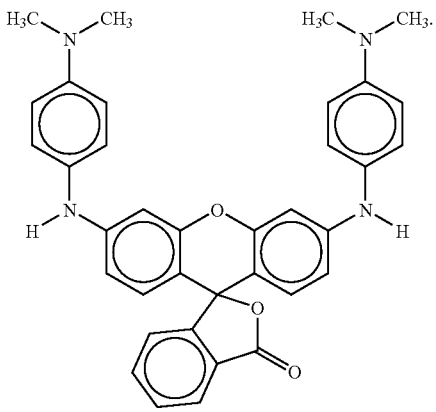

The ring-opened, or protonated, or free-base form of this chromogen is believed to be of the formula

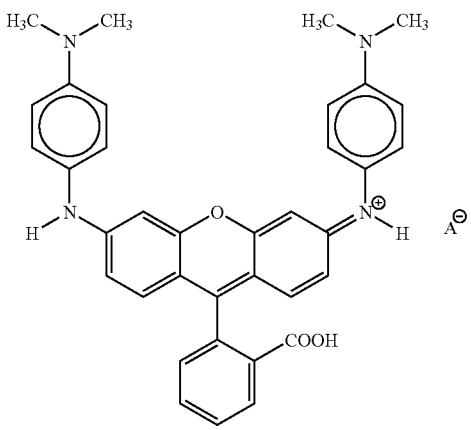

wherein A is the anion corresponding to the acid used for protonaton. The zwitterionic form of this chromogen is believed to be of the formula

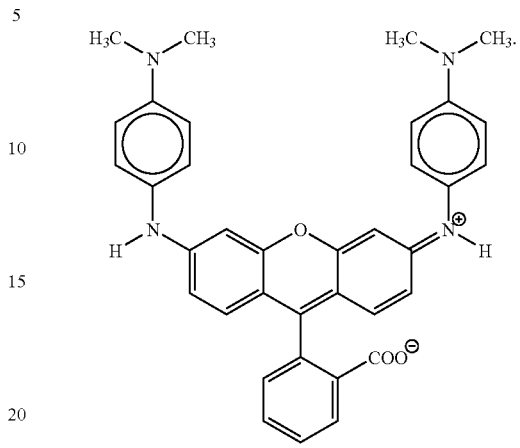

Example XB

The process of Example IB was repeated except that N,N-diethyl-1,4-phenylene diamine (obtained from Aldrich Chemical Co., Milwaukee, Wis.), of the formula

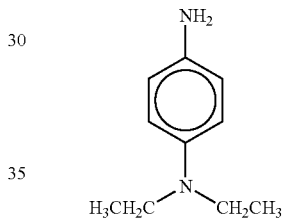

was used instead of distearyl amine. The N,N-diethyl-1,4-phenylene diamine was present in an amount of 2.5 moles of N,N-diethyl-1,4-phenylene diamine per every one mole of dichlorofluorescein. In addition, 2 moles of zinc chloride were used per every one mole of dichlorofluorescein and 1 mole of calcium oxide was used per every one mole of dichlorofluorescein, the solvent was N-methyl pyrrolidone instead of tetramethylene sulfone, and the reaction mixture was heated to 150° C. for 96 hours. The reaction product was then poured into water and filtered and washed with water. It is believed that the product was of the formula

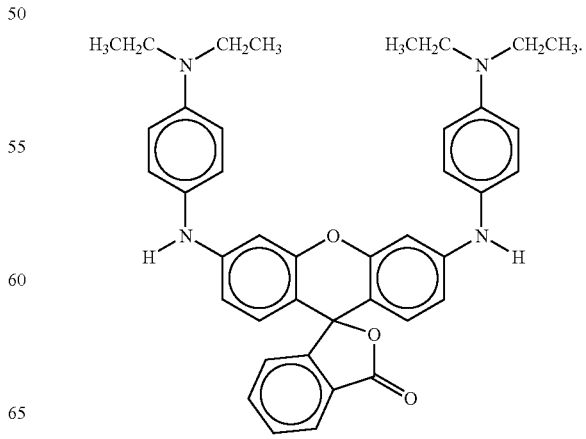

The ring-opened, or protonated, or free-base form of this chromogen is believed to be of the formula

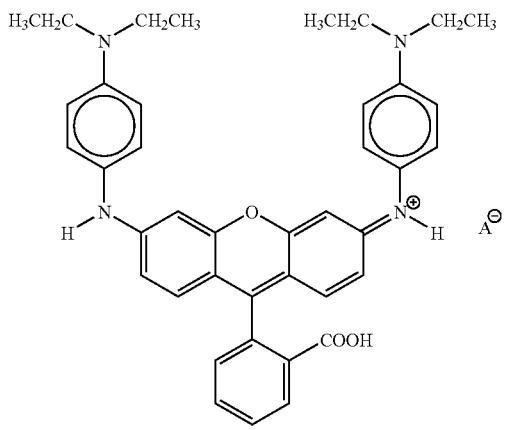

wherein A is the anion corresponding to the acid used for protonaton. The zwitterionic form of this chromogen is believed to be of the formula

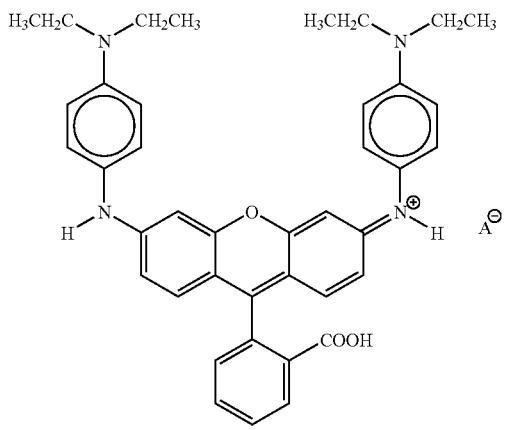

Example XIB

The process of Example IB was repeated except that N-benzylethanolamine (obtained from Aldrich Chemical Co., Milwaukee, Wis., of the formula

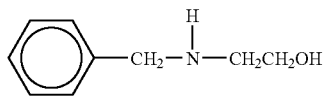

was used instead of distearyl amine. The N-benzylethanolamine was present in an amount of 2.5 moles of N-benzylethanolamine per every one mole of dichlorofluorescein. In addition, 2 moles of zinc chloride were used per every one mole of dichlorofluorescein and 1 mole of calcium oxide was used per every one mole of dichlorofluorescein, the solvent was dimethyl formamide instead of tetramethylene sulfone, and the reaction mixture was heated to 150° C. for 48 hours.

Example XIC

The process of Example IC was repeated using the product obtained in Example XIB except that the product was poured into methanol and sufficient EDTA was added to remove all of the $Zn^{2+}$ and $Ca^{2+}$ ions. It is believed that the purified product was of the formula

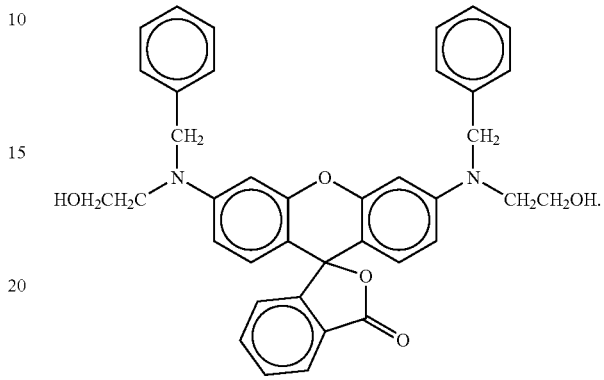

Example XIC-1

About 10 grams of the product obtained in Example XIC is added to 9.9 grams of octadecylisocyanate (available from Aldrich Chemical Co., Milwaukee, Wis.) at 120° C., after which 1 drop of dibutyltindilaurate catalyst (available from Aldrich Chemical Co.) is added and the reaction is stirred and heated until disappearance of the isocyanate peak in the IR is observed. The diurethane rhodamine is poured into aluminum tins and is believed to be of the formula

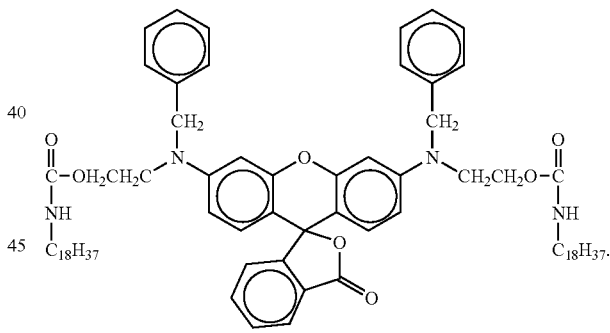

The ring-opened, or protonated, or free-base form of this chromogen is believed to be of the formula

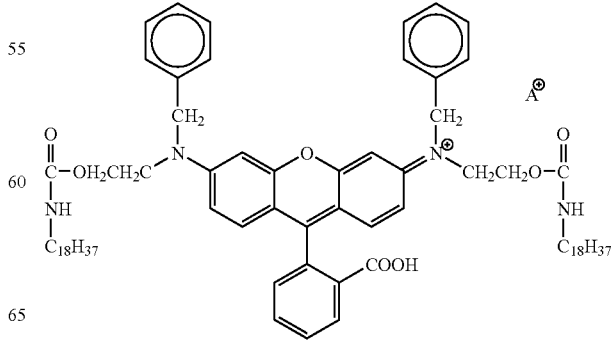

wherein A is the anion corresponding to the acid used for protonaton. The zwitterionic form of this chromogen is believed to be of the formula

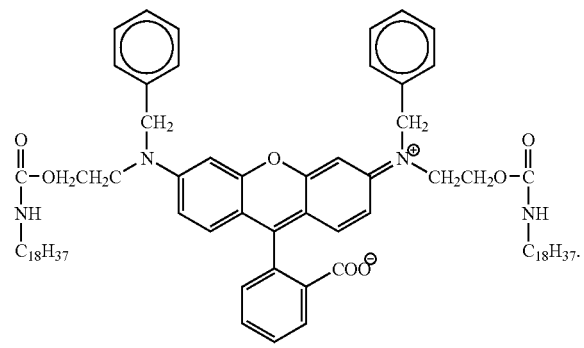

Example XIIB

The process of Example IB was repeated except that N-benzylethanolamine (obtained from Aldrich Chemical Co., Milwaukee, Wis.), of the formula

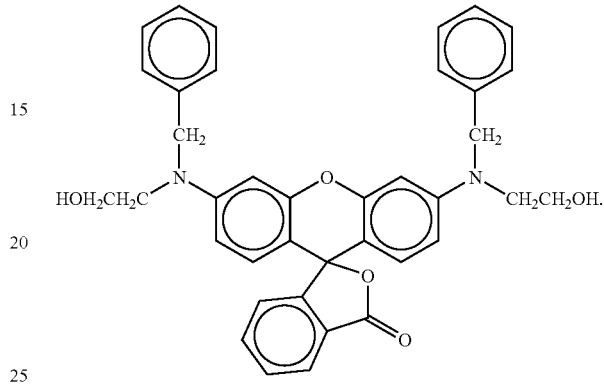

was used instead of distearyl amine. The N-benzylethanolamine was present in an amount of 10 moles of N-benzylethanolamine per every one mole of dichlorofluorescein. In addition, 2 moles of zinc chloride were used per every one mole of dichlorofluorescein and 1 mole of calcium oxide was used per every one mole of dichlorofluorescein, the solvent was the excess N-benzylethanolamine instead of tetramethylene sulfone, and the reaction mixture was refluxed in an oil bath for 48 hours, followed by distilling off the excess amine.

Example XIIC

The process of Example IC was repeated using the product obtained in Example XIIB except that the product was poured into methanol and sufficient EDTA was added to remove all of the $Zn^{2+}$ and $Ca^{2+}$ ions. It is believed that the purified product was of the formula

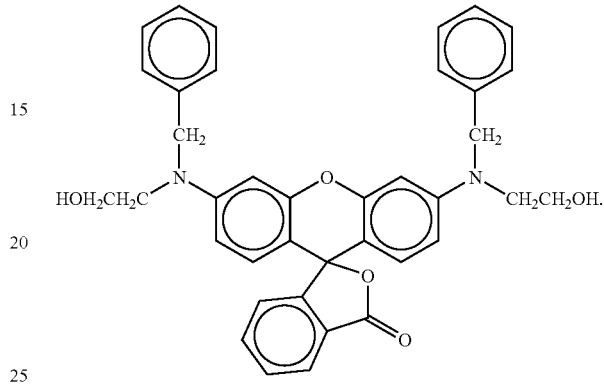

Example XIIC-1

In a glass reaction flask is combined 10 grams of the product obtained in Example XIIC, 29.8 grams of UNICID® 700 (a material containing carboxylic acid of the formula RCOOH wherein R is a linear alkyl group having an average of about 50 carbon atoms, also containing other unfunctionalized wax materials in an amount of up to about 25 percent by weight; available from Baker Petrolite, Sugarland, Tex.), 152 grams of xylene (available from Tarr, Inc., Portland, Oreg.), and 0.6 grams of para-toluenesulfonic acid (available from Capital Resin Corp., Columbus, Ohio). The materials are mixed and heated to a reflux temperature of about 143° C. After about 72 hours, the reaction is complete. The reaction mixture is then cooled to 40° C. and filtered. The filter cake is reslurried and filtered two more times in methanol to remove residual xylene. The filter cake is then dried in air at ambient temperature. It is believed that this filter cake will contain a chromogen of the formula

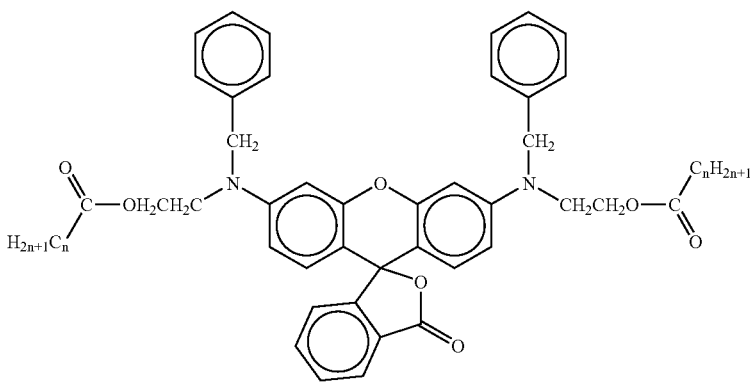

wherein n has an average value of about 50. The ring-opened, or protonated, or free-base form of this chromogen is believed to be of the formula

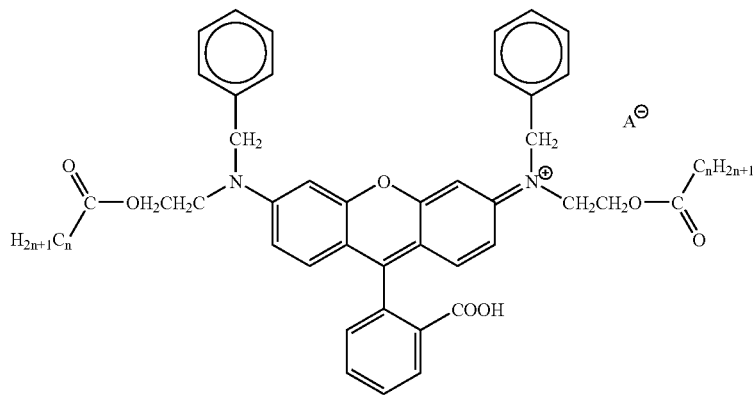

wherein A is the anion corresponding to the acid used for protonaton. The zwitterionic form of this chromogen is believed to be of the formula

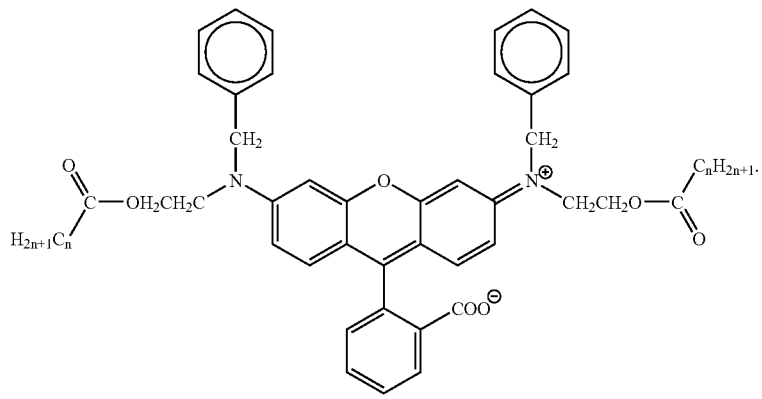

Example XIIIB

The process of Example IB was repeated except that 2-(ethylamino)ethanol (obtained from Aldrich Chemical Co., Milwaukee, Wis.), of the formula

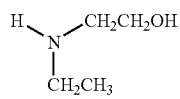

was used instead of distearyl amine. The 2-(ethylamino)ethanol was present in an amount of 20 moles of 2-(ethylamino) ethanol per every one mole of dichlorofluorescein. In addition, 2 moles of zinc chloride were used per every one mole of dichlorofluorescein and 1 mole of calcium oxide was used per every one mole of dichlorofluorescein, the solvent was the excess 2-(ethylamino)ethanol instead of tetramethylene sulfone, and the reaction mixture was refluxed in an oil bath for 24 hours, followed by distilling off the excess amine.

Example XIIIC

The process of Example IC was repeated using the product obtained in Example XIIIB except that the product was poured into methanol and sufficient EDTA was added to remove all of the $Zn^{2+}$ and $Ca^{2+}$ ions. It is believed that the purified product was of the formula

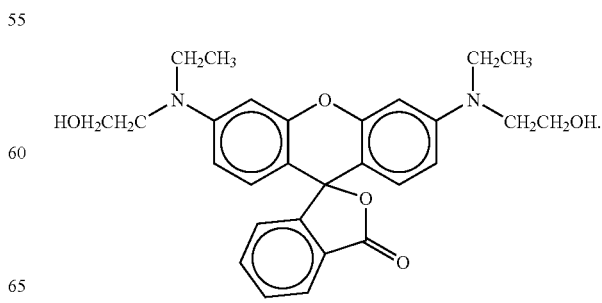

Example XIIIC-1

About 10 grams of the product obtained in Example XIIIC is added to 12.5 grams of octadecylisocyanate (available from Aldrich Chemical Co., Milwaukee, Wis.) at 120° C., after which 1 drop of dibutyltindilaurate catalyst (available from Aldrich Chemical Co.) is added and the reaction is stirred and heated until disappearance of the isocyanate peak in the IR is observed. The diurethane rhodamine is poured into aluminum tins and is believed to be of the formula

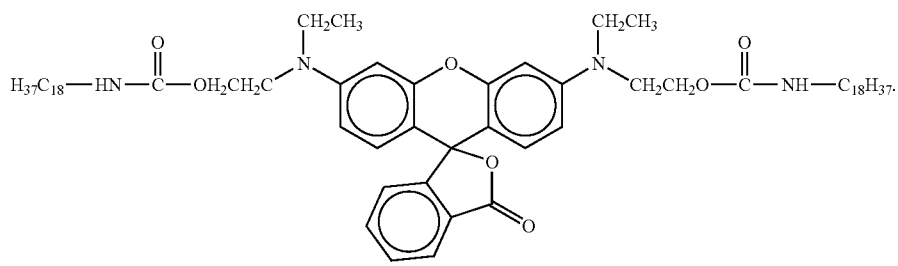

The ring-opened, or protonated, or free-base form of this chromogen is believed to be of the formula

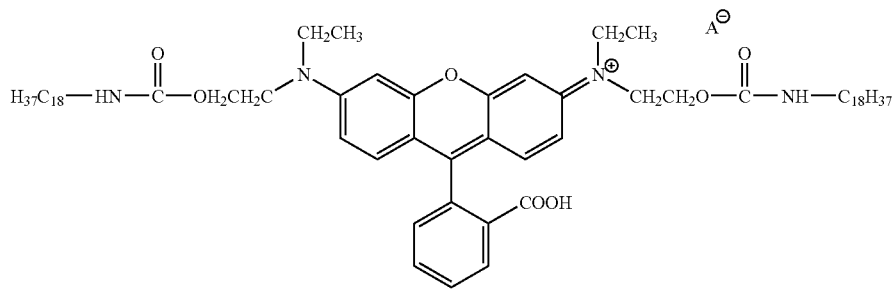

wherein A is the anion corresponding to the acid used for protonaton. The zwitterionic form of this chromogen is believed to be of the formula

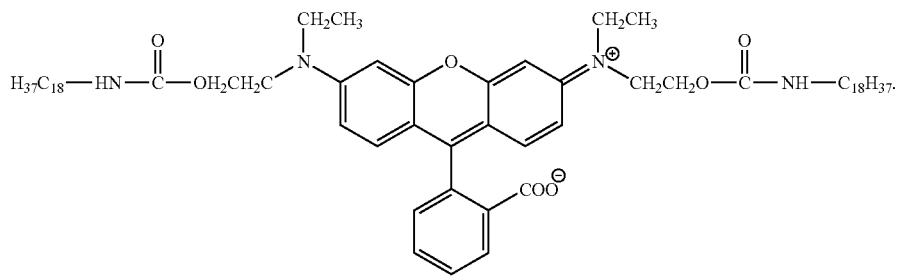

Example XIVB

The process of Example IB was repeated except that 2-aminoanthracene (obtained from Aldrich Chemical Co., Milwaukee, Wis.), of the formula

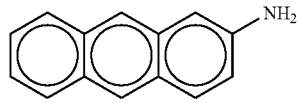

was used instead of distearyl amine. The 2-aminoanthracene was present in an amount of 2.05 moles of 2-aminoanthracene per every one mole of dichlorofluorescein. It is believed that the product was of the formula

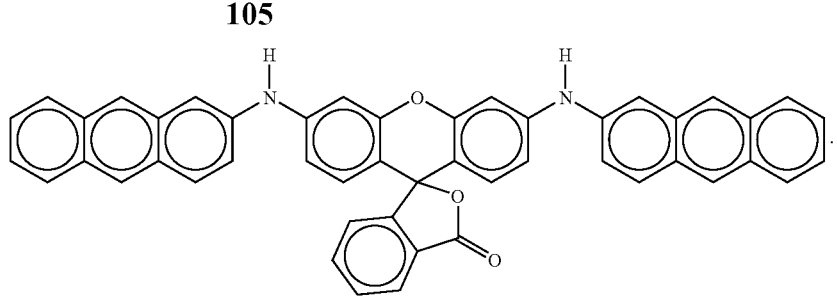

The ring-opened, or protonated, or free-base form of this chromogen is believed to be of the formula

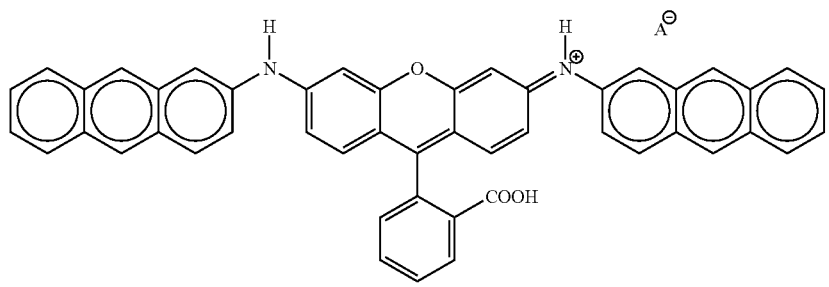

wherein A is the anion corresponding to the acid used for protonaton. The zwitterionic form of this chromogen is believed to be of the formula

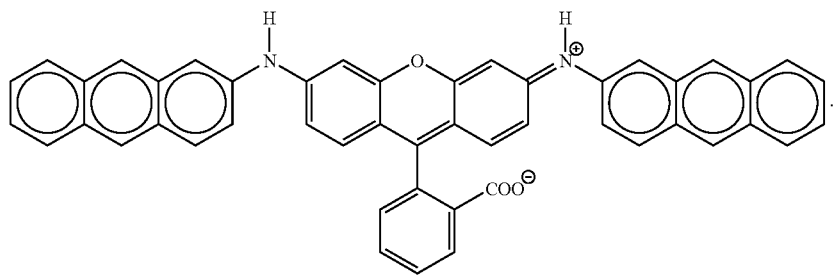

Example XVB

The process of Example IB was repeated except that a mixture of stearyl amine (ARMEEN 18D; obtained from Akzo-Nobel, McCook, Ill.) and distearyl amine was used instead of pure distearyl amine. The stearyl amine was present in an amount of 1.02 moles of stearyl amine per every one mole of dichlorofluorescein, and the distearyl amine was present in an amount of 1.02 moles of distearyl amine per every one mole of dichlorofluorescein.

Example XVC

The process of Example IC was repeated using the product obtained in Example XVB. It is believed that the purified product was a mixture of compounds of the formulae

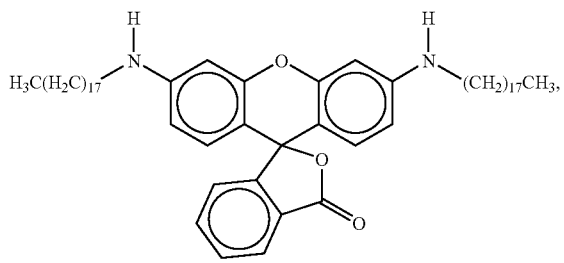

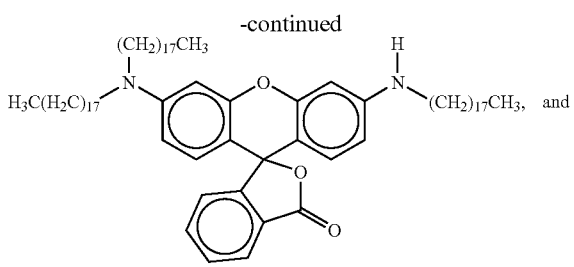

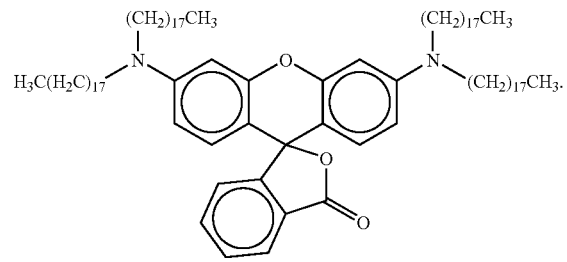

The ring-opened, or protonated, or free-base forms of these chromogens are believed to be of the formulae, respectively,

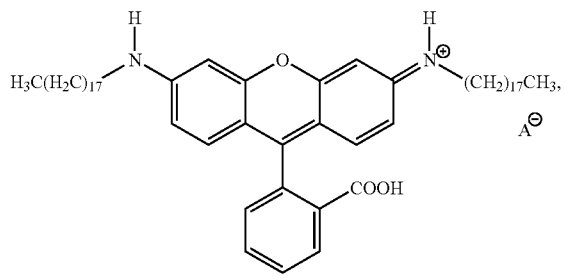

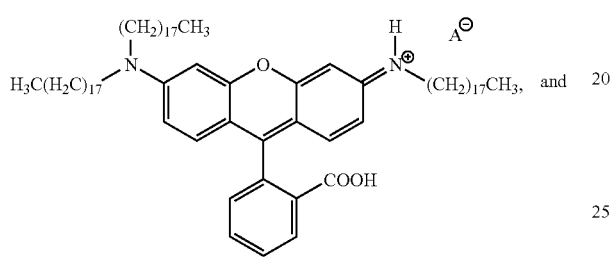

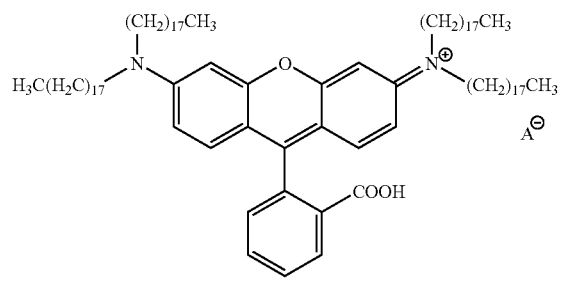

wherein A is the anion corresponding to the acid used for protonaton. The zwitterionic forms of these chromogens are believed to be of the formulae, respectively,

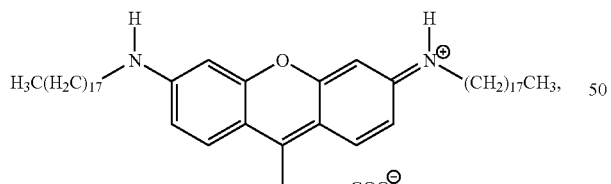

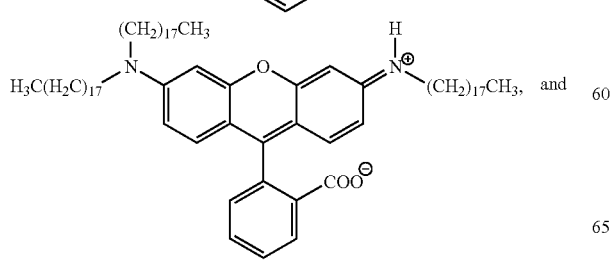

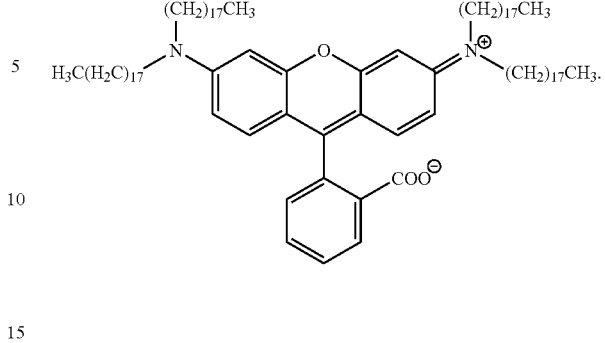

Example XVI

Preparation of Calcium Tetrastearyl Colorant

The process of Example IF is repeated except that 80.3 grams of the ring-closed purified tetrastearyl chromogen, 400 grams of toluene, and 18.18 grams of calcium distearate are employed. It is believed that the product will be a magenta/red colored wax.

Example XVII

Preparation of Bismuth Tetrastearyl Colorant

The process of Example IF is repeated except that 100.2 grams of the ring-closed purified tetrastearyl chromogen, 600 grams of toluene, and 39.53 grams of bismuth tristearate are employed. It is believed that the product will be a magenta/red colored wax.

Example XVIII

Preparation of Tin Tetrastearyl Colorant

The process of Example IF is repeated except that 100 grams of the ring-closed purified tetrastearyl chromogen, 1,000 grams of MIBK, and 25.59 grams of tin distearate in a 2 liter 3-necked roundbottom flask are employed. It is believed that the product will be a magenta/red colored wax.

Example XIX

Preparation of Iron Tetrastearyl Colorant

The process of Example IF is repeated except that 32.4 grams of the ring-closed purified tetrastearyl chromogen, 400 grams of MIBK, and 7.53 grams of iron distearate are employed. It is believed that the product will be a magenta/red colored wax.

Example XX

Preparation of Copper Tetrastearyl Colorant

The process of Example IF is repeated except that 35 grams of the ring-closed purified tetrastearyl chromogen, 400 grams of MIBK, and 8.23 grams of copper distearate are employed. It is believed that the product will be a magenta/red colored wax.

Example XXI

Preparation of Aluminum Tetrastearyl Colorant

The process of Example IF is repeated except that 32.7 grams of the ring-closed purified tetrastearyl chromogen, 400 grams of MIBK, and 10.70 grams of aluminum tristearate are employed. It is believed that the product will be a magenta/red colored wax.

Example XXII

Preparation of Nickel Tetrastearyl Colorant

The process of Example IF is repeated except that 5.5 grams of the ring-closed purified tetrastearyl chromogen, 100 grams of MIBK, and 5.14 grams of nickel II stearate are employed. It is believed that the product will be a magenta/red colored wax.

Example XXIII

Preparation of Titanium Tetrastearyl Colorant

The process of Example IF is repeated except that 24.3 grams of the ring-closed purified tetrastearyl chromogen, 250 grams of toluene, and 10.71 grams of titanium IV stearate are employed. It is believed that the product will be a magenta/red colored wax.

Example XXIV

Preparation of Chromium Tetrastearyl Colorant

The process of Example IF is repeated except that 25.2 grams of the ring-closed purified tetrastearyl chromogen, 250 grams of MIBK, and 8.48 grams of chromium III stearate are employed. It is believed that the product will be a magenta/red colored wax.

Example XXV

Preparation of Phosphotungsticmolybdic "Laked" Tetrastearyl Colorant

The process of Example I is repeated except that 34.1 grams of the ring-closed purified tetrastearyl chromogen, about 400 grams of MIBK, 18.4 grams of phosphotungstic acid, and 11.6 grams of phosphomolybdic acid were employed. It is believed that the product will be a magenta/red colored wax.

Example XXVI

The processes of Examples XVI through XXV are repeated but substituting the chromogens prepared in Examples II through XV for the chromogen prepared in Example I. It is believed that similar results will be observed.

Example XXVII

The processes of Examples XVI through XXVI are repeated but substituting acetate salts instead of stearate salts. It is believed that similar results will be observed.

Example XXVIII 12.21 grams (0.15 mole) of zinc oxide (99+% pure; obtained from Aldrich Chemical Co.) and 117.81 grams (0.315 mole) of ISOCARB 24 (long chain fatty acid or Guerbet acid; believed to contain at least some isomers of the formula

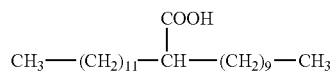

obtained from CONDEA Chemie Gmbh) into a 500 milliliter round bottom flask, and a magnetic stirring bar was then added into the flask. The mixture was heated to melt in an oil bath of 140 to 150° C. and then stirred overnight with a slow purge of nitrogen. The mixture inside became a homogeneous light yellow liquid and was poured into an aluminum pan to solidify into a white solid. It is believed that the product contained at least some isomers of the formula

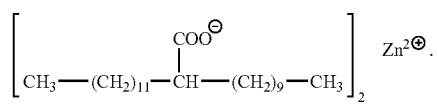

Example XXIX

The processes of Examples XVI through XXVI are repeated but using the fatty acid salts of Example XXVIII instead of stearate salts. It is believed that similar results will be observed.

Example XXX

The processes of Examples XVI through XXVI are repeated but using 2-ethylhexanoate salts instead of stearate salts. It is believed that similar results will be observed.

Example XXXI

The processes of Examples XVI through XXVI are repeated but using salts of long chain fatty carboxylic acids (C22 carboxylic acids, commercially available as UNICID 350 from Baker Petrolite, Tulsa, Okla.) instead of stearate salts. It is believed that similar results will be observed.

Example XXXII

The processes of Examples XVI through XXVI are repeated but using salts of long chain fatty carboxylic acids (C28 carboxylic acids, commercially available as UNICID 425 from Baker Petrolite, Tulsa, Okla.) instead of stearate salts. It is believed that similar results will be observed.

Ink Preparation and Testing

Preparation of Secondary Colorant

Part 1

A secondary magenta colorant was prepared as follows. In a glass reaction flask were combined 73 grams of sublimed quinizarin (obtained from Aceto Corp., Lake Success, N.Y.), 49 grams of leucoquinizarin (obtained from Aceto Corp.), 66 grams of 4-aminobenzene ethanol (obtained from Aceto Corp.), 31 grams of boric acid (obtained from Aldrich Chemical Co., Milwaukee, Wis.), and 780 grams of methanol (obtained from JT Baker, Phillipsburg, N.J.). The materials were mixed and heated until the solvent refluxed at about 66° C. After about 16 hours of reflux the reaction was complete, having generated an alcohol-substituted colorant of the formula

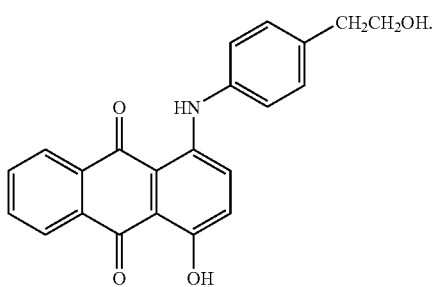

The reaction mixture was cooled and filtered. The product filter cake was dried in air at ambient temperature. The spectral strength of the alcohol-substituted colorant was determined using a spectrophotographic procedure based on the measurement of the colorant in solution by dissolving the colorant in toluene and measuring the absorbance using a Perkin Elmer Lambda 2S UV/VIS spectrophotometer. The spectral strength of the alcohol-substituted colorant was measured as about 21,000 mL Absorbance Units per gram at absorption $\lambda_{max}$, indicating a purity of about 80 percent.

Part 2

In a glass reaction flask were combined 8 grams of the alcohol-substituted colorant prepared in Part 1 of this Example, 68 grams of glacial acetic acid (obtained from J T Baker), 13 grams of propionic acid (obtained from Aldrich Chemical Co.), and 2.3 grams of acetic anhydride (obtained from Aldrich Chemical Co.). The materials were mixed and heated to a reflux temperature of about 121° C. After about 4 hours of reflux, the reaction was complete and the reaction mixture contained an ethyl acetate-substituted colorant of the formula

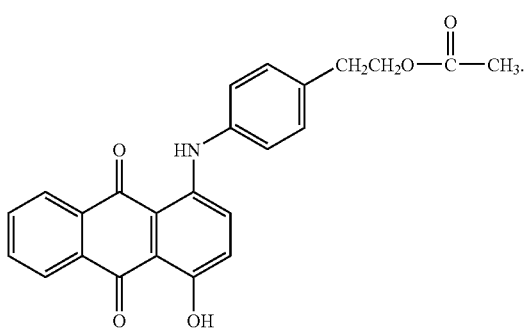

Part 3

About 91 grams of the reaction mixture containing the ethyl acetate-substituted colorant from Part 2 of this Example was charged into a glass reaction flask. The mixture was cooled to a minimum of 30° C. While mixing, about 9 grams of bromine (obtained from Aldrich Chemical Co.) was added to the mixture at a rate such that the temperature remained below about 40° C. The mixture was then heated to about 40° C. After about 24 hours of mixing the reaction was complete. The reaction mixture was then quenched into 234 grams of deionized water and allowed to cool to room temperature. The reaction mixture was then filtered. The filter cake was reslurried and filtered twice in deionized water to remove most of the residual acetic acid. The filter cake was then dried in a 60° C. oven. This filter cake contained a mixture of brominated ethyl acetate-substituted colorants of the formulae

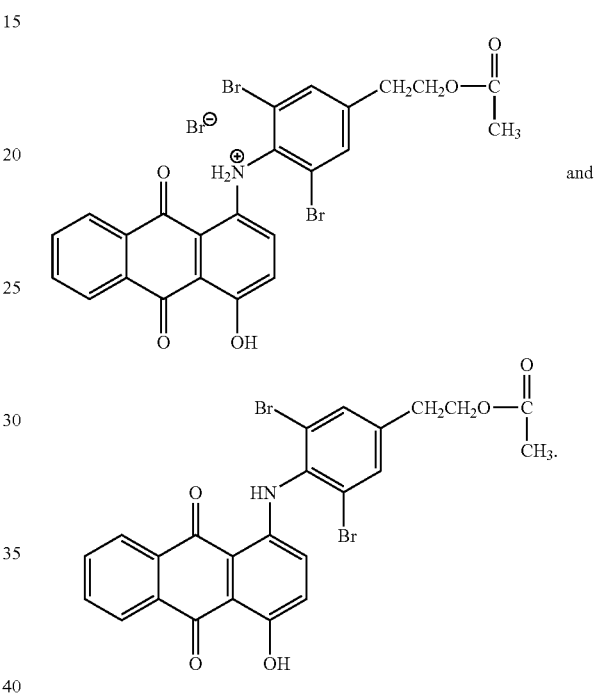

The spectral strength of the brominated ethyl acetate-substituted colorant was determined using a spectrophotographic procedure based on the measurement of the colorant in solution by dissolving the colorant in toluene and measuring the absorbance using a Perkin Elmer Lambda 2S UV/VIS spectrophotometer. The spectral strength of the brominated ethyl acetate-substituted colorant was measured as about 15,000 mL Absorbance Units per gram at absorption $\lambda_{max}$. This spectral strength indicated a purity of about 60 percent.

Part 4

In a glass reaction flask were combined 18 grams of the mixture of the brominated ethyl acetate-substituted colorant and its salt prepared in Part 3 of this Example, 72 grams of N-methyl-2-pyrrolidone (obtained from Aldrich Chemical Co.), 4 grams of sodium hydroxide (obtained from Aldrich Chemical Co.), and 4 grams of deionized water. The materials were mixed and heated to about 60° C. After about 3 hours the reaction was complete. The reaction mixture was then quenched into 234 grams of deionized water and allowed to cool to room temperature. Glacial acetic acid was added until the solution reached a pH of between 6 and 7. The reaction mixture was then filtered. The filter cake was reslurried and filtered twice in deionized water to remove most of the residual N-methyl-2-pyrrolidone. The filter cake was then dried in a 60° C. oven. This filter cake contained a brominated alcohol-substituted colorant of the formula

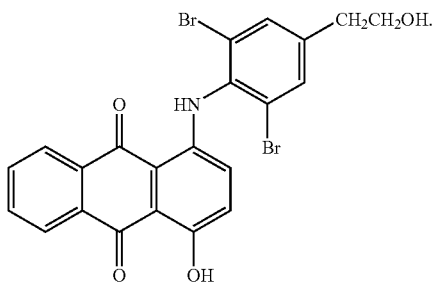

The spectral strength of the brominated alcohol-substituted colorant was determined using a spectrophotographic procedure based on the measurement of the colorant in solution by dissolving the colorant in an equal mixture of toluene and tetrahydrofuran and measuring the absorbance using a Perkin Elmer Lambda 2S UV/VIS spectrophotometer. The spectral strength of the brominated alcohol-substituted colorant was measured as about 16,000 mL Absorbance Units per gram at absorption $\lambda_{max}$. This spectral strength indicated a purity of about 60 percent.

Part 5

In a glass reaction flask were combined 16 grams of the brominated alcohol-substituted colorant prepared in Part 4 of this Example, 31 grams of UNICID® 700 (a material containing carboxylic acid of the formula $R_2COOH$ wherein $R_2$ is a linear alkyl group having an average of about 50 carbon atoms, also containing other unfunctionalized wax materials in an amount of up to about 25 percent by weight; obtained from Baker Petrolite, Sugarland, Tex.), 152 grams of xylene (obtained from Tarr, Inc., Portland, Oreg.), and 0.6 grams of para-toluenesulfonic acid (obtained from Capital Resin Corp., Columbus, Ohio). The materials were mixed and heated to a reflux temperature of about 143° C. After about 7 hours, the reaction was complete. The reaction mixture was then cooled to 40° C. and filtered. The filter cake was reslurried and filtered two more times in methanol to remove residual xylene. The filter cake was then dried in air at ambient temperature. This filter cake contained a colorant of the formula

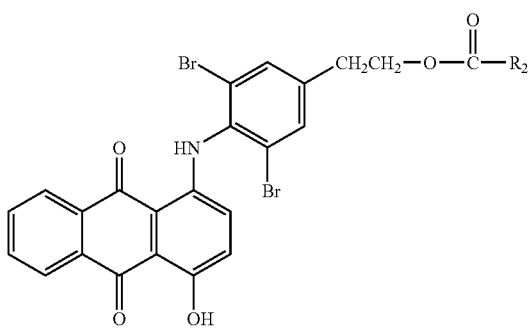

wherein $R_2$ is a linear alkyl group having an average of about 50 carbon atoms. The spectral strength of the colorant was determined using a spectrophotographic procedure based on the measurement of the colorant in solution by dissolving the colorant in an equal mixture of toluene and tetrahydrofuran and measuring the absorbance using a Perkin Elmer Lambda 2S UV/VIS spectrophotometer. The spectral strength of the colorant was measured as about 5,000 mL Absorbance Units per gram at absorption $\lambda_{max}$. This spectral strength indicated a purity of about 40 percent.

Ink Example 1

Ink compositions are prepared as follows. In a stainless steel beaker are combined 430 grams of polyethylene wax (PE 655, available from Baker Petrolite, Tulsa, Okla., of the formula $CH_3(CH_2)_{50}CH_3$), 194 grams of stearyl stearamide wax (KEMAMIDE® S-180, available from Crompton Corporation, Greenwich, Conn.), 219 grams of a tetra-amide resin obtained from the reaction of one equivalent of a C-36 dimer acid available from Uniqema, New Castle, Del. with two equivalents of ethylene diamine and UNICID® 700 (available from Baker Petrolite, Tulsa, Okla., a long chain hydrocarbon having a terminal carboxylic acid group), prepared as described in Example 1 of U.S. Pat. No. 6,174,937, the disclosure of which is totally incorporated herein by reference, 77 grams of a urethane resin obtained from the reaction of two equivalents of ABITOL® E hydroabietyl alcohol (available from Hercules Inc., Wilmington, Del.) and one equivalent of isophorone diisocyanate, prepared as described in Example 1 of U.S. Pat. No. 5,782,966, the disclosure of which is totally incorporated herein by reference, 46 grams of a urethane resin that is the adduct of three equivalents of stearyl isocyanate and a glycerol-based alcohol, prepared as described in Example 4 of U.S. Pat. No. 6,309,453, the disclosure of which is totally incorporated herein by reference, and 2.0 gram of NAUGUARD® 445 antioxidant (available from Uniroyal Chemical Co., Middlebury, Conn.). The materials are melted together at a temperature of about 140° C. in an oven, then blended by stirring in a temperature controlled mantle at about 135° C. for about 0.5 hour. To this mixture is then added about 20 grams of the colorants prepared as described in Examples I through XXXII. In addition, about 18 grams of the secondary colorant prepared as described in Parts 1 through 5 is added. After stirring for about 3 additional hours, the magenta inks thus formed are filtered through a heated MOTT® apparatus (available from Mott Metallurgical) using #3 Whatman filter paper and a pressure of about 15 pounds per square inch. The filtered phase change inks are poured into molds and allowed to solidify to form ink sticks.

Ink Example 2

Part A: Ink Preparation

Ink compositions were prepared containing polyethylene wax (PE 655, obtained from Baker Petrolite, Tulsa, Okla., of the formula $CH_3(CH_2)_{50}CH_3$, referred to in the table as PE), a tetra-amide resin obtained from the reaction of one equivalent of a C-36 dimer acid obtained from Uniqema, New Castle, Del. with two equivalents of ethylene diamine and UNICID® 700 (obtained from Baker Petrolite, Tulsa, Okla., a long chain hydrocarbon having a terminal carboxylic acid group), prepared as described in Example 1 of U.S. Pat. No. 6,174,937, the disclosure of which is totally incorporated herein by reference, referred to in the table as TA, stearyl stearamide wax (KEMAMIDE® S-180, obtained from Crompton Corporation, Greenwich, Conn.), referred to in the table as MA, a urethane resin obtained from the reaction of two equivalents of ABITOL® E hydroabietyl alcohol (obtained from Hercules Inc., Wilmington, Del.) and one equivalent of isophorone diisocyanate, prepared as described in Example 1 of U.S. Pat. No. 5,782,966, the disclosure of which is totally incorporated herein by reference, referred to in the table as U1, a urethane resin that was the adduct of three equivalents of stearyl isocyanate and a glycerol-based alcohol, prepared as described in Example 4 of U.S. Pat. No. 6,309,453, the disclosure of which is totally incorporated herein by reference, referred to in the table as U2, NAUGUARD® 445 antioxidant (obtained from Uniroyal Chemical Co., Middlebury, Conn.), referred to in the table as AO, the secondary colorant prepared as described in Parts 1 through 5, referred to in the table as 2° C., and various colorants and metal salts, all in the amounts (percent by weight) in the table indicated below. Inks 1, 6, 7, 8, and 9 contained a metal-free chromogen (referred to in the table as D-MF) prepared and purified as described in Example ID. Inks 2 and 5 contained a zinc tetrastearyl colorant (referred to in the table as D-Z1) prepared as described in Example IF, said colorant being prepared from a chromogen prepared and purified as described in Example ID. Inks 3 and 4 contained a zinc tetrastearyl colorant (referred to in the table as D-Z2) prepared as described in Example IF, said colorant being prepared from a chromogen prepared and purified as described in Examples IG and IH. Inks 1, 2, and 3 contained a zinc stearate salt (referred to in the table as Zn-St). Ink 4 contained a zinc 2-ethylhexanoate salt (ZN HEX-CEM, obtained from OMG Americas, Inc., Cleveland, Ohio, referred to in the table as Zn-eh). Ink 5 contained a zinc salt as prepared in Example XXVII (referred to in the table as Zn-i-24). Ink 6 contained a zinc trifluoroacetate hydrate salt ($(CF_3COO)_2Zn.xH_2O$, obtained from Aldrich Chemical Co., referred to in the table as Zn-tfa). Ink 7 contained a zinc p-toluenesulfonate hydrate salt ($(CH_3C_6H_4SO_3)_2Zn.xH_2O$, obtained from Aldrich Chemical Co., referred to in the table as Zn-pts). Ink 8 contained a zinc diethyldithiocarbamate salt ($((C_2H_5)_2NCS_2)_2Zn$, obtained from Aldrich Chemical Co., referred to in the table as Zn-ddc). All of the ink ingredients were melted and blended with mechanical stirring in steel beakers for 2 to 3 hours at 135° C. The mixtures were then filtered in Mott filters with Whatman #3 paper in an oven at 135° C. and allowed to solidify to form ink sticks.

| | ink | | | | | | | |
|---|---|---|---|---|---|---|---|---|
| | 1 | 2 | 3 | 4 | 5 | 6 | 7 | 8 |
| PE | 44.44 | 44.79 | 44.29 | 46.54 | 44.86 | 42.10 | 41.79 | 41.90 |
| TA | 16.52 | 15.92 | 16.28 | 16.72 | 16.12 | 18.24 | 18.10 | 18.15 |
| MA | 12.60 | 13.07 | 12.62 | 12.98 | 12.52 | 11.30 | 11.22 | 11.25 |
| U1 | 9.26 | 8.87 | 9.07 | 9.18 | 8.85 | 14.82 | 14.71 | 14.75 |
| U2 | 7.28 | 7.07 | 7.23 | 7.06 | 6.81 | 6.21 | 6.17 | 6.18 |
| AO | 0.19 | 0.18 | 0.19 | 0.18 | 0.18 | 0.19 | 0.19 | 0.19 |
| 2° C. | 1.77 | 1.85 | 1.89 | 1.90 | 1.90 | 1.86 | 1.85 | 1.85 |
| D-MF | 3.27 | — | — | — | — | 3.37 | 3.34 | 3.35 |
| D-Z1 | — | 3.40 | — | — | 3.50 | — | — | — |
| D-Z2 | — | — | 3.47 | 3.50 | — | — | — | — |
| Zn-St | 4.67 | 4.85 | 4.96 | — | — | — | — | — |
| Zn-eh | — | — | — | 1.94 | — | — | — | — |
| Zn-i-24 | — | — | — | — | 5.26 | — | — | — |
| Zn-tfa | — | — | — | — | — | 1.91 | — | — |
| Zn-pts | — | — | — | — | — | — | 2.63 | — |
| Zn-ddc | — | — | — | — | — | — | — | 2.38 |

For comparative purposes, comparative inks were prepared by a similar process except that the inks did not contain an organic metal salt. The comparative inks contained the ingredients listed in the amounts indicated in the table below. Comparative Ink D contained commercially available Solvent Red 49 (SR49; a rhodamine colorant obtained from BASF, Germany) and dodecyl benzene sulfuric acid (DDBSA, Bio-soft S-100, obtained from Stepan Company, Elwood, Ill.).

| | ink | | | |
|---|---|---|---|---|
| | A | B | C | D |
| PE | 47.00 | 47.00 | 47.50 | 45.67 |
| TA | 16.89 | 16.89 | 17.07 | 19.04 |
| MA | 13.11 | 13.11 | 13.26 | 13.17 |
| U1 | 9.28 | 9.28 | 9.37 | 10.68 |
| U2 | 7.13 | 7.13 | 7.21 | 8.09 |
| AO | 0.19 | 0.19 | 0.19 | 0.20 |
| 2° C. | 1.90 | 1.90 | 1.90 | 1.91 |
| D-MF | 4.50 | — | — | — |
| D-Z1 | — | 4.50 | — | — |
| D-Z2 | — | — | 3.57 | — |
| SR49 | — | — | — | 0.46 |
| DDBSA | — | — | — | 0.80 |

Part B: Print Testing

The inks prepared in Part A were used to generate prints on HAMMERMILL LASERPRINT® paper using a K Printing Proofer (manufactured by RK Print Coat Instrument Ltd., Litlington, Royston, Heris, SG8 0OZ, U.K.). In this method, the tested inks were melted onto a printing plate set at 150° C. temperature. A roller bar fitted with the paper was then rolled over the plate containing the melted ink on its surface. The ink on the paper was cooled, resulting in three separated images of rectangular blocks. The most intensely colored block contained the most ink deposited on the paper, and was therefore used to obtain the color value measurements. Printed samples of the magenta inks from the K-Proofer were evaluated for color characteristics, which are reported in the tables below. The table below lists the viscosity ($\eta$, centipoise) of the inks at 140° C., the spectral strength in n-butanol (SS, $mL*g^{-1} cm^{-1}$) and absorbance maximum (Lambda max, $\lambda_{max}$, nm) of the inks, the glass transition point ($T_g$, ° C.), the melting points (mp, ° C., as measured by DSC), and the CIE L*a*b color coordinates of the prints. Color space data were obtained on an ACS® Spectro Sensor® II Colorimeter (obtained from Applied Color Systems Inc.) in accordance with the measuring methods stipulated in ASTM 1E805 (Standard Practice of Instrumental Methods of Color or Color Difference Measurements of Materials) using the appropriate calibration standards supplied by the instrument manufacturer. For purposes of verifying and quantifying the overall colorimetric performance of the inks, measurement data were reduced, via tristimulus integration, following ASTM E308 (Standard Method for Computing the Colors of Objects using the CIE System) in order to calculate the 1976 CIE L* (Lightness), a* (redness-greenness), and b* (yellowness-blueness) CIELAB values for each phase change ink sample.

| | ink | | | | | | | |
|---|---|---|---|---|---|---|---|---|
| | 1 | 2 | 3 | 4 | 5 | 6 | 7 | 8 |
| $\eta$ | 10.58 | 10.89 | 10.81 | — | — | — | — | — |
| SS | 998 | 887 | 1050 | — | — | — | — | — |
| $\lambda_{max}$ | 545 | 546 | 546 | — | — | — | — | — |
| $T_g$ | 14.29 | 16.48 | 14.27 | — | — | — | — | — |
| mp | 83, 103 | 84, 103 | 84, 104 | — | — | — | — | — |
| L* | 56.48 | 54.97 | 54.56 | 55.53 | 54.16 | 54.40 | 52.54 | 58.80 |
| a* | 72.12 | 71.40 | 72.90 | 71.48 | 74.66 | 72.39 | 72.85 | 65.06 |
| b* | −34.80 | −33.89 | −33.80 | −35.93 | −35.84 | −37.61 | −39.20 | −35.57 |
| C* | 80.10 | 79.00 | 80.40 | 80.00 | 82.81 | 81.57 | 82.70 | 74.15 |
| h* | 334.2 | 334.6 | 335.1 | 333.3 | 333.4 | — | — | — |

— = not measured or calculated

| | ink | | | |
|---|---|---|---|---|
| | A | B | C | D |
| $\eta$ | 10.15 | 10.35 | — | 10.77 |
| SS | 1497 | 1239 | — | 1279 |
| $\lambda_{max}$ | 545 | 545 | — | 555 |
| $T_g$ | — | — | — | 21.19 |
| mp | — | — | — | 83, 104 |
| L* | 57.31 | 68.66 | 61.22 | 60.90 |
| a* | 69.12 | 53.17 | 65.54 | 68.03 |
| b* | −35.52 | −26.33 | −31.30 | −42.73 |
| C* | 77.62 | 59.34 | 72.64 | 80.33 |
| h* | 332.9 | 333.7 | 334.5 | — |

— = not measured or calculated

As the data indicate, the inks prepared with the additional metal organic salt exhibited, on average, a stronger chroma or color strength, as evidenced by a higher C* value, compared to the inks prepared with no additional metal organic salt.

Other embodiments and modifications may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:

1. A compound of the formula

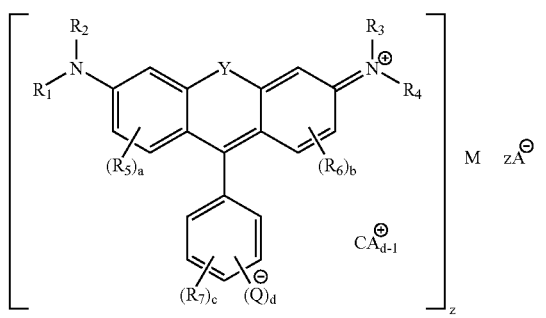

wherein M is either (1) a metal ion having a positive charge of +y wherein y is an integer which is at least 2, said metal ion being capable of forming a compound with at least two

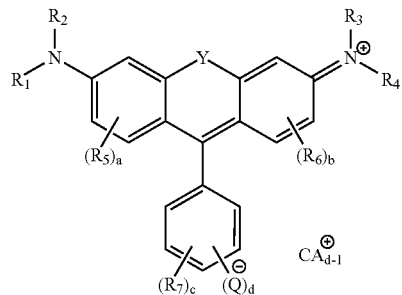

chromogen moieties, or (2) a metal-containing moiety capable of forming a compound with at least two

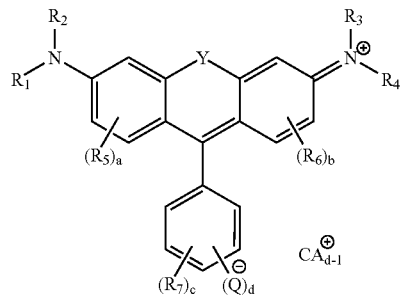

chromogen moieties, z is an integer representing the number of

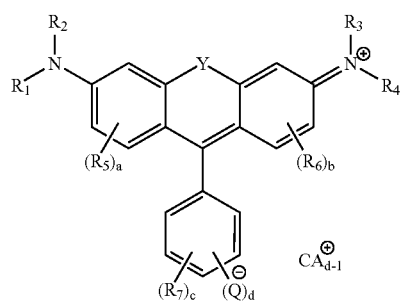

chromogen moieties associated with the metal and is at least 2, $R_1$, $R_2$, $R_3$, and $R_4$ each, independently of the others, is (i) a hydrogen atom, (ii) an alkyl group, (iii) an aryl group, (iv) an arylalkyl group, or (v) an alkylaryl group, wherein $R_1$ and $R_2$ can be joined together to form a ring, wherein $R_3$ and $R_4$ can be joined together to form a ring, and wherein $R_1$, $R_2$, $R_3$, and $R_4$ can each be joined to a phenyl ring in the central structure, provided that the number of carbon atoms in $R_1+R_2+R_3+R_4$ is at least 16 a and b each, independently of the others, is an integer which is 0, 1, 2, or 3, c is an integer which is 0, 1, 2, 3, or 4, each $R_5$, $R_6$, and $R_7$, independently of the others, is (i) an alkyl group, (ii) an aryl group, (iii) an arylalkyl group, (iv) an alkylaryl group, (v) a halogen atom, (vi) an ester group, (vii) an amide group, (viii) a sulfone group, (ix) an amine group or ammonium group, (x) a nitrile group, (xi) a nitro group, (xii) a hydroxy group, (xiii) a cyano group, (xiv) a pyridine or pyridinium group, (xv) an ether group, (xvi) an aldehyde group, (xvii) a ketone group, (xviii) a carbonyl group, (xix) a thiocarbonyl group, (xx) a sulfate group, (xxi) a sulfide group, (xxii) a sulfoxide group, (xxiii) a phosphine or phosphonium group, (xxiv) a phosphate group, (xxv) a mercapto group, (xxvi) a nitroso group, (xxvii) an acyl group, (xxviii) an acid anhydride group, (xxix) an azide group, (xxx) an azo group, (xxxi) a cyanato group, (xxxii) an isocyanato group, (xxxiii) a thiocyanato group, (xxxiv) an isothiocyanato group, (xxxv) a urethane group, or (xxxvi) a urea group, wherein $R_5$, $R_6$, and $R_7$ can each be joined to a phenyl ring in the central structure,

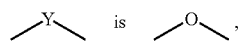

$Q^-$ is a $COO^-$ group or a $SO_3^-$ group, d is an integer which is 1, 2, 3, 4, or 5, A is an organic anion, wherein the organic anion is an oligomeric or polymeric anion, or the organic anion is a monomeric anion selected from the group consisting of stearate, propionate, butyrate, valerate, hexanoate, heptanoate, octanoate, nonanoate, decanoate, undecanoate, laurate, tridecanoate, myristate, pentadecanoate, palmitate, heptadecanoate, nonadecanoate, eicosanoate, heneicosanoate, docosanoate, tricosanoate, tetracosanoate, hexacosanoate, heptacosanoate, octacosanoate, triacontanoate, isobutyrate, ethylbutyrate, trimethylacetate, 2-methylbutyrate, isovalerate, 2,2-dimethylbutyrate, tert-butylacetate, 2-methylvalerate, 2-propylpentanoate, 3-methylvalerate, 4-methylvalerate, 2-methylhexanoate, pyruvate, 2-ketobutyrate, 3-methyl-2-oxobutanoate, 2-oxopentanoate, 3-methyl-2-oxopentanoate, 4-methyl-2-oxopentanoate, 2-oxohexanoic acid, 3-fluoropyruvate, 4-methylthio-2-oxobutyrate, acrylate, methacrylate, crotonate, vinylacetate, tiglate, 3,3-dimethylacrylate, trans-2-pentenoate, 4-pentenoate, trans-2-methyl-2-pentenoate, 2,2-dimethyl-4-pentenoate, trans-2-hexenoate, trans-3-hexenoate, 2-ethyl-2-hexenoate, 6-heptenoate, 2-octenoate, citronellate, myristoleate, palmitoleate, oleate, elaidate, 11-eicosenoate, erucate, nervonate, chloroacetate, bromoacetate, iodoacetate, difluoroacetate, dichloroacetate, dibromoacetate, chlorodifluoroacetate, trichloroacetate, tribromoacetate, 2-chloropropionate, 3-chloropropionate, 2-bromopropionate, 3-bromopropionate, 2-iodopropionate, 3-iodopropionate, 2,2-dichloropropionate, 2,3-dibromopropionate, pentafluoropropionate, 2-bromo-2-methylpropionate, 3-bromo-2-(bromomethyl)-propionate, 3-chloropivalate, 3,3-dichloropivalate, 4-chlorobutyrate, 2-bromobutyrate, 4-bromobutyrate, heptafluorobutyrate, 2-bromo-3-methylbutyrate, 5-chlorovalerate, 2-bromovalerate, 5-bromovalerate, nonafluoropentanoate, 2-bromohexanoate, 6-bromohexanoate, tridecafluoroheptanoate, 2-bromooctanoate, 8-bromooctanoate, pentadecafluorooctanoate, heptadecafluorononanoate, nonadecafluorodecanoate, 11-bromoundecanoate, 12-bromododecanoate, perfluorododecanoate, 2-bromotetradecanoate, 2-bromohexadecanoate, 3-chloroacrylate, 2-bromoacrylate, 2-(trifluoromethyl)acrylate, 2-(bromomethyl)acrylate, 4,4,4-trifluoro-3-methyl-2-butenoate, methoxyacetate, ethoxyacetate, 3-methoxypropionate, 2-(2-methoxyethoxy)acetate, 2[2-(methoxyethoxy)ethoxy]acetate, tetrahydro-2-furoate, tetrahydro-3-furoate, 2,3,4,6-di-O-isopropylidene-2-ketogluconate, 3-nitropropionate, 6-nitrocaproate, 12-nitrododecanoate, levulinate, 4-acetylbutyrate, 6-oxoheptanoate, 7-oxooctanoate, 4,6-dioxoheptanoate, 3,4-dihydro-2,2-dimethyl-4-oxo-2H-pyran-6-carboxylate, cyclopentanecarboxylate, cyclopentylacetate, 3-cyclopentylpropionate, 3-methyl-2-(nitromethyl)-5-oxocyclopentaneacetate, cyclohexanecarboxylate, cyclohexylacetate, dicyclohexylacetate, cyclohexanepropionate, cyclohexanepentanoate, 1-methyl-1-cyclohexanecarboxylate, 2-methyl-1-cyclohexanecarboxylate, 3-methyl-1-cyclohexanecarboxylate, 4-methyl-1-cyclohexanecarboxylate, 4-tert-butylcyclohexanecarboxylate, 4-pentylcyclohexanecarboxylate, 4-methylcyclohexaneacetate, 3-methoxycyclohexanecarboxylate, 4-methoxycyclohexanecarboxylate, cyclohexanecarboxylate, 2-norbornaneacetate, 4-pentylbicyclo[2.2.2]octane-1-carboxylate, 3-oxotricyclo[2.2.1.0(2,6)]-heptane-1-carboxylate, 3-noradamantanecarboxylate, 1-adamantanecarboxylate, 1-adamantaneacetate, 1-cyclopentene-1-carboxylate, 2-cyclopentene-1-acetate, 1-cyclohexene-1-carboxylate, 1-methyl-2-cyclohexene-1-carboxylate, 1,4-dihydro-2-methylbenzoate, retinoate, ketopinate, abietate, phenylacetate, 1-phenyl-1-cyclopentanecarboxylate, alpha-phenylcyclopentaneacetate, diphenylacetate, triphenylacetate, 2-phenylpropionate, hydrocinnamate, alpha-methylhydrocinnamate, alpha-(tert-butyl)hydrocinnamate, 2,2-diphenylpropionate, 3,3-diphenylpropionate, 3,3,3-triphenylpropionate, 2-phenylbutyrate, 3-phenylbutyrate, 4-phenylbutyrate, 5-phenylvalerate, 3-methyl-2-phenylvalerate, 6-phenylhexanoate, alpha-fluorophenylacetate, alpha-bromophenylacetate, alpha-methoxyphenylacetate, phenoxyacetate, alpha,beta-dibromohydrocinnamate, 3-phenoxypropionate, 2-phenoxypropionate, 11-phenoxyundecanoate, 2-phenoxybutyrate, alpha-methoxy-alpha-(trifluoromethyl)phenylacetate, (phenylthio)acetate, 3-(phenylthio)acrylate, benzylthioglycolate, 2-ethylthio-2,2-diphenylacetate, 3-benzoylpropionate, 2-methyl-4-oxo-4-phenylbutyrate, 4-benzoylbutyrate, o-tolylacetate, 3-oxo-1-indancarboxylate, 1,2,3,4-tetrahydro-2-naphthoate, (alpha,alpha,alpha-trifluoro-o-tolyl)acetate, 2-fluorophenylacetate, 2-chlorophenylacetate, 2-bromophenylacetate, 2-iodophenylacetate, 2-(2-chlorophenoxy)propionate, 2-methoxyphenylacetate, 3-(2-methoxyphenyl)propionate, 2-nitrophenylacetate, 2-formylphenoxyacetate, m-tolylacetate, 3-fluorophenylacetate, 3-chlorophenylacetate, 3-bromophenylacetate, 2-(3-chlorophenoxy)propionate, (alpha,alpha,alpha-trifluoro-m-tolyl)acetate, 3-methoxyphenylacetate, 3-nitrophenylacetate, p-tolylacetate, 3-(p-tolyl)propionate, (4-methylphenoxy)acetate, 4-isobutyl-alpha-methylphenylacetate, 4-acetylphenoxyacetic acid, 4-(4-chloro-o-tolyloxy)butyrate, 4-fluorophenylacetate, (alpha,alpha,alpha-trifluoro-p-tolyl)acetate, 3-(4-fluorobenzoyl)propionate, 3-(4-chlorobenzoyl)propionate, 4-chlorophenylacetate, bis(4-chlorophenyl)acetate, 4-bromophenylacetate, 3,3,3-tris(4-chlorophenyl)propionate, 4-(bromomethyl)phenylacetate, 1-(4-chlorophenyl)-1-cyclopentanecarboxylate, 4-methoxyphenylacetate, 4-ethoxyphenylacetate, 3-(4-methoxyphenyl)propionate, 4-(4-methoxyphenyl)propionate, 4-chlorophenoxyacetate, bis(4-chlorophenoxy)acetate, 4-(methylthio)-phenylacetate, 4-nitrophenylacetate, 2-(4-nitrophenyl)propionate, 4-(4-nitrophenyl)butyrate, 3-(4-methoxybenzoyl)propionate, 4-fluorophenoxyacetate, 2-(4-chlorophenoxy)propionate, 2-(4-chlorophenoxy)2-methylpropionate, (2,4-di-tert-pentylphenoxy)acetate, 2,6-difluorophenylacetate, 2,4-difluorophenylacetate, 2,5-difluorophenylacetate, 3,5-difluorophyenylacetate, 4-chloro-o-tolyloxyacetate, 2,3-dichlorophenoxyacetate, 2,6-dichlorophenylacetate, 2,4-dichlorophenylacetate, 2,4-dichlorophenoxyacetate, 3,4-dichlorophenylacetate, 3,4-dichlorophenoxyacetate, 3,5-bis(trifluoromethyl)phenylacetate, 4-(2,4-di-tert-pentylphenoxy)butyrate, 2-(2,4-dichlorophenoxy)propionate, 4-(2,4-dichlorophenoxy)propionate, 2,4,5-trichlorophenoxyacetate, 2-(2,4,5-trichlorophenoxy)propionate, (3,4-dimethoxyphenyl)acetate, 4-benzyloxy-3-methoxyphenylacetate, 3,4-(methylenedioxy)phenylacetate, 5-methoxy-1-indanone-3-acetate, 3-(3,4-dimethoxyphenyl)propionate, 4-(3,4-dimethoxyphenyl)butyrate, (2,5-dimethoxyphenyl)acetate, 2,4-dinitrophenylacetate, (3,5-dimethoxyphenyl)acetate, 3,4,5-trimethoxyphenylacetate, 3-(3,4,5-trimethoxyphenyl)propionate, 2,3,4,5,6-pentafluorophenylacetate, 4-biphenylacetate, 1-naphthylacetate, 2-naphthylacetate, alpha-trityl-2-naphthalenepropionate, (1-naphthoxy)acetate, (2-naphthoxy)acetate, 6-methoxy-alpha-methyl-2-naphthaleneacetate, 9-fluoreneacetate, 1-pyreneacetate, 1-pyrenebutyrate, gamma-oxo-1-pyrenebutyrate, styrylacetate, cinnamate, alpha-methylcinnamate, alpha-fluorocinnamate, alpha-phenylcinnamate, 2-methylcinnamate, 2-fluorocinnamate, 2-(trifluoromethy)cinnamate, 2-chlorocinnamate, 2-methoxycinnamate, 2-nitrocinnamate, 3-fluorocinnamate, 3-(trifluoromethyl)cinnamate, 3-chlorocinnamate, 3-bromocinnamate, 3-methoxycinnamate, 3-nitrocinnamate, 4-methylcinnamate, 4-fluorocinnamate, 4-(trifluoromethyl)cinnamate, 4-chlorocinnamate, 4-bromocinnamate, 4-methoxycinnamate, 4-nitrocinnamate, 4-formylcinnamate, 2,6-difluorocinnamate, 2,4-difluorocinnamate, 2,5-difluorocinnamate, 3,4-difluorocinnamate, 3,5-difluorocinnamate, 2-chloro-6-fluorocinnamate, 2,4-dichlorocinnamate, 3,4-dichlorocinnamate, 5-bromo-2-methoxycinnamate, 2,3-dimethoxycinnamate, 2,4-dimethoxycinnamate, 2,5-dimethoxycinnamate, 3,4-dimethoxycinnamate, 3,4-(methylenedioxy)cinnamate, 3,5-dimethoxycinnamate, 2-chloro-5-nitrocinnamate, 4-chloro-3-nitrocinnamate, 2,3,4-trifluorocinnamate, 3,4,5-trimethoxycinnamate, 2,4,5-trimethoxycinnamate, alpha-methyl-2,4,5-trimethoxycinnamate, 4,5-dimethoxy-2-nitrocinnamate, 2,3,4,5,6-pentafluorocinnamate, 3-methylindene-2-carboxylate, 3-(4-methylbenzoyl)acrylate, 3-(2,5-dimethylbenzoyl)acrylate, 3-(2,3,5,6-tetramethylbenzoyl)acrylate, 3-(4-methoxybenzoyl)acrylate, 3-(4-ethoxybenzoyl)acrylate, 6-methylchromone-2-carboxylate, benzoate, o-toluate, 2-fluorobenzoate, alpha,alpha,alpha-trifluoro-o-toluate, 2-chlorobenzoate, 2-bromobenzoate, 2-iodobenzoate, o-anisate, 2-ethoxybenzoate, 2-nitrobenzoate, 2-acetylbenzoate, 2-(p-toluoyl)benzoate, m-toluate, 3-fluorobenzoate, alpha,alpha,alpha-trifluoro-m-toluate, 3-chlorobenzoate, 3-(chloromethyl)benzoate, 3-bromobenzoate, 3-iodobenzoate, m-anisate, 3-nitrobenzoate, p-toluate, 4-ethylbenzoate, 4-n-propylbenzoate, 4-isopropylbenzoate, 4-n-butylbenzoate, 4-tert-butylbenzoate, 4-pentylbenzoate, 4-hexylbenzoate, 4-heptylbenzoate, 4-octylbenzoate, 4-vinylbenzoate, 4-fluorobenzoate, alpha,alpha,alpha-trifluoro-o-toluate, 4-chlorobenzoate, 4-bromobenzoate, 4-iodobenzoate, 4-(chloromethyl)benzoate, alpha-bromo-p-toluate, p-anisate, 4-(trifluoromethoxy)benzoate, 4-ethoxybenzoate, 4-n-propoxybenzoate, 4-butoxybenzoate, 4-pentyloxybenzoate, 4-hexyloxybenzoate, 4-heptyloxybenzoate, 4-octyloxybenzoate, 4-nonyloxybenzoate, 4-decyloxybenzoate, 4-nonyloxybenzoate, 4-dodecyloxybenzoate, 4-isopropoxybenzoate, 4-(2-cyclohexenyloxy)benzoate, 4-(methylthio)benzoate, 4-(ethylthio)benzoate, 4-nitrobenzoate, 4-acetylbenzoate, 2,3-dimethylbenzoate, 2,6-dimethylbenzoate, 3-fluoro-2-methylbenzoate, 2,3-difluorobenzoate, 2,6-difluorobenzoate, 2-fluoro-6-(trifluoromethyl)benzoate, 2-fluoro-3-(trifluoromethyl)benzoate, 2,6-bis(trifluoromethyl)benzoate, 2-chloro-6-fluorobenzoate, 2-chloro-6-fluorophenylacetate, 2,3-dichlorobenzoate, 2,6-dichlorobenzoate, 2,3-dimethoxybenzoate, 2,6-dimethoxybenzoate, 2-methyl-6-nitrobenzoate, 3-methyl-2-nitrobenzoate, 2-methyl-3-nitrobenzoate, 3-chloro-2-nitrobenzoate, 2-chloro-3-nitrobenzoate, 2-bromo-3-nitrobenzoate, 3-methoxy-2-nitrobenzoate, 3,4-dimethylbenzoate, 2,4-dimethylbenzoate, 2,5-dimethylbenzoate, 5-fluoro-2-methylbenzoate, 3-fluoro-4-methylbenzoate, 2-fluoro-5-methylbenzoate, 3-bromo-4-methylbenzoate, 2,4-bis(trifluoromethyl)benzoate, 3-iodo-4-methylbenzoate, 2-chloro-5-(trifluoromethyl)benzoate, 2,5-bis(trifluoromethyl)benzoate, 2,4-difluorobenzoate, 3,4-difluorobenzoate, 4-fluoro-2-(trifluoromethyl)benzoate, 2-fluoro-4-(trifluoromethyl)benzoate, 2-chloro-4-fluorobenzoate, 3-chloro-4-fluorobenzoate, 2,4-dichlorobenzoate, 3,4-dichlorobenzoate, 2,5-difluorobenzoate, 2,5-dichlorobenzoate, 3-bromo-4-fluorobenzoate, 5-bromo-2-chlorobenzoate, 3-methoxy-4-methylbenzoate, 3-fluoro-4-methoxybenzoate, 4-chloro-o-anisate, 5-chloro-o-anisate, 2-bromo-5-methoxybenzoate, 2,4-dimethoxybenzoate, 2,5-dimethoxybenzoate, 3,4-dimethoxybenzoate, 3,4-diethoxybenzoate, piperonylate, 2-chloro-5-(methylthio)benzoate, 2-methoxy-4-(methylthio)benzoate, 5-methyl-2-nitrobenzoate, 4-methyl-3-nitrobenzoate, 3-methyl-4-nitrobenzoate, 2-nitro-alpha,alpha,alpha-trifluoro-p-toluate, 2-fluoro-5-nitrobenzoate, 4-chloro-2-nitrobenzoate, 2-chloro-4-nitrobenzoate, 4-fluoro-3-nitrobenzoate, 4-chloro-3-nitrobenzoate, 5-chloro-2-nitrobenzoate, 2-chloro-5-nitrobenzoate, 2-bromo-5-nitrobenzoate, 4-(bromomethyl)-3-nitrobenzoate, 2-methoxy-4-nitrobenzoate, 4-methoxy-3-nitrobenzoate, 3-methoxy-4-nitrobenzoate, 5-methoxy-2-nitrobenzoate, 2,4-dinitrobenzoate, 3,5-dimethylbenzoate, 3,5-di-tert-butylbenzoate, 3,5-difluorobenzoate, 3,5-bis(trifluoromethyl)benzoate, 3,5-dichlorobenzoate, 3,5-dibromobenzoate, 3-bromo-5-iodobenzoate, 3,5-dimethoxybenzoate, 3,5-dinitrobenzoate, 2,3,4-trifluorobenzoate, 2,3,6-trifluorobenzoate, 2,4,6-trimethylbenzoate, 2,4,6-trifluorobenzoate, 3,4,5-trifluorobenzoate, 2,4,6-trichlorobenzoate, 2,3,5-trichlorobenzoate, 2,3,5-triiodobenzoate, 2-bromo-4,5-dimethoxybenzoate, 3,4,5-trimethoxybenzoate, 3,4,5-triethoxybenzoate, 4,5-dimethoxy-2-nitrobenzoate, 3,5-dinitro-o-toluate, 3,5-dinitro-p-toluate, 2-chloro-3,5-dinitrobenzoate, 4-chloro-3,5-dinitrobenzoate, 2,5-dichloro-3-nitrobenzoate, 2,6-dichloro-3-nitrobenzoate, 2,3,4-trimethoxybenzoate, 2,4,5-trifluorobenzoate, 2-chloro-4,5-difluorobenzoate, 2,4-dichloro-5-fluorobenzoate, 2,4,5-trimethoxybenzoate, 2,3,4,5-tetrafluorobenzoate, 2,3,5,6-tetrafluorobenzoate, 2,4-dichloro-3,5-dinitrobenzoate, 2,3,5,6-tetrafluoro-p-toluate, 4-bromo-2,3,5,6-tetrafluorobenzoate, pentafluorobenzoate, 2-biphenylcarboxylate, 4'-(trifluoromethyl)-2-biphenylcarboxylate, 4-biphenylcarboxylate, 4'-ethyl-4-biphenylcarboxylate, 4'-octyloxy-4-biphenylcarboxylate, alpha-phenyl-o-toluate, 2-bibenzylcarboxylate, 2,3,4,5,6-pentafluorophenoxyacetate, 2-phenoxybenzoate, 3-phenoxybenzoate, 2-benzoylbenzoate, 3-benzoylbenzoate, 4-benzoylbenzoate, 2-(4-fluorobenzoyl)benzoate, 2-(4-chlorobenzoyl)benzoate, 2-(4-chloro-3-nitrobenzoyl)benzoate, 1-naphthoate, 2-naphthoate, 4-fluoro-1-naphthoate, 2-ethoxy-1-naphthoate, 1,8-naphthalaldehydate, naphthenate, 2-biphenylenecarboxylate, gamma-oxo-5-acenaphthenebutyrate, 9-fluorenecarboxylate, 1-fluorenecarboxylate, 4-fluorenecarboxylate, 9-fluorenone-1-carboxylate, 9-fluorenone-2-carboxylate, 9-fluorenone-4-carboxylate, 7-nitro-4-fluorenecarboxylate, chromone-2-carboxylate, 9-anthracenecarboxylate, anthraquinone-2-carboxylate, xanthene-9-carboxylate, 1-pyrenecarboxylate, malonate, methylmalonate, ethylmalonate, butylmalonate, dimethylmalonate, diethylmalonate, succinate, methylsuccinate, dimethylsuccinate, 2-ethyl-2-methylsuccinate, 2,3-dimethylsuccinate, glutarate, 2-methylglutarate, 3-methylglutarate, 2,2-dimethylglutarate, 3,3-dimethylglutarate, 2-ketoglutarate, adipate, 3-methyladipate, 3-tert-butyladipate, pimelate, suberate, azelate, sebacate, perfluorosebacate, 1,11-undecanedicarboxylate, undecanedioate, 1,10-decanedicarboxylate, 1,12-dodecanedioate, hexadecanedioate, docosanedioate, tetracosanedioate, itaconate, maleate, fumarate, citraconate, mesaconate, glutaconate, β-hydromuconate, traumatate, muconate, chlorosuccinate, bromosuccinate, 2,3-dibromosuccinate, tetrafluorosuccinate, hexafluoroglutarate, perfluoroadipate, perfluorosuberate, 3-chlorododecanedioate, dibromomaleate, diglycolate, 3,6-dioxaoctanedioate, thiodiglycolate, 3,3'-thiodipropionate, 1,3-acetonedicarboxylate, 3-oxoadipate, 4-ketopimelate, 5-oxoazelate, chelidonate, 1,2-cyclopentanedicarboxylate, 3,3-tetramethyleneglutarate, camphorate, cyclohexylsuccinate, 1,1-cyclohexanediacetate, 1,2-cyclohexanedicarboxylate, 1,3-cyclohexanedicarboxylate, 1,4-cyclohexanedicarboxylate, 1,3-adamantanedicarboxylate, 1,3-adamantanediacetate, 5-norbornene-2,3-dicarboxylate, 1,4,5,6,7,7-hexachloro-5-norbornene-2,3-dicarboxylate, phenylsuccinate, 3-phenylglutarate, 1,2-phenylenediacetate, 1,2-phenylenedioxydiacetate, homophthalate, 1,3-phenylenediacetate, 4-carboxyphenoxyacetate, 1,4-phenylenediacetate, 1,4-phenylenedipropionate, 2-carboxycinnamate, 1,4-phenylenediacrylate, 2-carboxybenzenepropanoate, 4,4'-(hexafluoroisopropylidene)bis(benzoate), 4,4'-oxybis(benzoate), phthalate, isophthalate, terephthalate, 3-fluorophthalate, 2-methoxyisophthalate, 3-nitrophathalate, 4-methylphthalate, 2-bromoterephthalate, 4-bromoisophthalate, 4-nitrophthalate, nitroterephthalate, 5-tert-butylisophthalate, 5-octadecyloxyisophthalate, 5-nitroisophthalate, 4,5-dichlorophthalate, tetrafluoroterephthalate, tetrafluoroisophthalate, tetrafluorophthalate, diphenate, 4,4'-biphenyldicarboxylate, 4-[4-(2-carboxybenzoyl)phenyl]butyrate, 1,4-naphthalenedicarboxylate, 2,3-naphthalenedicarboxylate, 2,6-naphthalenedicarboxylate, 2,7-di-tert-butyl-9,9-dimethyl-4,5-xanthenedicarboxylate, phenylmalonate, benzylmalonate, tricarballylate, aconitate, nitromethanetrispropionate, 1,3,5-cyclohexanetricarboxylate, 1,3,5-trimethyl-1,3,5-cyclohexanetricarboxylate, 1,2,3-benzenetricarboxylate, 1,2,4-benzenetricarboxylate, 1,3,5-benzenetricarboxylate, 5-(4-carboxy-2-nitrophenoxyisophthalate, 1,2,3,4-butanetetracarboxylate, tetrahydrofuran-2,3,4,5-tetracarboxylate, 2,2',2'',2'''-[1,2-ethanediylidenetetrakis(thio)]-tetrakisacetate, cyclobutanetetracarboxylate, 1,2,4,5-benzenetetracarboxylate, 1,4,5,8-naphthalenetetracarboxylate, 1,2,3,4,5,6-cyclohexanehexacarboxylate, mellitate, methanesulfonate, ethanesulfonate, 1-propanesulfonate, 2-propanesulfonate, 1-butanesulfonate, 1-pentanesulfonate, 1-hexanesulfonate, 1-heptanesulfonate, 1-octanesulfonate, 1-nonanesulfonate, 1-decanesulfonate, 1-dodecanesulfonate, 1-tetradecanesulfonate, 1-hexadecanesulfonate, vinylsulfonate, 2-methyl-2-propene-1-sulfonate, trifluoromethanesulfonate, 2-chloroethanesulfonate, 2-bromoethanesulfonate, nonafluoro-1-butanesulfonate, perfluoro-1-octanesulfonate, PIPES, of the formula

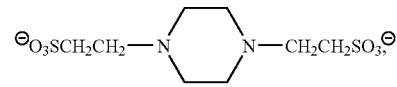

MES, of the formula

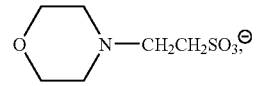

MOPS, of the formula

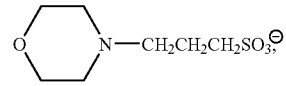

10-camphorsulfonate, 3-bromocamphor-8-sulfonate, 3-bromocamphor-10-sulfonate, 3-sulfopropylacrylate, 3-sulfopropylmethacrylate, dioctyl sulfosuccinate, p-toluene sulfonate, 4-ethylbenzenesulfonate, 4-chlorobenzenesulfonate, 2,4-dinitrobenzenesulfonate, 2-mesitylenesulfonate, 1-naphthalenesulfonate, 2-naphthalenesulfonate, 5-dimethylamino-1-naphthalenesulfonate, 1,5-naphthalene disulfonate, 4-sulfo-1,8-naphthalic anhydride salt, benzenesulfonate, xylenesulfonate, 4-octylbenzenesulfonate, dodecylbenzenesulfonate, 4-styrenesulfonate, 3-nitrobenzenesulfonate, 2-formylbenzenesulfonate, 4-acetylbenzenesulfonate, 4-sulfophenylisothiocyanate salt, 1,2-benzenedisulfonate, 1,3-benzenedisulfonate, 2-formyl-1,3-benzenedisulfonate, 4-chloro-3-nitrobenzenesulfonate, 4,4'-diisothiocyanato-2,2'-distilbenesulfonate, pentafluorobenzenesulfonate, 1,2-naphthoquinone-4-sulfonate, 2,6-naphthalenedisulfonate, 1,3,6-naphthalenetrisulfonate, 1,3,7-naphthalenetrisulfonate, 9,10-dimethoxy-2-anthracenesulfonate, anthraquinone-2-sulfonate, anthraquinone-1,5-disulfonate, anthraquinone-2,6-disulfonate, sulfoacetate, sulfosuccinate, 2-sulfobenzoate, 3-sulfobenzoate, 4-sulfobenzoate, 4-sulfophthalate, 5-sulfoisophthalate, dimethyl-5-sulfoisophthalate, diethyldithiocarbamate, or mixtures thereof;

and

CA is either a hydrogen atom or a cation associated with all but one of the $Q^-$ groups.

2. A compound according to claim 1 wherein M is a metal ion of a metal selected from magnesium, calcium, strontium, barium, radium, aluminum, gallium, germanium, indium, tin, antimony, tellurium, thallium, lead, bismuth, polonium, scandium, titanium, vanadium, chromium, manganese, iron, cobalt, nickel, copper, zinc, zirconium, niobium molybdenum, technetium, ruthenium, rhodium, palladium, silver, cadmium, hafnium, tantalum, tungsten, rhenium, osmium, iridium, platinum, gold, mercury, metals of the lanthanide series, metals of the actinide series, and mixtures thereof.

3. A compound according to claim 1 wherein M is a metal ion of a metal selected from zinc, calcium, bismuth, tin, iron, copper, aluminum, nickel, titanium, chromium, or mixtures thereof.

4. A compound according to claim 1 wherein M is a zinc metal ion.

5. A compound according to claim 1 wherein M is a metal-containing moiety which is a metal ionic moiety.

6. A compound according to claim 1 wherein M is a metal-containing moiety which is a metal coordination compound.

7. A compound according to claim 1 wherein M is a metal-containing moiety which is a heteropolyacid.

8. A compound according to claim 7 wherein the heteropolyacid is a phosphotungstic acid, a silicotungstic acid, a phosphomolybdic acid, or a mixture thereof.

9. A compound according to claim 1 wherein a, b, and c are each zero.

10. A compound according to claim 1 wherein d is 1.

11. A compound according to claim 1 wherein d is 2.

12. A compound according to claim 1 wherein d is 1 and $Q^-$ is a $COO^-$ group.

13. A compound according to claim 1 wherein d is 1 and $Q^-$ is a $SO_3^-$ group.

14. A compound according to claim 1 wherein the chromogen is of the formula

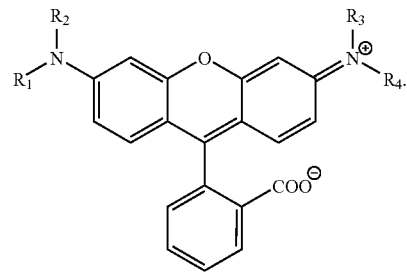

15. A compound according to claim 1 wherein the chromogen is of the formula

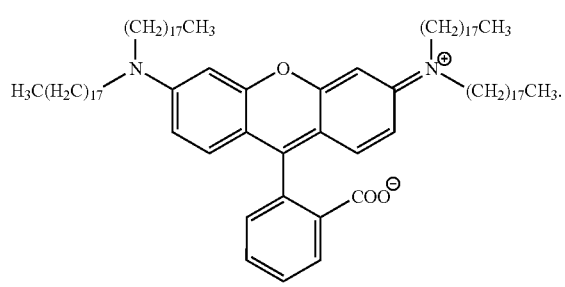

16. A compound according to claim 1 wherein the chromogen is of the formula

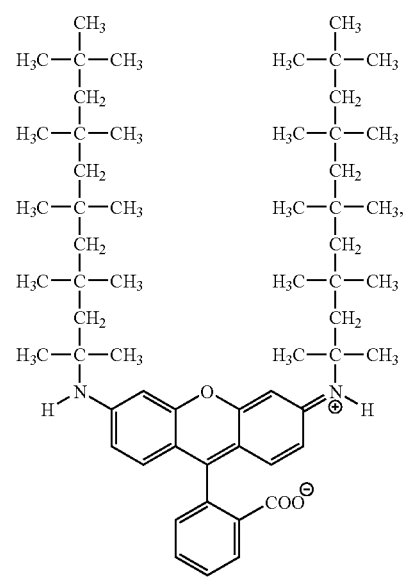

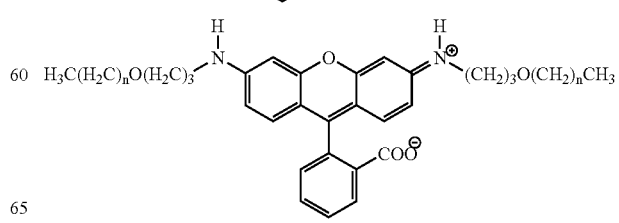

wherein n is at least 11,

127
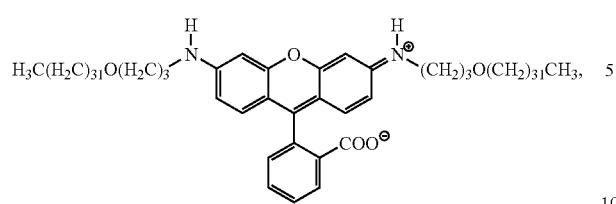
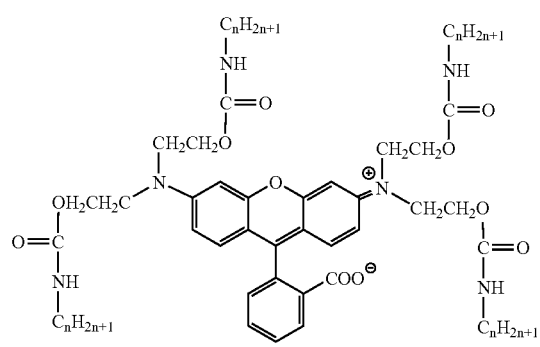
wherein n is at least 12,
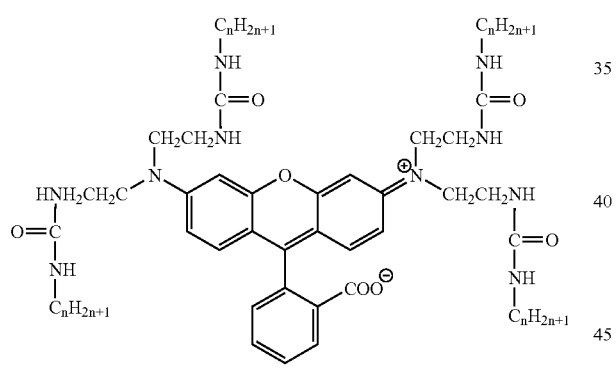
wherein n is at least 12,
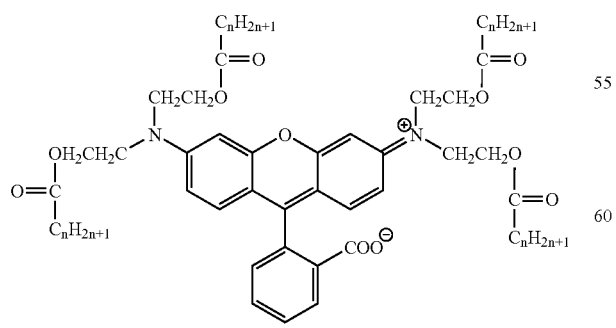
wherein n is at least 12,
128
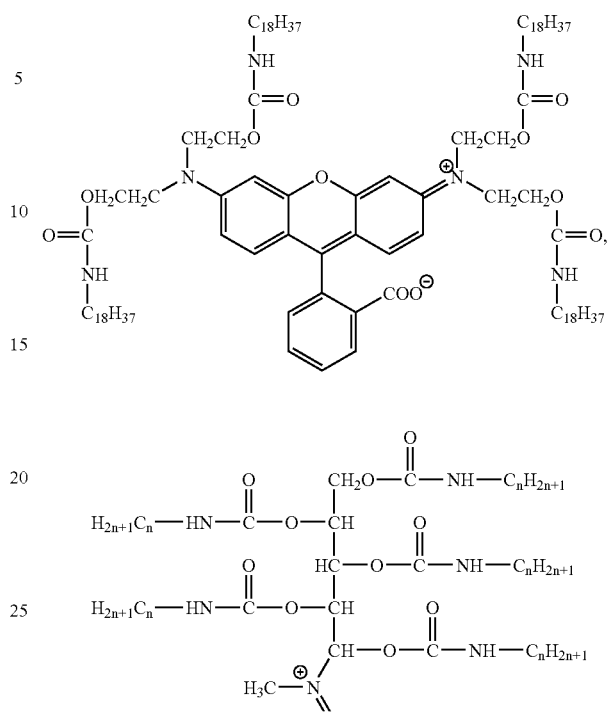
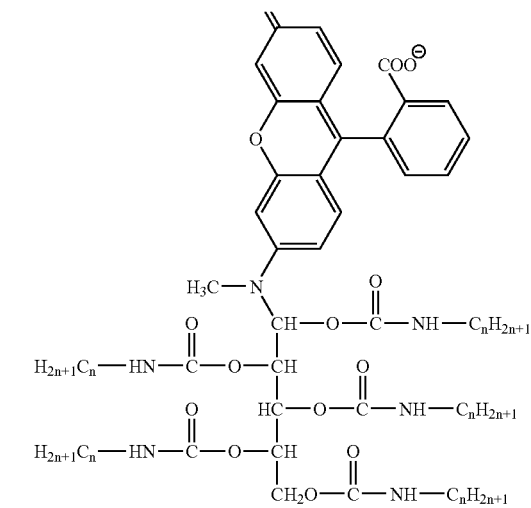
wherein n is at least 12,
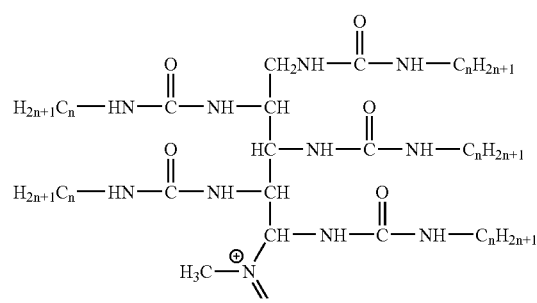

129
-continued
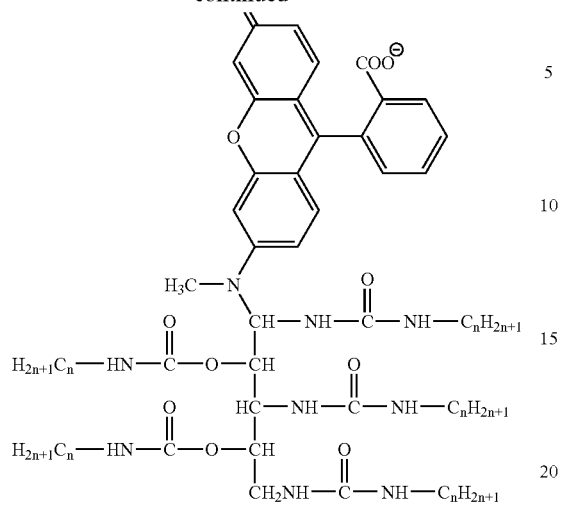
wherein n is at least 12,
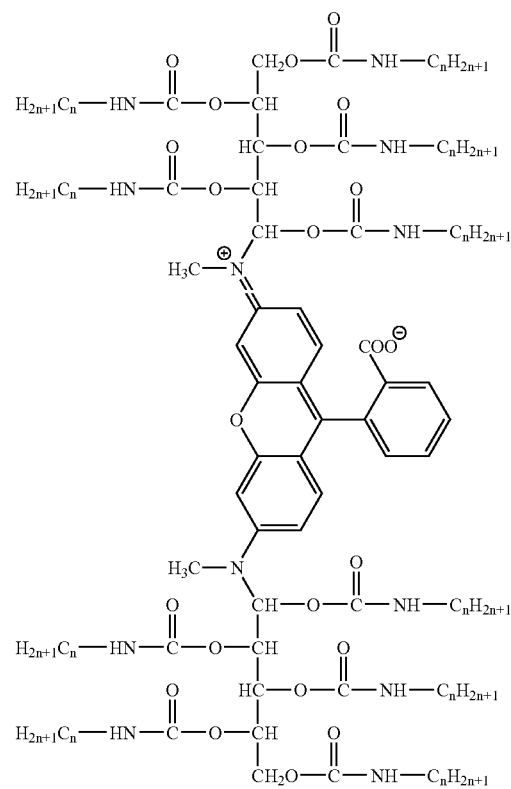
wherein n is at least 12,
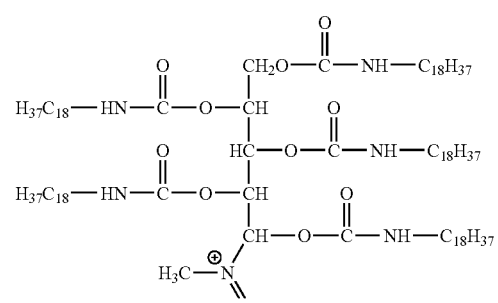
130
-continued
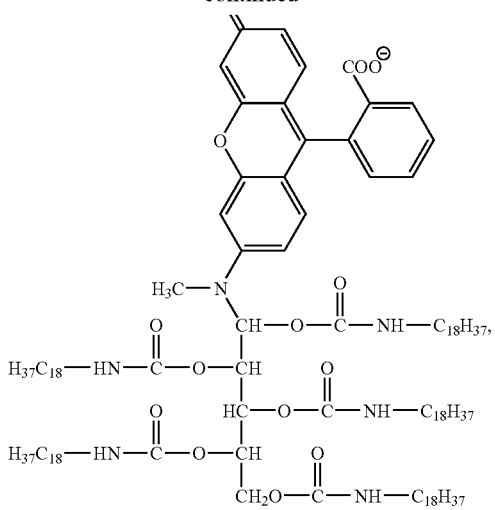
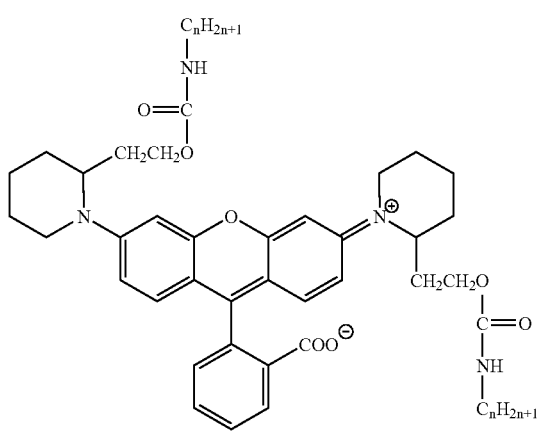
wherein n is at least 12,
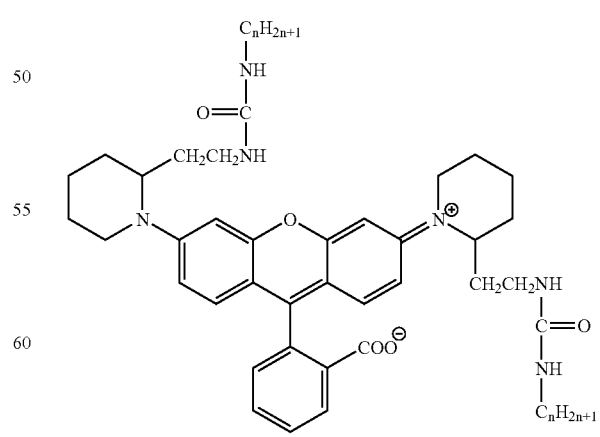
wherein n is at least 12,

131
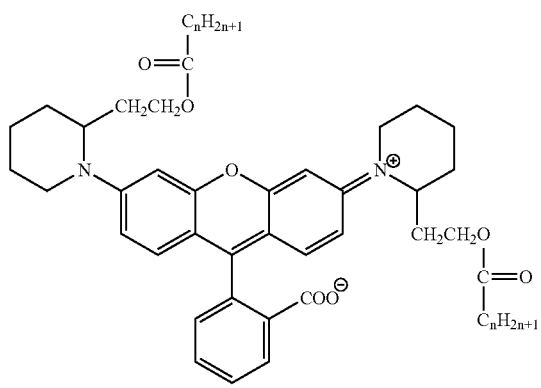
wherein n is at least 12,
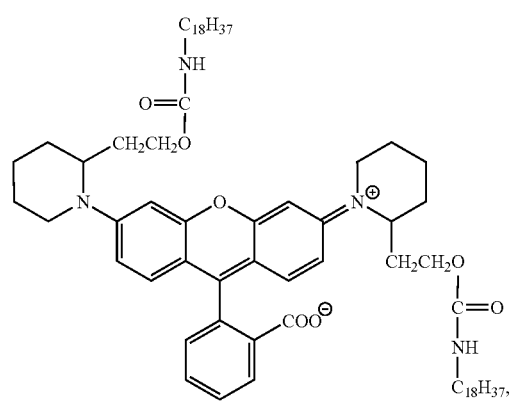
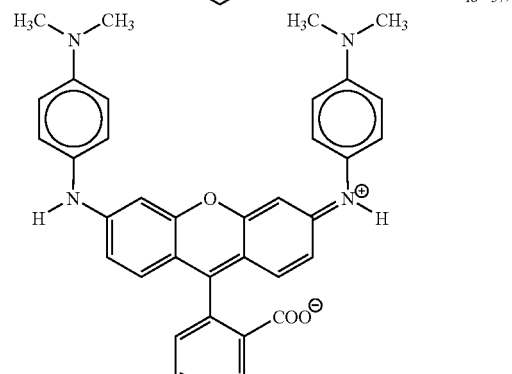
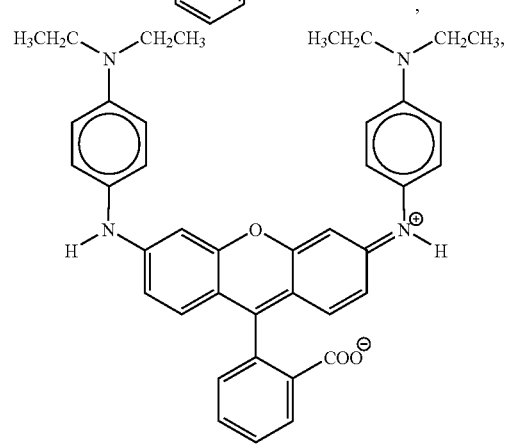
132
-continued
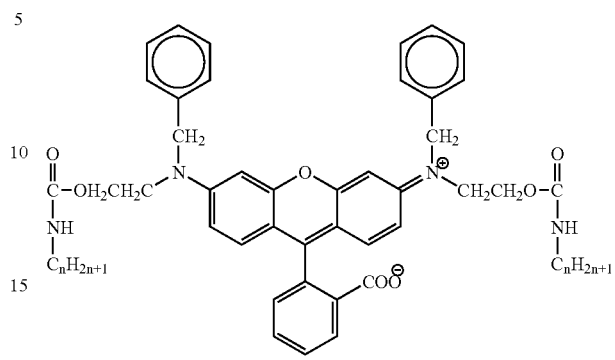
wherein n is at least 12,
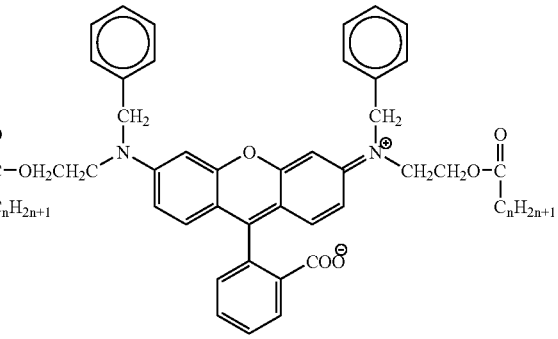
wherein n is at least 12,
wherein n is at least 12,

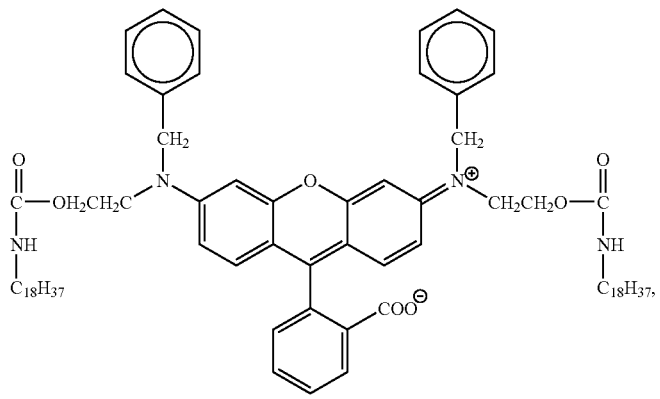
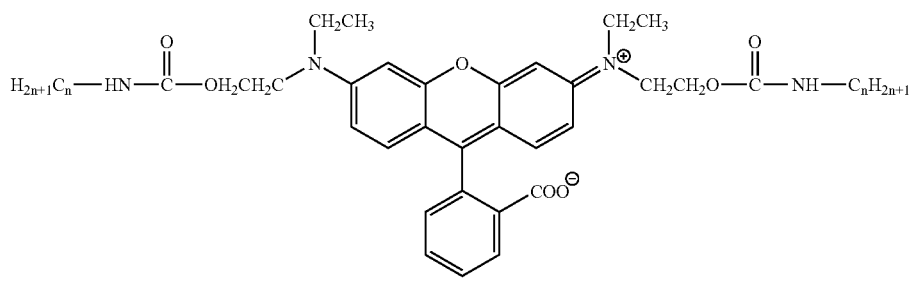
wherein n is at least 12,
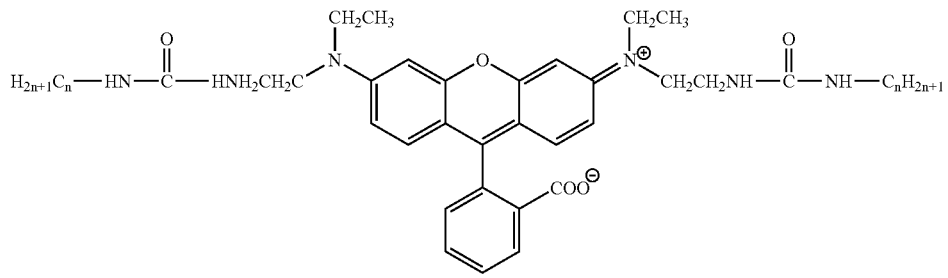
wherein n is at least 12,
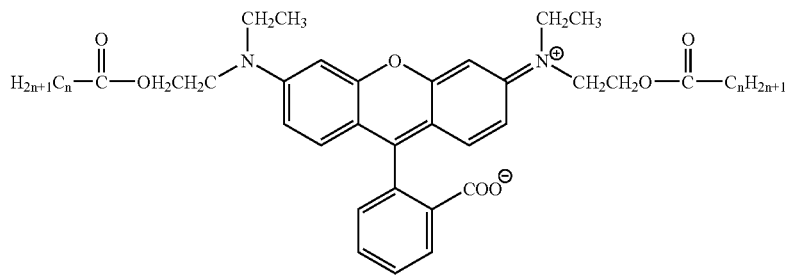
wherein n is at least 12,

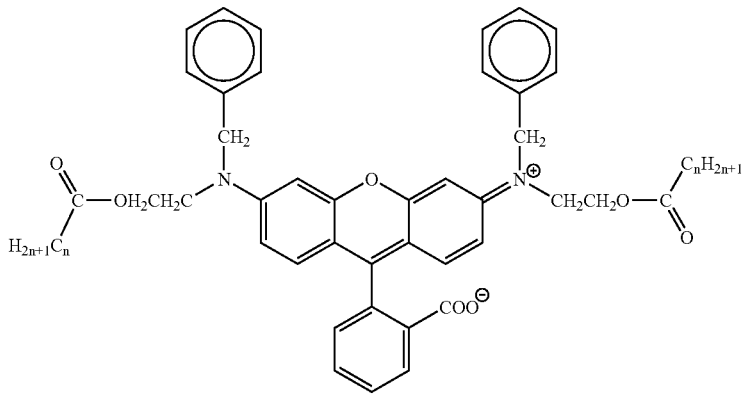
wherein n has an average value of at least 12,
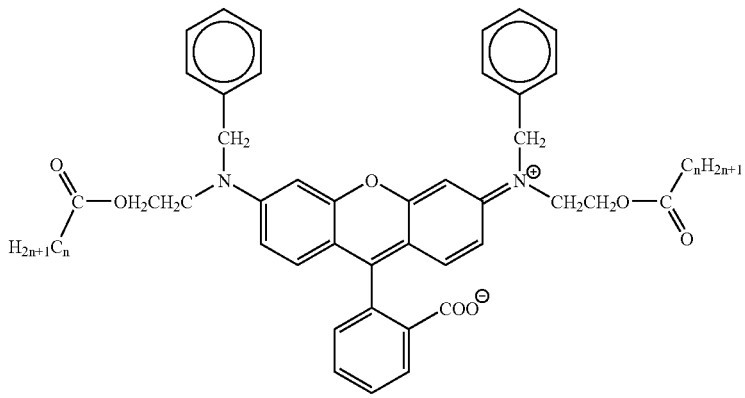
wherein n has an average value of about 50,
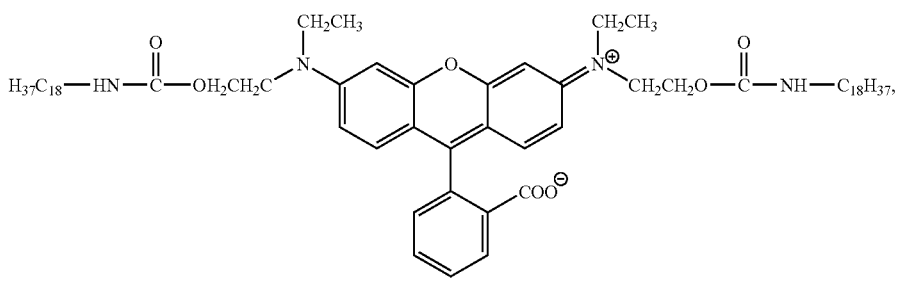
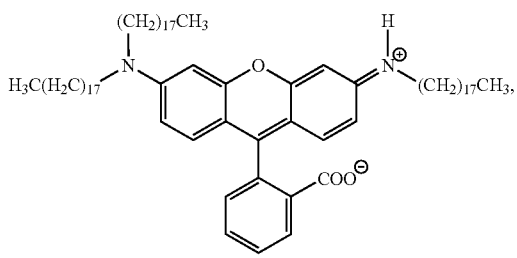
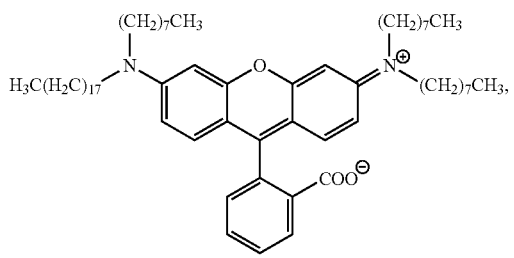

-continued

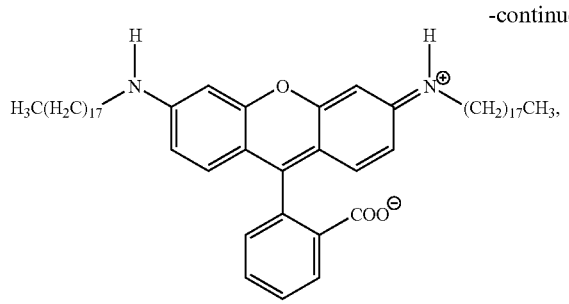

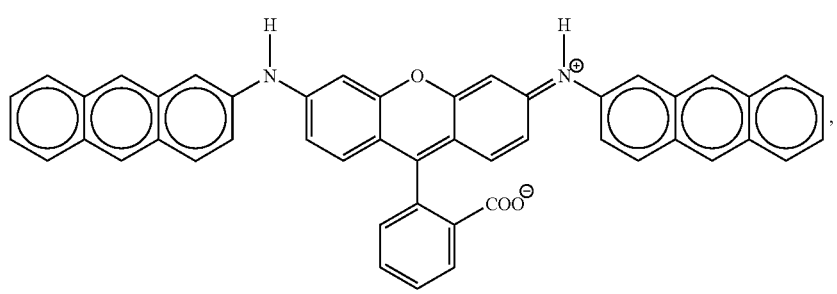

or mixtures thereof.

17. A compound according to claim 1 wherein M is a zinc cation, y is 2, and the chromogen is of the formula

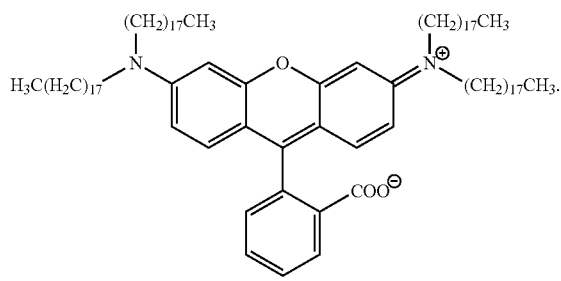

18. A compound according to claim 17 wherein z is 2.

19. A compound according to claim 1 wherein M is a calcium cation, y is 2, and the chromogen is of the formula

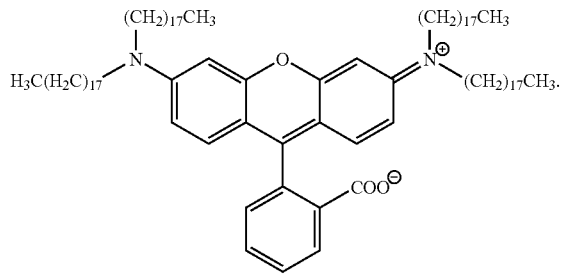

20. A compound according to claim 19 wherein z is 2.

21. A compound according to claim 1 wherein M is a bismuth cation, y is 3, and the chromogen is of the formula

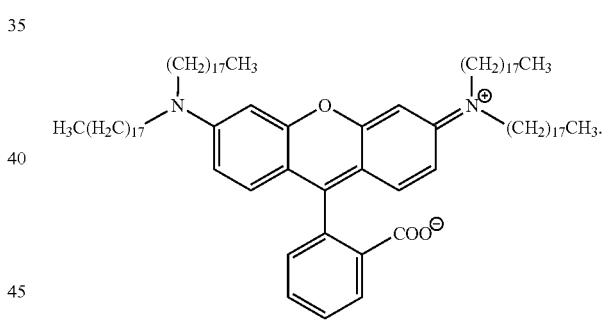

22. A compound according to claim 21 wherein z is 3.

23. A compound according to claim 1 wherein M is a tin cation, y is 2, and the chromogen is of the formula

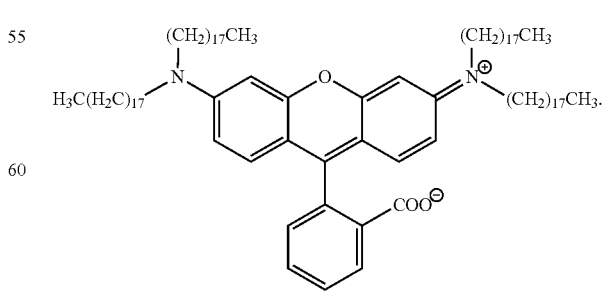

24. A compound according to claim 23 wherein z is 2.

25. A compound according to claim 1 wherein M is an iron cation, y is 2, and the chromogen is of the formula

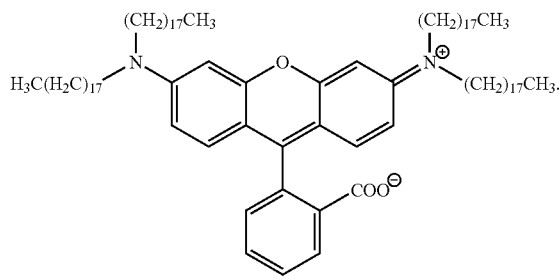

26. A compound according to claim 25 wherein z is 2.
27. A compound according to claim 1 wherein M is a copper cation, y is 2, and the chromogen is of the formula

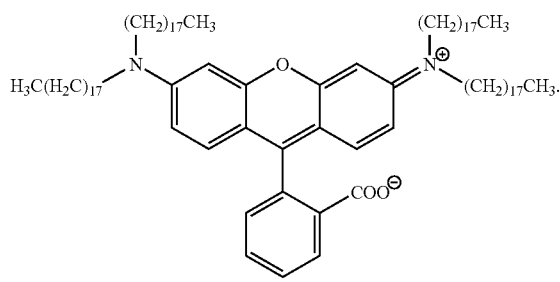

28. A compound according to claim 27 wherein z is 2.
29. A compound according to claim 1 wherein M is an aluminum cation, y is 3, and the chromogen is of the formula

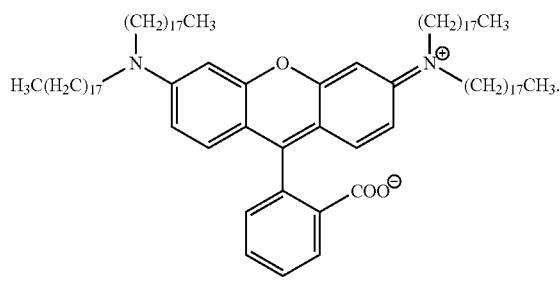

30. A compound according to claim 29 wherein z is 3.
31. A compound according to claim 1 wherein M is a nickel cation, y is 2, and the chromogen is of the formula

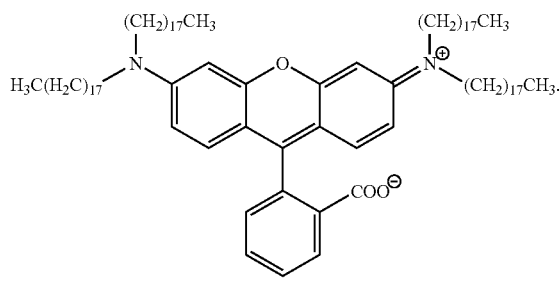

32. A compound according to claim 31 wherein z is 2.

33. A compound according to claim 1 wherein M is a titanium cation, y is 4, and the chromogen is of the formula

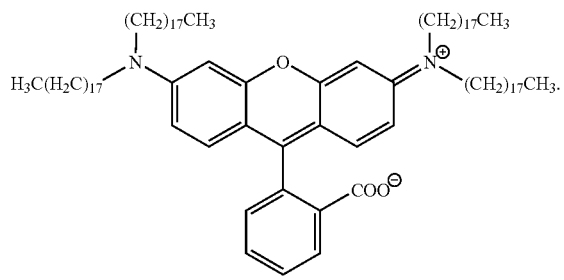

34. A compound according to claim 33 wherein z is 4.
35. A compound according to claim 1 wherein M is a chromium cation, y is 3, and the chromogen is of the formula

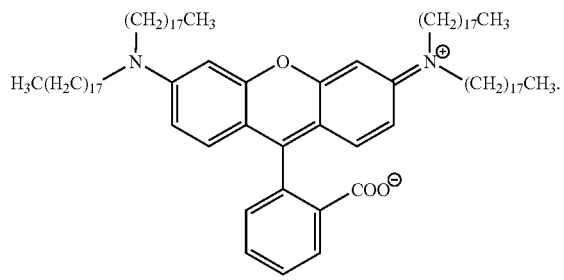

36. A compound according to claim 35 wherein z is 3.
37. A compound of the formula

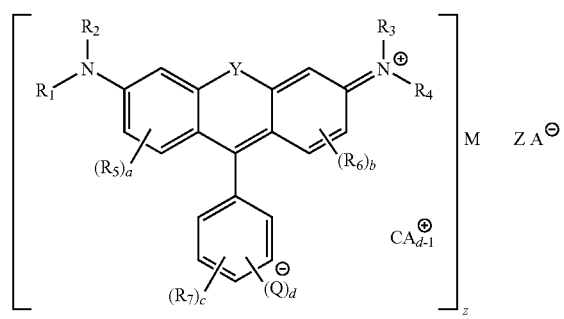

wherein M is either (1) a metal ion having a positive charge of +y wherein y is an integer which is at least 2, said metal ion being capable of forming a compound with at least two

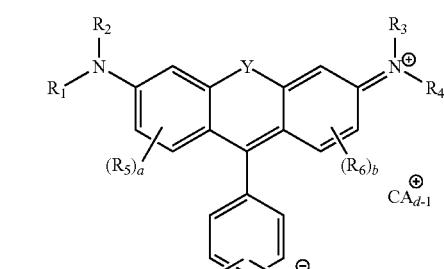

chromogen moieties, or (2) a metal-containing moiety capable of forming a compound with at least two

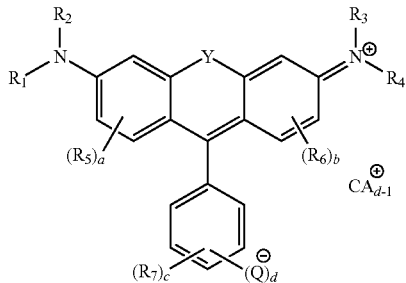

chromogen moieties, z is an integer representing the number of

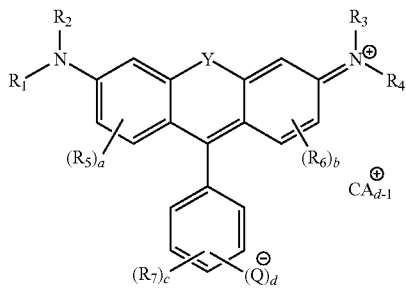

chromogen moieties associated with the metal and is at least 2, $R_1$, $R_2$, $R_3$, and $R_4$ each, independently of the others, is (i) a hydrogen atom, (ii) an alkyl group, (iii) an aryl group, (iv) an arylalkyl group, or (v) an alkylaryl group, wherein $R_1$ and $R_2$ can be joined together to form a ring, wherein $R_3$ and $R_4$ can be joined together to form a ring, and wherein $R_1$, $R_2$, $R_3$, and $R_4$ can each be joined to a phenyl ring in the central structure, provided that the number of carbon atoms in $R_1+R_2+R_3+R_4$ is at least 16 a and b each, independently of the others, is an integer which is 0, 1, 2, or 3, c is an integer which is 0, 1, 2, 3, or 4, each $R_5$, $R_6$, and $R_7$, independently of the others, is (i) an alkyl group, (ii) an aryl group, (iii) an arylalkyl group, (iv) an alkylaryl group, (v) a halogen atom, (vi) an ester group, (vii) an amide group, (viii) a sulfone group, (ix) an amine group or ammonium group, (x) a nitrile group, (xi) a nitro group, (xii) a hydroxy group, (xiii) a cyano group, (xiv) a pyridine or pyridinium group, (xv) an ether group, (xvi) an aldehyde group, (xvii) a ketone group, (xviii) a carbonyl group, (xix) a thiocarbonyl group, (xx) a sulfate group, (xxi) a sulfide group, (xxii) a sulfoxide group, (xxiii) a phosphine or phosphonium group, (xxiv) a phosphate group, (xxv) a mercapto group, (xxvi) a nitroso group, (xxvii) an acyl group, (xxviii) an acid anhydride group, (xxix) an azide group, (xxx) an azo group, (xxxi) a cyanato group, (xxxii) an isocyanato group, (xxxiii) a thiocyanato group, (xxxiv) an isothiocyanato group, (xxxv) a urethane group, or (xxxvi) a urea group, wherein $R_5$, $R_6$, and $R_7$ can each be joined to a phenyl ring in the central structure,

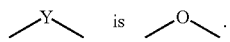

$Q^-$ is a $COO^-$ group or a $SO_3^-$ group, d is an integer which is 2,

A is an organic anion, and

CA is either a hydrogen atom or a cation associated with all but one of the $Q^-$ groups.

38. A compound of the formula

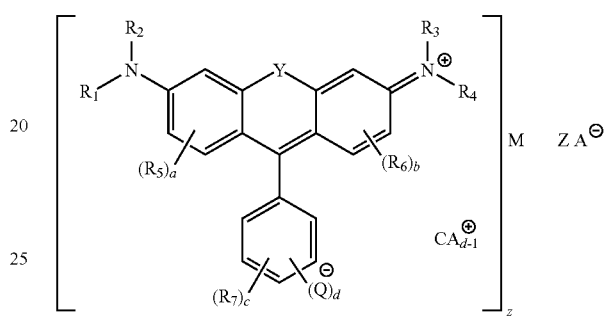

wherein M is either (1) a metal ion having a positive charge of +y wherein y is an integer which is at least 2, said metal ion being capable of forming a compound with at least two

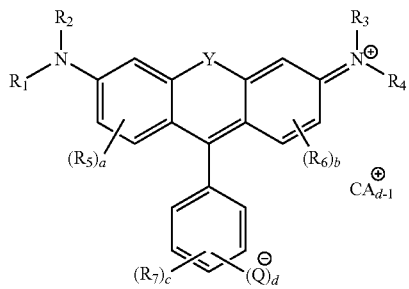

chromogen moieties, or (2) a metal-containing moiety capable of forming a compound with at least two

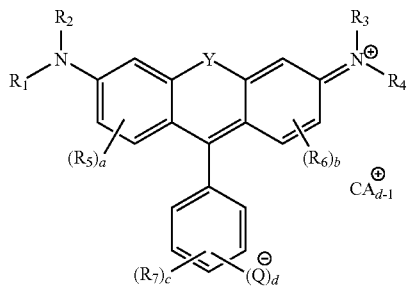

chromogen moieties, z is an integer representing the number of

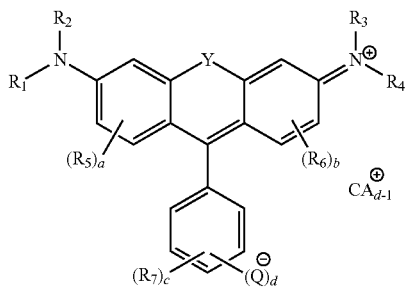

chromogen moieties associated with the metal and is at least 2, $R_1$, $R_2$, $R_3$, and $R_4$ each, independently of the others, is (i) a hydrogen atom, (ii) an alkyl group, (iii) an aryl group, (iv) an arylalkyl group, or (v) an alkylaryl group, wherein $R_1$ and $R_2$ can be joined together to form a ring, wherein $R_3$ and $R_4$ can be joined together to form a ring, and wherein $R_1$, $R_2$, $R_3$, and $R_4$ can each be joined to a phenyl ring in the central structure, provided that the number of carbon atoms in $R_1+R_2+R_3+R_4$ is at least 16 a and b each, independently of the others, is an integer which is 0, 1, 2, or 3, c is an integer which is 0, 1, 2, 3, or 4, each $R_5$, $R_6$, and $R_7$, independently of the others, is (i) an alkyl group, (ii) an aryl group, (iii) an arylalkyl group, (iv) an alkylaryl group, (v) a halogen atom, (vi) an ester group, (vii) an amide group, (viii) a sulfone group, (ix) an amine group or ammonium group, (x) a nitrile group, (xi) a nitro group, (xii) a hydroxy group, (xiii) a cyano group, (xiv) a pyridine or pyridinium group, (xv) an ether group, (xvi) an aldehyde group, (xvii) a ketone group, (xviii) a carbonyl group, (xix) a thiocarbonyl group, (xx) a sulfate group, (xxi) a sulfide group, (xxii) a sulfoxide group, (xxiii) a phosphine or phosphonium group, (xxiv) a phosphate group, (xxv) a mercapto group, (xxvi) a nitroso group, (xxvii) an acyl group, (xxviii) an acid anhydride group, (xxix) an azide group, (xxx) an azo group, (xxxi) a cyanato group, (xxxii) an isocyanato group, (xxxiii) a thiocyanato group, (xxxiv) an isothiocyanato group, (xxxv) a urethane group, or (xxxvi) a urea group, wherein $R_5$, $R_6$, and $R_7$ can each be joined to a phenyl ring in the central structure,

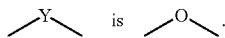

$Q^-$ is a $SO_3^-$ group, d is an integer which is 1,

A is an organic anion, and

CA is either a hydrogen atom or a cation associated with all but one of the $Q^-$ groups.

39. A compound of the formula

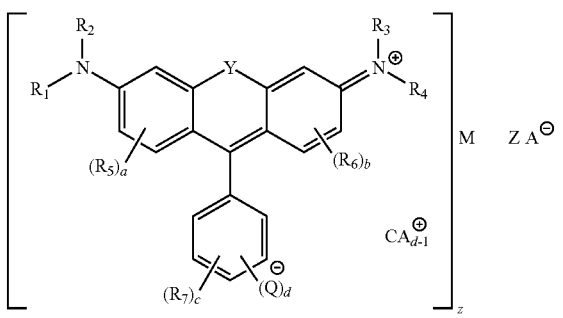

wherein M is either (1) a metal ion having a positive charge of +y wherein y is an integer which is at least 2, said metal ion being capable of forming a compound with at least two

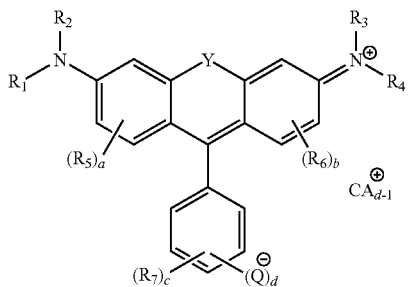

chromogen moieties, or (2) a metal-containing moiety capable of forming a compound with at least two

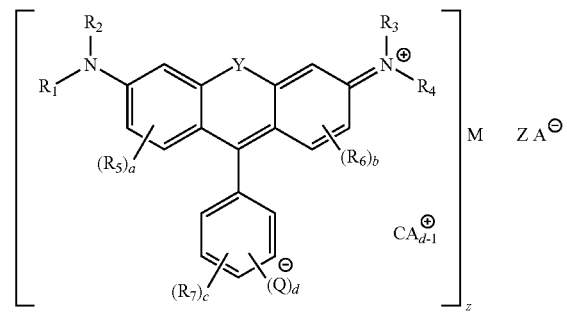

chromogen moieties, z is an integer representing the number of

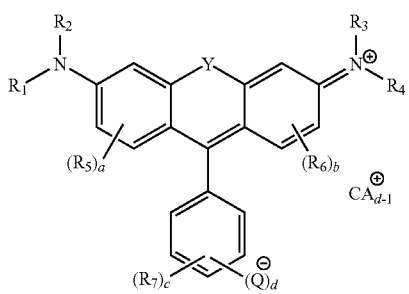

chromogen moieties associated with the metal and is at least 2, $R_1$, $R_2$, $R_3$, and $R_4$ each, independently of the others, is (i) a hydrogen atom, (ii) an alkyl group, (iii) an aryl group, (iv) an arylalkyl group, or (v) an alkylaryl group, wherein $R_1$ and $R_2$ can be joined together to form a ring, wherein $R_3$ and $R_4$ can be joined together to form a ring, and wherein $R_1$, $R_2$, $R_3$, and $R_4$ can each be joined to a phenyl ring in the central structure, a and b each, independently of the others, is an integer which is 0, 1, 2, or 3, c is an integer which is 0, 1, 2, 3, or 4, each $R_5$, $R_6$, and $R_7$, independently of the others, is (i) an alkyl group, (ii) an aryl group, (iii) an arylalkyl group, (iv) an alkylaryl group, (v) a halogen atom, (vi) an ester group, (vii) an amide group, (viii) a sulfone group, (ix) an amine group or ammonium group, (x) a nitrile group, (xi) a nitro group, (xii) a hydroxy group, (xiii) a cyano group, (xiv) a pyridine or pyridinium group, (xv) an ether group, (xvi) an aldehyde group, (xvii) a ketone group, (xviii) a carbonyl group, (xix) a thiocarbonyl group, (xx) a sulfate group, (xxi) a sulfide group, (xxii) a sulfoxide group, (xxiii) a phosphine or phosphonium group, (xxiv) a phosphate group, (xxv) a mercapto group, (xxvi) a nitroso group, (xxvii) an acyl group, (xxviii) an acid anhydride group, (xxix) an azide group, (xxx) an azo group, (xxxi) a cyanato group, (xxxii) an isocyanato group, (xxxiii) a thiocyanato group, (xxxiv) an isothiocyanato group, (xxxv) a urethane group, or (xxxvi) a urea group, wherein $R_5$, $R_6$, and $R_7$ can each be joined to a phenyl ring in the central structure, provided that the number of carbon atoms in $R_1+R_2+R_3+R_4$ is at least 16

 is 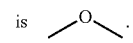.

$Q^-$ is a $COO^-$ group or a $SO_3^-$ group, d is an integer which is 2, 3, 4, or 5, A is an organic anion, CA is either a hydrogen atom or a cation associated with all but one of the $Q^-$ groups; and wherein the chromogen is of the formula

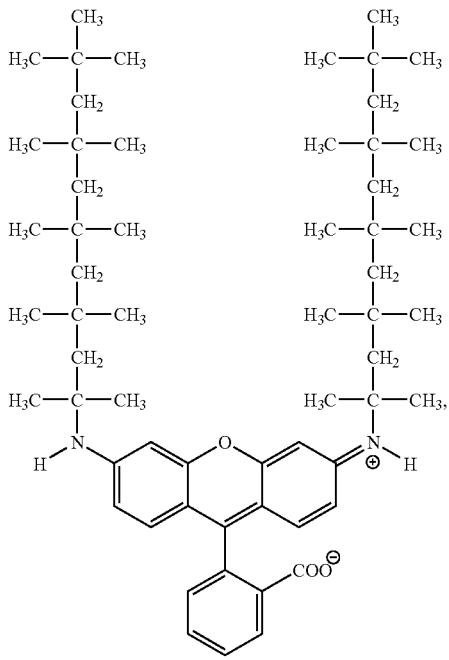

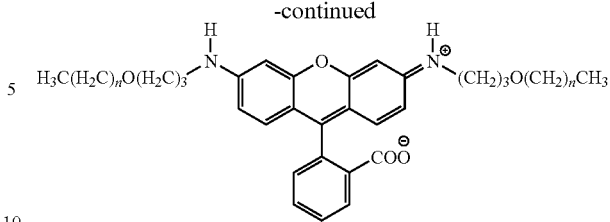

wherein n is at least 11,

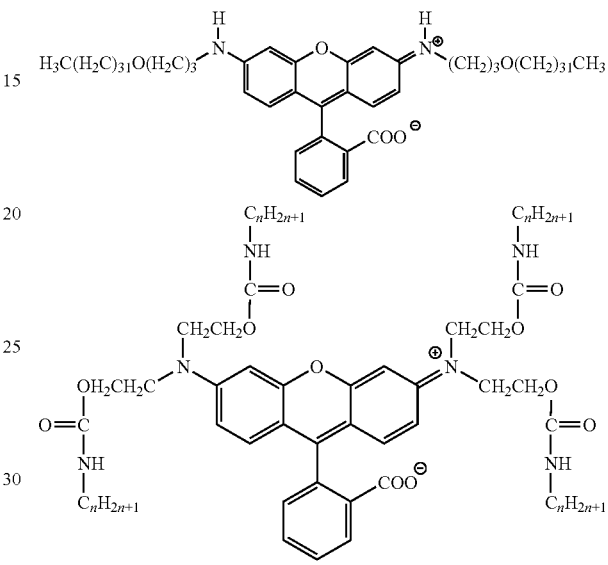

wherein n is at least 12,

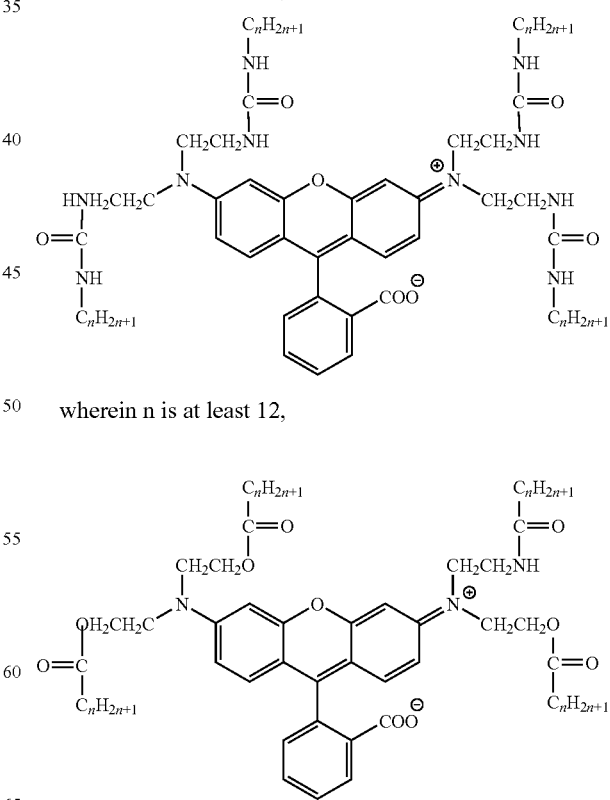

wherein n is at least 12, wherein n is at least 12,

147
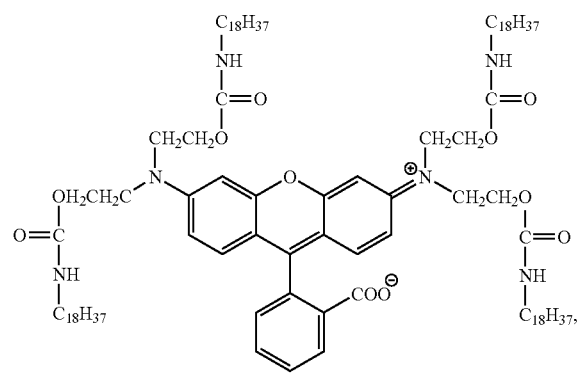
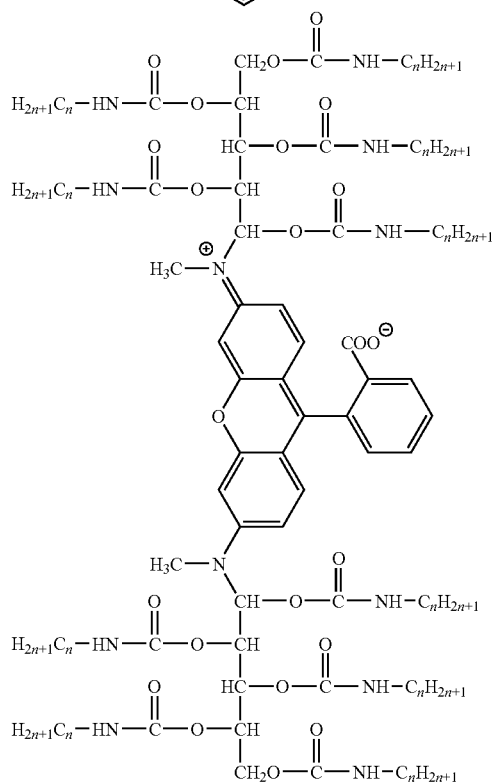
wherein n is at least 12,
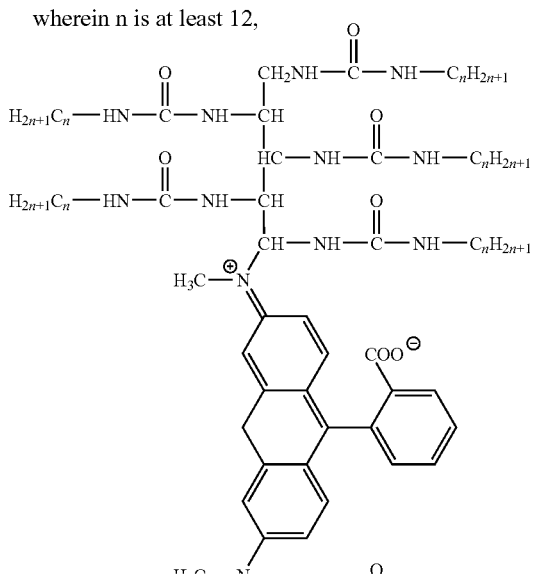
148
-continued
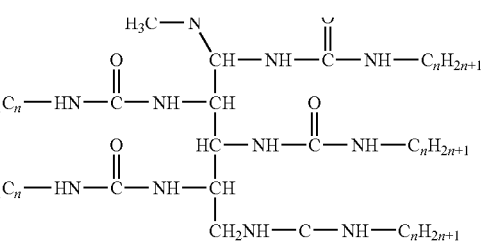
wherein n is at least 12,
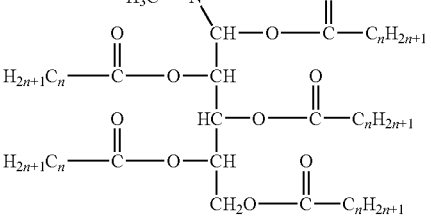
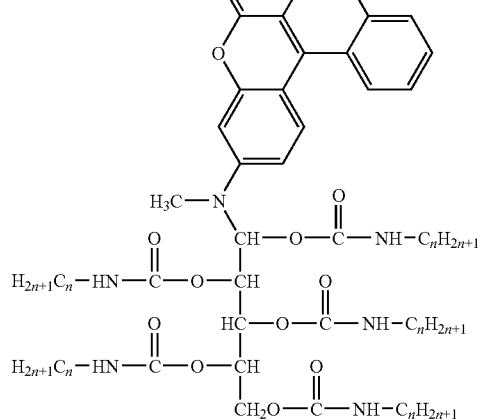
wherein n is at least 12,

149
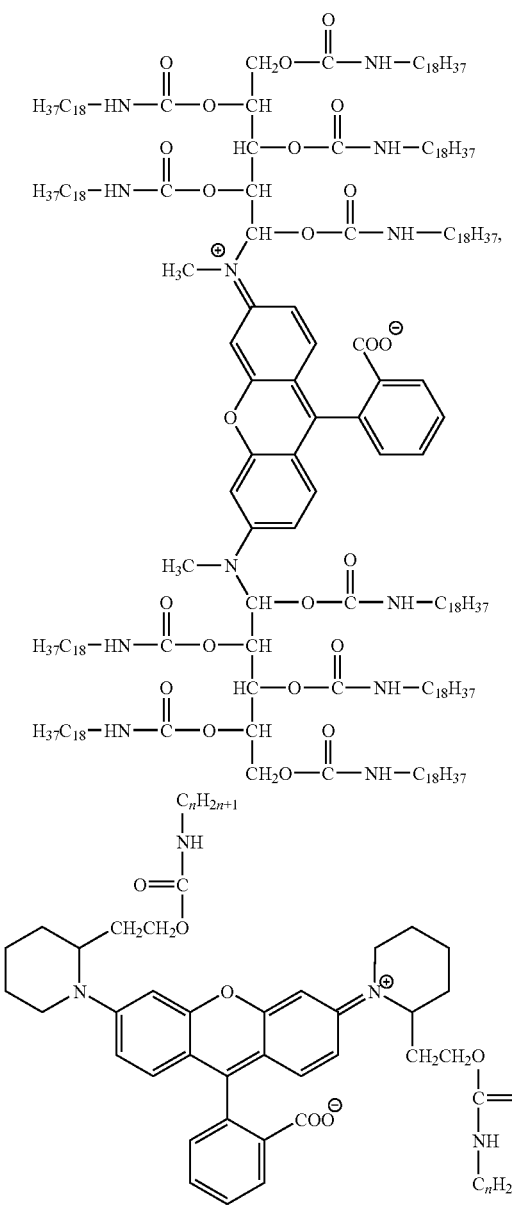
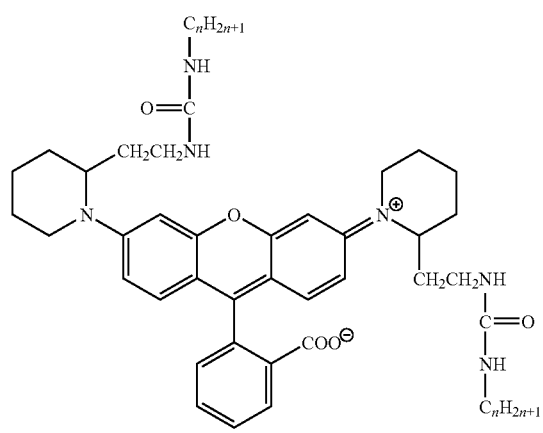
wherein n is at least 12,
150
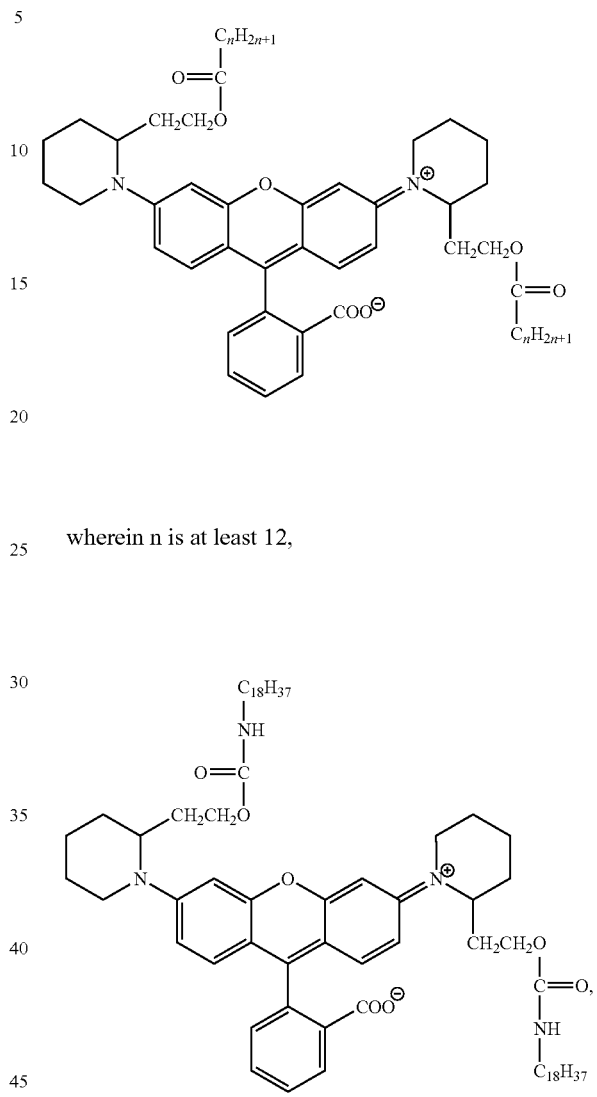
wherein n is at least 12,
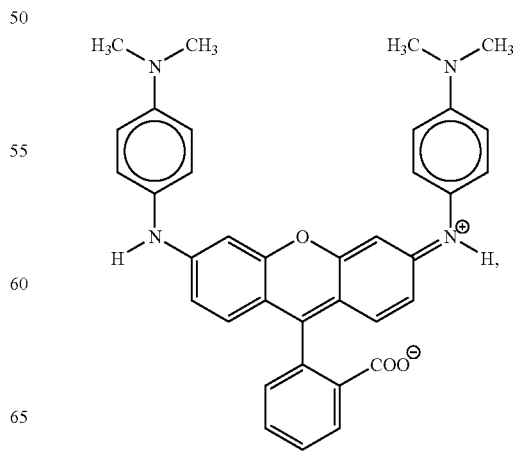

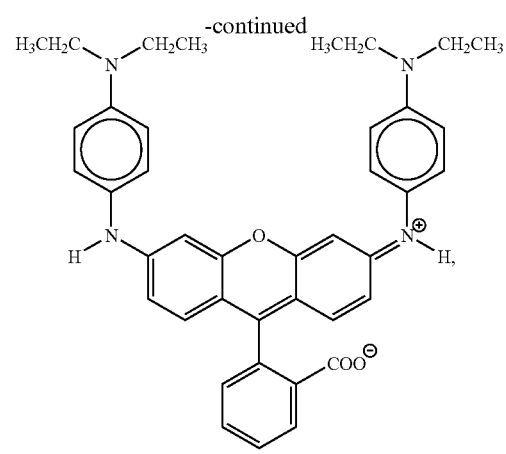
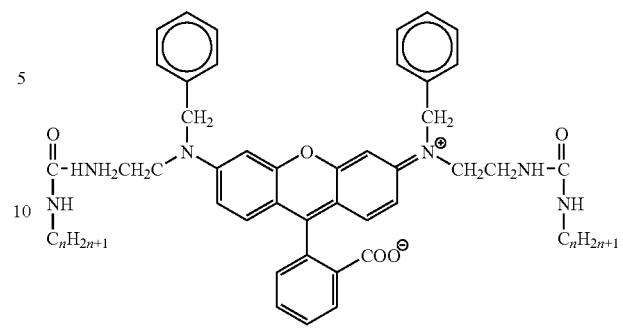
wherein n is at least 12,
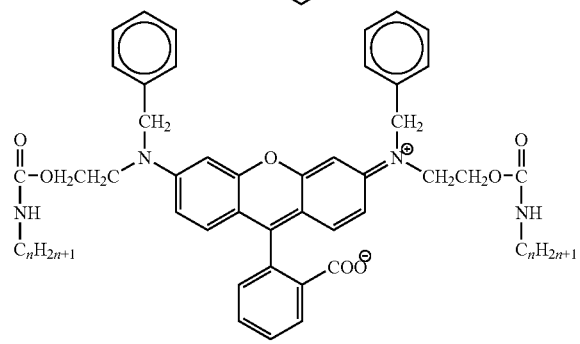
wherein n is at least 12,
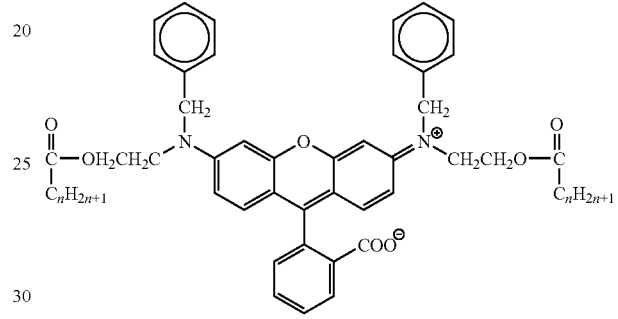
wherein n is at least 12,
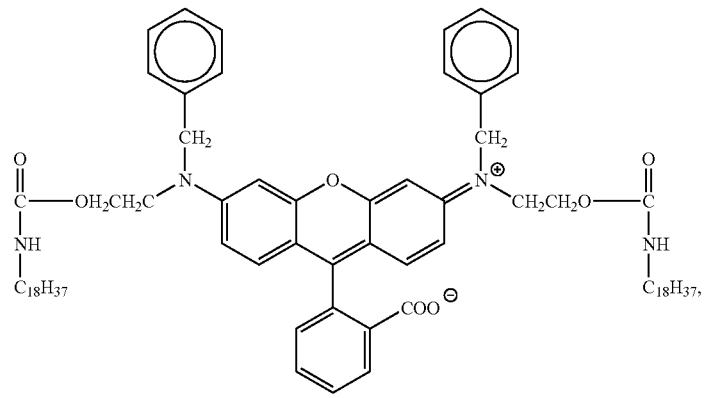
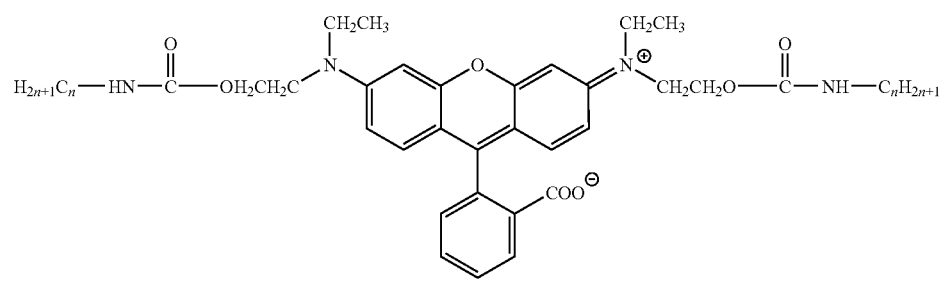
wherein n is at least 12,

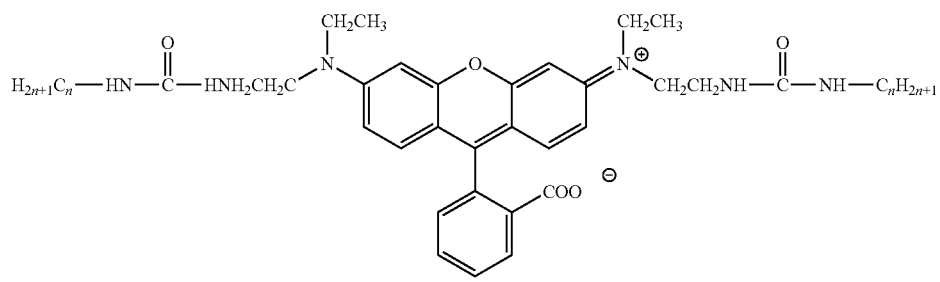
wherein n is at least 12,
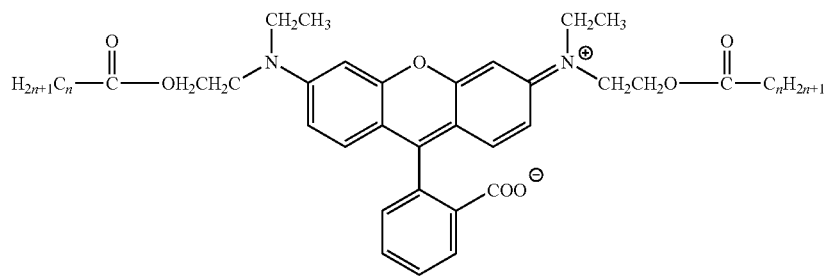
wherein n is at least 12,
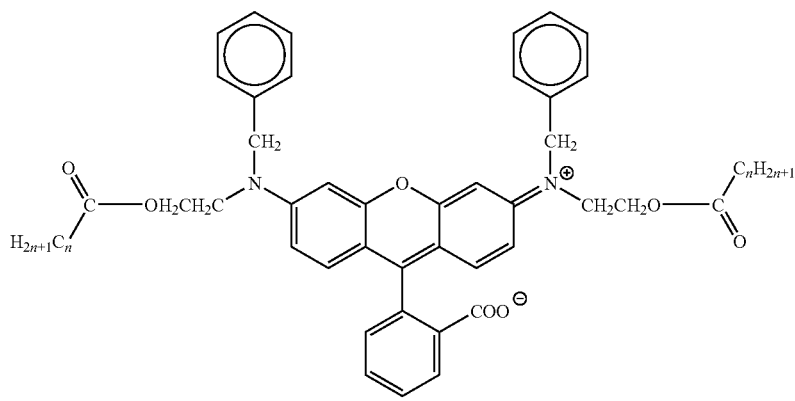
wherein n has an average value of at least 12,
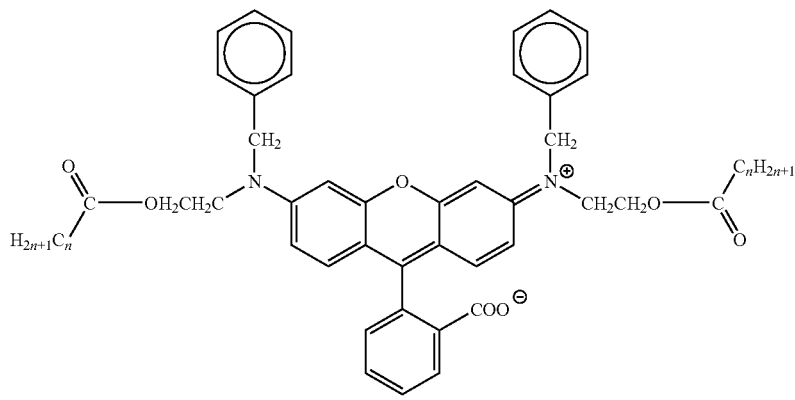
wherein n has an average value of about 50,

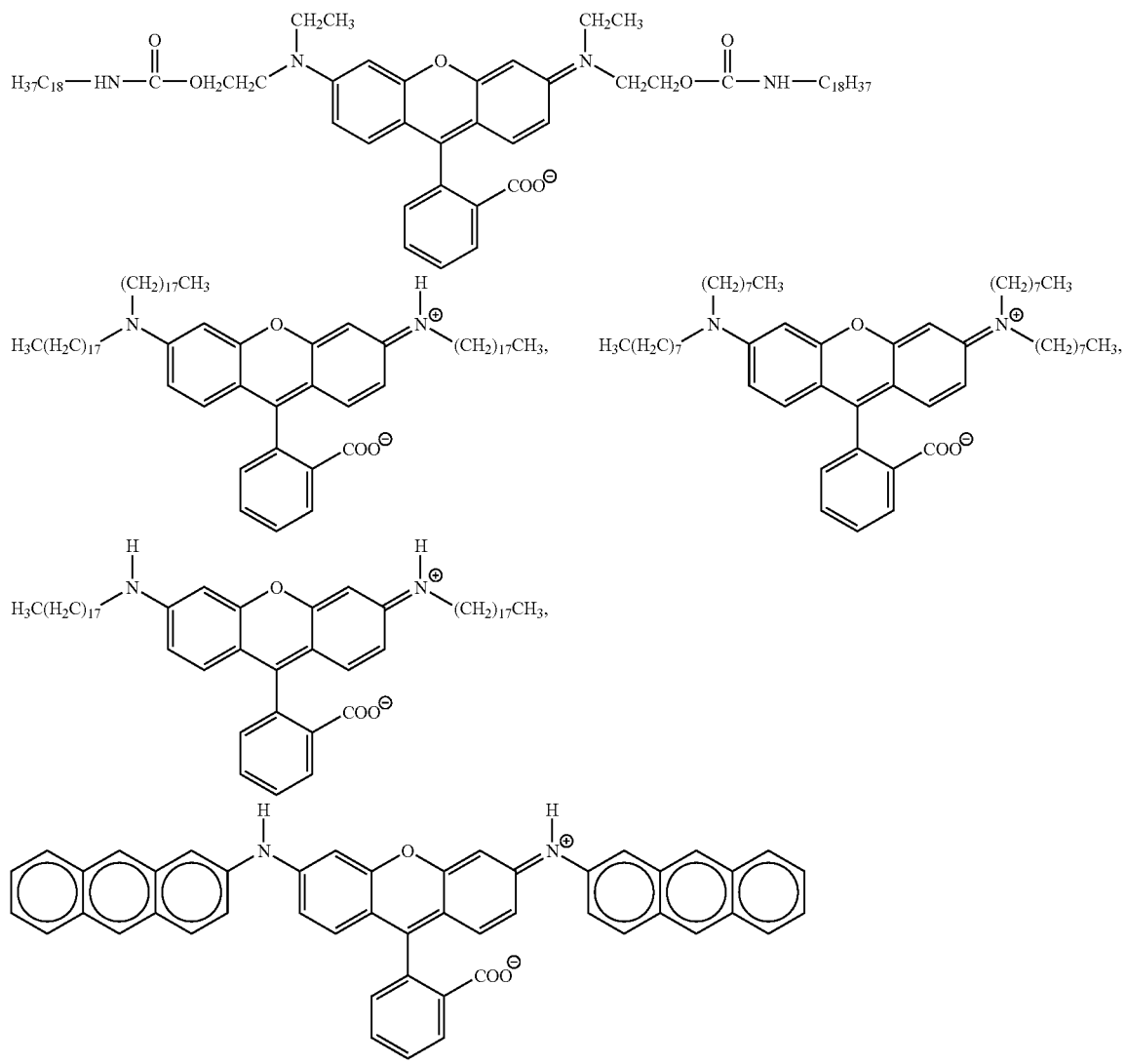
or mixtures thereof.
* * * * *